US006432408B1

US 6,432,408 B1

(12) United States Patent
Meng et al.

(10) Patent No.: US 6,432,408 B1
(45) Date of Patent: Aug. 13, 2002

(54) SWINE HEPATITIS E VIRUS AND USES THEREOF

(75) Inventors: Xiang-Jin Meng, Blacksburg, VA (US); Suzanne U. Emerson, Kensington; Robert H. Purcell, Boyds, both of MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/462,606

(22) PCT Filed: Jul. 17, 1998

(86) PCT No.: PCT/US98/14665

§ 371 (c)(1),
(2), (4) Date: Jun. 12, 2000

(87) PCT Pub. No.: WO99/04029

PCT Pub. Date: Jan. 28, 1999

Related U.S. Application Data

(60) Provisional application No. 60/053,069, filed on Jul. 18, 1997.

(51) Int. Cl.[7] .................. A61K 39/12; A61K 32/29; C12Q 1/70; C07K 19/00
(52) U.S. Cl. .................. 424/189.1; 424/185.1; 530/350; 435/5; 435/236; 536/23.72

(58) Field of Search .................. 424/189.1, 185.1; 530/350; 536/23.72; 435/5, 236

(56) References Cited

FOREIGN PATENT DOCUMENTS

WO    WO 96/10580    4/1996 ........... C07K/14/08

OTHER PUBLICATIONS

Purcell hepatitis E virus in Fields Virology, Edited by Fields et al. 1996, 3rd Ed, Lippinocott–Reven, Philadelphia, vol. 2, pp. 2831–2843.*
Clayson et al. Am. J. tro Med. Hyg. 1995, vol. 53 (3), pp. 228–232.*
Clayson et al, "Detection of Hepatitis E Virus Infections Among Domestic Swine in the Kathmandu Valley of Nepal", *Am. J. Trop. Med. Hyg.*, 53(3), 1995, pp. 228–232.
Meng et al, "A novel virus in swine is closely related to the human hepatitis E virus", *Proc. Natl. Acad. Sci. USA*, vol. 94, pp. 9860–9865, Sep. 1997.

* cited by examiner

*Primary Examiner*—Ali R. Salimi
*Assistant Examiner*—Bao Qun Li
(74) *Attorney, Agent, or Firm*—Morgan & Finnegan LLP.

(57) ABSTRACT

The present invention discloses the isolation and chaterization of a novel swine hepatitis E virus and the use of the virus, the proteins and its nucleic acid sequence as diagnostic reagents and vaccines.

5 Claims, 23 Drawing Sheets

```
Sar55        MRPRPILLLLLMFLPMLPAPPPGQPSGRRRGRRSGGSGGGFWGDRVDSQPFAIPYIHPTN  60
Mexico       .....L...F.L........T.............T........................  60
KS2-87       ............................................................  60
Burma        ............................................................  60
Madras       ............................................................  60
Uigh179      .............IV.............................................  60
HEV037       ...................................................H......  60
Hyderabad    .G......F......L............................................  60
NE8L         ............................................................  60
Hetian       ..........................................A...............  60
Swine HEV    ....AV....FVL........A........C...N..A.............L.......  60

Sar55        PFAPDVTAAAGAGPRVRQPARPLGSAWRDQAQRPAAASRRRPTTAGAAPLTAVAPAHDTP 120
Mexico       ......A..S.S...L........T........S.............A..........S 120
KS2-87       .....................V..........................A......... 120
Burma        .....................V..........................V......... 120
Madras       ................S..............................P.......... 120
Uigh179      ............................................................ 120
HEV037       ..................................T......................... 120
Hyderabad    ....N..........V............................................ 120
NE8L         ..............................................V............ 120
Hetian       ............................................................ 120
Swine HEV    ...A..VSQP...D.P...P..........S...ST.P...SAP.........S..P..A 120

Sar55        PVPDVDSRGAILRRQYNLSTSPLTSSVATGTNLVLYAAPLSPLLPLQDGTNTHIMATEAS 180
Mexico       ...............................S...........N.P............ 180
KS2-87       ............................................................ 180
Burma        ............................................................ 180
Madras       ............................................................ 180
Uigh179      ............................................................ 180
HEV037       ..................................P........................ 180
Hyderabad    ............................................................ 180
NE8L         .........A................................................. 180
Hetian       ............................................................ 180
Swine HEV    ..........................A...............N................ 180

Sar55        NYAQYRVARATIRYRPLVPNAVGGYAISISFWPQTTTTPTSVDMNSITSTDVRILVQPGI 240
Mexico       ............................................................ 240
KS2-87       ............................................................ 240
Burma        ............................................................ 240
Madras       ............................................................ 240
Uigh179      ...........................G................................ 240
HEV037       ............................................................ 240
Hyderabad    .................................P.......................... 240
NE8L         ......V..................................................... 240
Hetian       ......V..................................................... 240
Swine HEV    ......V..................................................... 240
```

FIG. 3A-1

```
Sar55       ASELVIPSERLHYRNQGWRSVETSGVAEEEATSGLVMLCIHGSPVNSYTNTPYTGALGLL 300
Mexico      ............................................................ 300
KS2-87      ............................................................ 300
Burma       .......................................L.................... 300
Madras      ........................................................V... 300
Uigh179     ............................................................ 300
HEV037      .......................................L.................... 300
Hyderabad   ............................................................ 300
NE8L        ............................................................ 300
Hetian      ...H...................................L.................... 300
Swine HEV   ...........................T................................ 300

Sar55       DFALELEFRNLTPGNTNTRVSRYSSTARHRLRRGADGTAELTTTAATRFMKDLYFTSTNG 360
Mexico      ............TC..........SA-....................H..GL.. 360
KS2-87      ............................................................ 360
Burma       ............................................................ 360
Madras      ............................................................ 360
Uigh179     ..............................T............................. 360
HEV037      .....F...................................................... 360
Hyderabad   ............................................................ 360
NE8L        ............................................................ 360
Hetian      ............................................................ 360
Swine HEV   ...........T............................H..G... 360

Sar55       VGEIGRGIALTLFNLADTLLGGLPTELISSAGGQLFYSRPVVSANGEPTVKLYTSVENAQ 420
Mexico      ...V........L................................................ 420
KS2-87      ............................................................ 420
Burma       ............................................................ 420
Madras      .................................................R........ 420
Uigh179     ............................................................ 420
HEV037      ............................................................ 420
Hyderabad   ............................................................ 420
NE8L        ..........................................H................ 420
Hetian      ............................................................ 420
Swine HEV   ...V......................................................... 420

Sar55       QDKGIAIPHDIDLGESRVVIQDYDNQHEQDRPTPSPAPSRPFSVLRANDVLWLSLTAAEY 480
Mexico      ....V........D............................................... 480
KS2-87      ............................................................ 480
Burma       ............................................................ 480
Madras      ..............................................A........... 480
Uigh179     ............................................................ 480
HEV037      ............................................................ 480
Hyderabad   .......N.................................................... 480
NE8L        ............................................................ 480
Hetian      ............................................................ 480
Swine HEV   .....T........D.............................................. 480
```

FIG. 3A-2

```
Sar55       DQSTYGSSTGPVYVSDSVTLVNVATGAQAVARSLDWTKVTLDGRPLSTIQQYSKTFFVLP 540
Mexico      .............I.......................S.........P.VE........ 540
KS2-87      ............................................................ 540
Burma       ............................................................ 540
Madras      ............................................................ 540
Uigh179     ..................................................C....... 540
HEV037      ............................................................ 540
Hyderabad   .........................................................I.. 540
NE8L        ........A................................................P...... 540
Hetian      ..............................................T............ 540
Swine HEV   ..T......N.M....T....................S.........T.........Y... 540

Sar55       LRGKLSFWEAGTTKAGYPYNYNTTASDQLLVENAAGHRVAISTYTTSLGAGPVSISAVAV 600
Mexico      ............................I.I............R......A...A.. 600
KS2-87      ............................................................ 600
Burma       ............................................................ 600
Madras      ............................................................ 600
Uigh179     ............................................................ 600
HEV037      ............................I.....................A...... 600
Hyderabad   ...........RP............................................... 600
NE8L        ............................................................ 600
Hetian      ............................................................ 600
Swine HEV   ............................I.I...................T.....G. 600

Sar55       LAPHSVLALLEDTMDYPARAHTFDDFCPECRPLGLQGCAFQSTVAELQRLKMKVGKTREL 660
Mexico      ...R.A.......F...G..........A.......................V...... 660
KS2-87      .T...A...................................................... 660
Burma       .....A.......L............................................ 660
Madras      .....A.......L............................................ 660
Uigh179     .....A.................................................... 660
HEV037      .....A.................................................... 660
Hyderabad   .G...A.......L............................................ 660
NE8L        .....A.......L....C........................................ 660
Hetian      .....A.................................................... 660
Swine HEV   .....A..V....V..............T..........I...................S 660
```

FIG. 3A-3

```
Sar55       MNNMSFAAPMGSRPCALGLFCCCSSCFCLCCPRHRPVSRLAAVVGGAAAVPAVVSGVTGL 123
Mexico      ....W.......P............................................. 123
Madras      ............................................................ 123
Burma       ............................................................ 123
KS2-87      ..........P................................................. 123
NE8L        .............D.............................................. 123
HEV037      ............................................................ 123
Uigh179     ....W...............S....................................... 123
Hetian      .....S..................................A.................. 123
Hyderabad   .D........W.........S........................................ 123
Swine HEV   ......S....-.................A..............T.............. 123

***************** (HVR, position 79-96)
Sar55       ILSPSQSPIFIQPTPSPPMSPLRPGLDLVFANPPDHSAPLGVTRPSAPPLPHVVDLPQLGPRR 123
Mexico      ..............L.QTL........A...Q.G.L....EI........P.A....P.L.. 123
Madras      .............................................................. 123
Burma       .............................................................. 123
KS2-87      ................................S............................. 123
NE8L        ................................Q............................. 123
HEV037      ............L............A..................................... 123
Uigh179     .............................................................. 123
Hetian      .............................................................. 123
Hyderabad   ...............R................S.......A...................... 123
Swine HEV   .....P..........L...FHN...EFALDSR.APL......S........P........L.. 123
```

FIG. 3B

| | |
|---|---|
| ATGGAGGCCC ATCAGTTCAT TAAGGCTCCT GGCATTACTA | 40 |
| CTGCCATTGA GCAGGCTGCT CTGGCTGCGG CCAACTCCGC | 80 |
| CTTGGCGAAT GCTGTGGTGG TTCGGCCGTT TTTATCTCGT | 120 |
| GTACAAACTG AGATCCTTAT TAATTTGATG CAACCCCGGC | 160 |
| AGTTGGTTTT CCGCCCTGAG GTACTTTGGA ATCATCCTAT | 200 |
| CCAGCGGGCA ATACATAATG AACTGGAACA GTACTGCCGA | 240 |
| GCCCGGGCTG GTTGTTGTTT GGAAGTTGGA GCCCATCCGA | 280 |
| GATTTATTAA TGACAATCCC AACGTCCTGC ACCGGTGCTT | 320 |
| CCTTAGACCG GTTGGCCGAG ATGTCCAGCG CTGGTACTCT | 360 |
| GCCCCCACCC GTGGCCCTGC GGCCAATTGT CGCCGCTCCG | 400 |
| CGCTGCGTGG CCTTCCCCCC GTCGACCGCA CTTACTGTTT | 440 |
| TGATGGATTC TCTCGTTGTG CTTTCGCTGC AGAGACCGGT | 480 |
| GTGGCCCTCT ACTCTTTACA TGACCTTTGG CCAGCTGATG | 520 |
| TTGCGGAGGC TATGGCCCGC CACGGGATGA CACGCCTATA | 560 |
| CGCCGCACTG CACCTTCTTC CCGAGGTGCT GCTACCACCC | 600 |
| GGCACCTACC ACACAACTTC GTACCTCCTG ATTACGACG | 640 |
| GTGACCGCGC TGTTGTGACT TATGAGGGCG ATACTAGTGC | 680 |
| GGGCTATAAC CATGATGTCT CCATACTCCG TGCGTGGATC | 720 |
| CGTACCACTA AAATAGTTGG TGACCACCCG TTGGTTATAG | 760 |
| AGCGTGTGCG GGCCATTGGC TGTCATTTTG TGCTGCTGCT | 800 |
| CACCGCAGCC CCTGAACCGT CACCTATGCC TTATGTCCCC | 840 |
| TACCCTCGTT CAACGGAGGT GTATGTTCGA TCCATATTTG | 880 |
| GCCCTGGCGG CTCCCCATCC TTGTTTCCGT CAGCCTGCTC | 920 |
| TACTAAATCT ACATTTCATG CTGTCCCGGT TCATATCTGG | 960 |
| GATCGGCTCA TGCTTTTTGG TGCCACCCTG GATGACCAGG | 1000 |
| CCTTTTGTTG TTCACGGCTC ATGACCTACC TCCGTGGTAT | 1040 |
| TAGCTACAAG GTCACTGTCG GTGCGCTTGT CGCTAATGAG | 1080 |
| GGGTGGAACG CCTCTGAAGA TGCTCTTACT GCAGTGATTA | 1120 |
| CTGCCGCTTA TCTGACTATT TGCCATCAGC GTTATCTTCG | 1160 |
| CACCCAGGCG ATATCCAAGG GCATGCGCCG GCTGGAGGTT | 1200 |
| GAGCACGCCC AGAAATTTAT CACAAGACTT TACAGTTGGC | 1240 |
| TATTTGAGAA GTCTGGCCGT GATTATATCC CCGGCCGTCA | 1280 |
| GCTTCAGTTC TACGCACAGT GCCGGCGGTG GTTATCTGCA | 1320 |
| GGCTTCCACC TAGACCCCAG GGTGCTTGTT TTTGATGAAT | 1360 |
| CAGTGCCATG CCGCTGCAGG ACGTTTTTGA AGAAAGTCGC | 1400 |
| AGGTAAGTTC TGCTGTTTTA TGCGGTGGTT AGGGCAGGAG | 1440 |
| TGTACCTGTT TCTTGGAGCC AGCCGAAGGC TTGGTTGGCG | 1480 |
| ACTATGGCCA TGACAACGAG GCCTATGAGG GTTCTGAGGT | 1520 |
| CGACCCGGCT GAACCTGCTC ATCTTGATGT TTCTGGGACC | 1560 |
| TATGCCGTTC ACGGGCGCCA GCTTGAGGCT CTCTATAGGG | 1600 |
| CACTTAATGT CCCACATGAC ATCGCCGCTC GAGCCTCCCG | 1640 |
| CCTAACGGCT ACTGTTGAGC TCACTGCAAG CCCAGACCGT | 1680 |
| TTAGAGTGCC GCACTGTGCT TGGTAATAAG ACCTTCAGGA | 1720 |
| CGACGGTGGT TGATGGCGCC CATCTTGAGG CGAATGGTCC | 1760 |
| TGAGCAGTAT GTCCTATCAT TCGACGCCTC CCGCCAGTCT | 1800 |
| ATGGGGGCCG GGTCACATAG CCTCACTTAT GAGCTCACCC | 1840 |
| CTGCCGGCCT GCAGGTCAGG ATTTCATCTA ATGGCCTGGA | 1880 |

FIG. 6A

```
TTGCACAGCC ACATTCCCCC CCGGCGGCGC CCCTAGCGCT        1920
GCGCCGGGGG AGGTGGCGGC CTTTTGCAGT GCCCTTTATA        1960
GATATAATAG GTTCACCCAG CGGCATTCGC TGACCGGTGG        2000
GTTATGGCTA CACCCTGAGG GATTGCTGGG CATCTTCCCC        2040
CCTTTCTCCC CTGGGCACAT TTGGGAGCCT GCTAACCCTT        2080
TCTGCGGGGA GGGGACTTTG TATACCCGGA CTTGGTCAAC        2120
ATCTGGCTTT TCTAGCGATT TCTCCCCCCC TGAGGCGGCC        2160
GCCCCCGTTT TGGCCGCTGC CCCGGGGCTG CCCCACCCTA        2200
CCCCACCTGT TAGTGACATT TGGGTGTTAC CACCACCTTC        2240
AAAGGAGTCT CAGGTCGATG CGGCATCTGT GCCCCCTGCT        2280
CCTGAGCCCG CTGGATTACC CAGCTCCATT GTGCTTACCC        2320
TCCCCCCCCC CCTCCCTCCT GTGCGTAAGC CACCAACACC        2360
CCCGCCTTCC CGCACTCGTC GTCTCCTCTA CACCTATCCC        2400
GACGGCGCAA AGGTGTATGC GGGTCATTG TTTGAATCAG         2440
ACTGTAACTG GCTGGTTAAT GCCTCAAACC CGGGCCACCG        2480
CCCTGGAGGT GGCCTCTGCC ATGCTTTTTA CCAACGTTTC        2520
CCAGAGGCGT TTTACCCGAC TGAGTTCATT ATGCGTGAGG        2560
GCCTTGCAGC ATATACCCTG ACCCGCGCC CTATCATTCA         2600
TGCAGTGGCC CCCGACTATA GGGTTGAGCA GAATCCGAAG        2640
AGGCTTGAGG CAGCGTACCG GGAGACTTGC TCCCGTCGTG        2680
GCACCGCCGC CTACCCGCTT CTAGGCTCGG GTATATACCA        2720
GGTCCCTGTC AGCCTCAGTT TTGATGCCTG GGAACGCAAT        2760
CACCGCCCCG GCGATGAGCT TTATTTGACT GAGCCCGCCG        2800
CAGCCTGGTT CGAGGCTAAT AAGCCGGCGC AGCCGGCGCT        2840
TACTATAACT GAGGACACAG CCCGTACGGC CAACCTAGCG        2880
TTAGAGATCG ATGCTGCCAC AGATGTTGGC CGTGCTTGTG        2920
CCGGCTGCAC TATCAGTCCT GGGATTGTGC ACTATCAGTT        2960
CACTGCCGGG GTCCCAGGCT CGGGCAAGTC TCGGTCCATA        3000
CAACAGGGAG ATGTCGATGT GGTGGTCGTG CCCACCCGGG        3040
AGCTCCGTAA TAGTTGGCGT CGCCGGGGTT TTGCGGCTTT        3080
CACACCTCAC ACAGCAGCCC GTGTCACTAT CGGTCGCCGC        3120
GTTGTGATTG ATGAGGCTCC ATCTCTCCCT CCACACCTGT        3160
TGCTGTTACA CATGCAGCGG GCCTCCTCGG TCCATCTCCT        3200
TGGTGACCCA AATCAGATCC CTGCCATTGA TTTTGAACAC        3240
GCCGGCCTGG TTCCCGCGAT CCGCCCTGAG CTTGCTCCAA        3280
CGAGCTGGTG GCACGTTACA CACCGTTGCC CGGCCGATGT        3320
ATGCGAGCTC ATACGCGGAG CCTACCCTAA AATCCAGACC        3360
ACGAGCCGTG TGCTGCGGTC CCTGTTCTGG AACGAACCTG        3400
CTATCGGCCA GAAGTTGGTC TTCACGCAGG CTGCTAAAGC        3440
TGCTAACCCT GGTGCGATTA CGGTTCATGA AGCTCAGGGT        3480
GCCACTTTTA CAGAGACCAC AATTATAGCC ACGGCCGATG        3520
CCAGGGGCCT TATCCAGTCA TCCCGGGCTC ACGCTATAGT        3560
CGCACTCACC CGCCACACTG AGAAGTGTGT TATTCTGGAT        3600
GCTCCCGGCC TGCTGCGTGA GGTCGGCATT TCGGATGTGA        3640
TTGTCAATAA CTTTTTCCTT GCTGGCGGAG AAGTCGGCCA        3680
TCACCGCCCT TCTGTGATAC CCCGCGGTAA CCCTGATCAG        3720
AACCTCGGGA CTCTACAGGC CTTCCCGCCG TCCTGCCAGA        3760
```

FIG. 6B

```
TTAGTGCTTA CCACCAATTG GCTGAAGAAT TAGGCCACCG    3800
TCCGGCTCCT GTTGCCGCCG TCTTGCCCCC TTGCCCTGAG    3840
CTTGAGCAGG GCCTGCTCTA TATGCCACAA GAGCTTACTG    3880
TGTCTGATAG TGTGTTGGTT TTTGAGCTCA CGGATATAGT    3920
CCACTGTCGC ATGGCCGCTC CGAGCCAGCG AAAGGCTGTT    3960
CTCTCAACAC TTGTAGGGAG ATACGGCCGT AGGACGAAAT    4000
TATATGAGGC AGCGCATTCA GATGTTCGTG AGTCCCTGGC    4040
CAGGTTCATT CCCACTATCG GGCCTGTTCA GGCCACCACA    4080
TGTGAGTTGT ATGAGTTGGT TGAGGCATG GTGGAGAAGG     4120
GACAGGACGG CTCTGCCGTC CTAGAGCTTG ACCTTTGCAA    4160
TCGTGACGTA TCGCGCATCA CATTTTTCCA AAAGGATTGC    4200
AACAAGTTTA CAACTGGTGA GACTATCGCC CATGGCAAGG    4240
TTGGTCAGGG TATATCGGCC TGGAGTAAGA CCTTCTGTGC    4280
TCTGTTTGGC CCGTGGTTCC GTGCCATTGA AAAAGAAATA    4320
CTGGCCCTAC TCCCGCCTAA TATCTTTTAT GGCGACGCCT    4360
ATGAGGAATC AGTGTTCGCT GCCGCTGTGT CCGGGGCGGG    4400
GTCGTGCATG GTATTTGAAA ATGACTTTTC AGAGTTTGAC    4440
AGTACCCAAA ATAATTTCTC CCTTGGCCTT GAGTGTGTGG    4480
TTATGGAGGA GTGCGGCATG CCCCAGTGGC TAATTAGGTT    4520
GTATCATCTG GTTCGGTCAG CCTGGATTTT GCAGGCGCCG    4560
AAGGAGTCTC TTAAGGGTTT CTGGAAGAAG CATTCTGGTG    4600
AGCCTGGTAC CCTTCTCTGG AACACCGTCT GGAACATGGC    4640
GATTATAGCA CATTGTTATG AGTTTCGTGA CTTTCGTGTT    4680
GCCGCCTTCA AGGGTGATGA TTCAGTGGTC CTTTGTAGTG    4720
ACTACCGACA GAGCCGTAAT GCGGCTGCCT TAATTGCAGG    4760
CTGTGGGCTC AAATTGAAGG TTGACTACCG CCCTATTGGG    4800
CTGTATGCCG GGGTGGTGGT GGCCCCTGGT CTGGGGACAC    4840
TGCCTGATGT TGTGCGTTTC GCCGGTCGGT TGTCTGAAAA    4880
GAATTGGGGC CCCGGCCCAG AGCGTGCTGA GCAGCTGCGT    4920
CTTGCTGTTT GTGACTTCCT TCAGGGTTG ACAAATGTTG     4960
CGCAGGTTTG TGTTGATGTT GTGTCCCGTG TTTATGGAGT    5000
TAGCCCCGGG CTGGTGCATA ACCTTATTGG CATGCTGCAG    5040
ACTATTGCCG ATGGCAAGGC CCACTTTACA GAGACTATTA    5080
AACCTGTGCT TGACCTTACA AACTCTATCA TACAGCGGGT    5120
GGAATGA                                        5127
```

FIG. 6C

```
Met Glu Ala His Gln Phe Ile Lys Ala Pro Gly Ile
                    5                   10
Thr Thr Ala Ile Glu Gln Ala Ala Leu Ala Ala Ala
            15              20
Asn Ser Ala Leu Ala Asn Ala Val Val Val Arg Pro
 25              30                      35
Phe Leu Ser Arg Val Gln Thr Glu Ile Leu Ile Asn
            40              45
Leu Met Gln Pro Arg Gln Leu Val Phe Arg Pro Glu
     50              55                      60
Val Leu Trp Asn His Pro Ile Gln Arg Ala Ile His
                65              70
Asn Glu Leu Glu Gln Tyr Cys Arg Ala Arg Ala Gly
         75              80
Cys Cys Leu Glu Val Gly Ala His Pro Arg Phe Ile
 85              90                      95
Asn Asp Asn Pro Asn Val Leu His Arg Cys Phe Leu
            100             105
Arg Pro Val Gly Arg Asp Val Gln Arg Trp Tyr Ser
     110             115                     120
Ala Pro Thr Arg Gly Pro Ala Ala Asn Cys Arg Arg
            125                 130
Ser Ala Leu Arg Gly Leu Pro Pro Val Asp Arg Thr
         135                 140
Tyr Cys Phe Asp Gly Phe Ser Arg Cys Ala Phe Ala
145                 150                     155
Ala Glu Thr Gly Val Ala Leu Tyr Ser Leu His Asp
            160                 165
Leu Trp Pro Ala Asp Val Ala Glu Ala Met Ala Arg
     170             175                     180
His Gly Met Thr Arg Leu Tyr Ala Ala Leu His Leu
            185                 190
Leu Pro Glu Val Leu Leu Pro Pro Gly Thr Tyr His
         195                 200
Thr Thr Ser Tyr Leu Leu Ile His Asp Gly Asp Arg
205                 210                     215
Ala Val Val Thr Tyr Glu Gly Asp Thr Ser Ala Gly
            220                 225
Tyr Asn His Asp Val Ser Ile Leu Arg Ala Trp Ile
230                 235                     240
Arg Thr Thr Lys Ile Val Gly Asp His Pro Leu Val
            245                 250
Ile Glu Arg Val Arg Ala Ile Gly Cys His Phe Val
     255                 260                 265
Leu Leu Leu Thr Ala Ala Pro Glu Pro Ser Pro Met
                270                 275
```

FIG. 6D

```
Pro Tyr Val Pro Tyr Pro Arg Ser Thr Glu Val Tyr
        280             285
Val Arg Ser Ile Phe Gly Pro Gly Gly Ser Pro Ser
290             295             300
Leu Phe Pro Ser Ala Cys Ser Thr Lys Ser Thr Phe
            305             310
His Ala Val Pro Val His Ile Trp Asp Arg Leu Met
    315             320             325
Leu Phe Gly Ala Thr Leu Asp Asp Gln Ala Phe Cys
            330             335
Cys Ser Arg Leu Met Thr Tyr Leu Arg Gly Ile Ser
        340             345
Tyr Lys Val Thr Val Gly Ala Leu Val Ala Asn Glu
350             355             360
Gly Trp Asn Ala Ser Glu Asp Ala Leu Thr Ala Val
            365             370
Ile Thr Ala Ala Tyr Leu Thr Ile Cys His Gln Arg
    375             380             385
Tyr Leu Arg Thr Gln Ala Ile Ser Lys Gly Met Arg
            390             395
Arg Leu Glu Val Glu His Ala Gln Lys Phe Ile Thr
        400             405
Arg Leu Tyr Ser Trp Leu Phe Glu Lys Ser Gly Arg
410             415             420
Asp Tyr Ile Pro Gly Arg Gln Leu Gln Phe Tyr Ala
            425             430
Gln Cys Arg Arg Trp Leu Ser Ala Gly Phe His Leu
    435             440             445
Asp Pro Arg Val Leu Val Phe Asp Glu Ser Val Pro
            450             455
Cys Arg Cys Arg Thr Phe Leu Lys Lys Val Ala Gly
    460             465
Lys Phe Cys Cys Phe Met Arg Trp Leu Gly Gln Glu
470             475             480
Cys Thr Cys Phe Leu Glu Pro Ala Glu Gly Leu Val
            485             490
Gly Asp Tyr Gly His Asp Asn Glu Ala Tyr Glu Gly
    495             500             505
Ser Glu Val Asp Pro Ala Glu Pro Ala His Leu Asp
            510             515
Val Ser Gly Thr Tyr Ala Val His Gly Arg Gln Leu
        520             525
Glu Ala Leu Tyr Arg Ala Leu Asn Val Pro His Asp
530             535             540
Ile Ala Ala Arg Ala Ser Arg Leu Thr Ala Thr Val
            545             550
Glu Leu Thr Ala Ser Pro Asp Arg Leu Glu Cys Arg
```

FIG. 6E

```
              555                    560                    565
Thr Val Leu Gly Asn Lys Thr Phe Arg Thr Thr Val
                    570                575
Val Asp Gly Ala His Leu Glu Ala Asn Gly Pro Glu
            580                585
Gln Tyr Val Leu Ser Phe Asp Ala Ser Arg Gln Ser
590                     595                    600
Met Gly Ala Gly Ser His Ser Leu Thr Tyr Glu Leu
                605                    610
Thr Pro Ala Gly Leu Gln Val Arg Ile Ser Ser Asn
        615                 620                    625
Gly Leu Asp Cys Thr Ala Thr Phe Pro Pro Gly Gly
                630                     635
Ala Pro Ser Ala Ala Pro Gly Glu Val Ala Ala Phe
            640                    645
Cys Ser Ala Leu Tyr Arg Tyr Asn Arg Phe Thr Gln
650                     655                    660
Arg His Ser Leu Thr Gly Gly Leu Trp Leu His Pro
                665                    670
Glu Gly Leu Leu Gly Ile Phe Pro Pro Phe Ser Pro
        675                     680                    685
Gly His Ile Trp Glu Pro Ala Asn Pro Phe Cys Gly
                    690                    695
Glu Gly Thr Leu Tyr Thr Arg Thr Trp Ser Thr Ser
                700                    705
Gly Phe Ser Ser Asp Phe Ser Pro Pro Glu Ala Ala
710                     715                    720
Ala Pro Val Leu Ala Ala Ala Pro Gly Leu Pro His
                725                    730
Pro Thr Pro Pro Val Ser Asp Ile Trp Val Leu Pro
        735                     740                    745
Pro Pro Ser Lys Glu Ser Gln Val Asp Ala Ala Ser
                    750                    755
Val Pro Pro Ala Pro Glu Pro Ala Gly Leu Pro Ser
        760                         765
Ser Ile Val Leu Thr Leu Pro Pro Pro Leu Pro Pro
770                     775                    780
Val Arg Lys Pro Pro Thr Pro Pro Pro Ser Arg Thr
                785                     790
Arg Arg Leu Leu Tyr Thr Tyr Pro Asp Gly Ala Lys
        795                     800                    805
Val Tyr Ala Gly Ser Leu Phe Glu Ser Asp Cys Asn
                    810                    815
Trp Leu Val Asn Ala Ser Asn Pro Gly His Arg Pro
            820                    825
Gly Gly Gly Leu Cys His Ala Phe Tyr Gln Arg Phe
        830                     835                    840
```

FIG. 6F

```
Pro Glu Ala Phe Tyr Pro Thr Glu Phe Ile Met Arg
                845                 850
Glu Gly Leu Ala Ala Tyr Thr Leu Thr Pro Arg Pro
        855                 860                 865
Ile Ile His Ala Val Ala Pro Asp Tyr Arg Val Glu
                    870                 875
Gln Asn Pro Lys Arg Leu Glu Ala Ala Tyr Arg Glu
        880                     885
Thr Cys Ser Arg Arg Gly Thr Ala Ala Tyr Pro Leu
890                     895                 900
Leu Gly Ser Gly Ile Tyr Gln Val Pro Val Ser Leu
            905                     910
Ser Phe Asp Ala Trp Glu Arg Asn His Arg Pro Gly
        915                 920                 925
Asp Glu Leu Tyr Leu Thr Glu Pro Ala Ala Ala Trp
                    930                 935
Phe Glu Ala Asn Lys Pro Ala Gln Pro Ala Leu Thr
        940                     945
Ile Thr Glu Asp Thr Ala Arg Thr Ala Asn Leu Ala
950                     955                 960
Leu Glu Ile Asp Ala Ala Thr Asp Val Gly Arg Ala
            965                     970
Cys Ala Gly Cys Thr Ile Ser Pro Gly Ile Val His
        975                 980                 985
Tyr Gln Phe Thr Ala Gly Val Pro Gly Ser Gly Lys
                    990                 995
Ser Arg Ser Ile Gln Gln Gly Asp Val Asp Val Val
            1000                1005
Val Val Pro Thr Arg Glu Leu Arg Asn Ser Trp Arg
1010                    1015                1020
Arg Arg Gly Phe Ala Ala Phe Thr Pro His Thr Ala
                1025                1030
Ala Arg Val Thr Ile Gly Arg Arg Val Val Ile Asp
        1035                1040                1045
Glu Ala Pro Ser Leu Pro Pro His Leu Leu Leu Leu
                    1050                1055
His Met Gln Arg Ala Ser Ser Val His Leu Leu Gly
            1060                1065
Asp Pro Asn Gln Ile Pro Ala Ile Asp Phe Glu His
1070                    1075                1080
Ala Gly Leu Val Pro Ala Ile Arg Pro Glu Leu Ala
                1085                1090
Pro Thr Ser Trp Trp His Val Thr His Arg Cys Pro
        1095                1100                1105
Ala Asp Val Cys Glu Leu Ile Arg Gly Ala Tyr Pro
                1110                1115
Lys Ile Gln Thr Thr Ser Arg Val Leu Arg Ser Leu
```

FIG. 6G

```
                    1120                       1125
Phe Trp Asn Glu Pro Ala Ile Gly Gln Lys Leu Val
1130                1135                  1140
Phe Thr Gln Ala Ala Lys Ala Ala Asn Pro Gly Ala
               1145            1150
Ile Thr Val His Glu Ala Gln Gly Ala Thr Phe Thr
          1155            1160                 1165
Glu Thr Thr Ile Ile Ala Thr Ala Asp Ala Arg Gly
                    1170           1175
Leu Ile Gln Ser Ser Arg Ala His Ala Ile Val Ala
               1180           1185
Leu Thr Arg His Thr Glu Lys Cys Val Ile Leu Asp
1190                1195                 1200
Ala Pro Gly Leu Leu Arg Glu Val Gly Ile Ser Asp
                 1205              1210
Val Ile Val Asn Asn Phe Phe Leu Ala Gly Gly Glu
          1215            1220                 1225
Val Gly His His Arg Pro Ser Val Ile Pro Arg Gly
                    1230           1235
Asn Pro Asp Gln Asn Leu Gly Thr Leu Gln Ala Phe
               1240            1245
Pro Pro Ser Cys Gln Ile Ser Ala Tyr His Gln Leu
1250                1255                 1260
Ala Glu Glu Leu Gly His Arg Pro Ala Pro Val Ala
               1265             1270
Ala Val Leu Pro Pro Cys Pro Glu Leu Glu Gln Gly
          1275            1280                 1285
Leu Leu Tyr Met Pro Gln Glu Leu Thr Val Ser Asp
                    1290           1295
Ser Val Leu Val Phe Glu Leu Thr Asp Ile Val His
               1300            1305
Cys Arg Met Ala Ala Pro Ser Gln Arg Lys Ala Val
1310                1315                 1320
Leu Ser Thr Leu Val Gly Arg Tyr Gly Arg Arg Thr
               1325             1330
Lys Leu Tyr Glu Ala Ala His Ser Asp Val Arg Glu
          1335            1340                 1345
Ser Leu Ala Arg Phe Ile Pro Thr Ile Gly Pro Val
                    1350           1355
Gln Ala Thr Thr Cys Glu Leu Tyr Glu Leu Val Glu
               1360            1365
Ala Met Val Glu Lys Gly Gln Asp Gly Ser Ala Val
1370                1375                  1380
Leu Glu Leu Asp Leu Cys Asn Arg Asp Val Ser Arg
               1385            1390
Ile Thr Phe Phe Gln Lys Asp Cys Asn Lys Phe Thr
          1395            1400                 1405
```

FIG. 6H

```
Thr Gly Glu Thr Ile Ala His Gly Lys Val Gly Gln
                1410                1415
Gly Ile Ser Ala Trp Ser Lys Thr Phe Cys Ala Leu
        1420            1425
Phe Gly Pro Trp Phe Arg Ala Ile Glu Lys Glu Ile
1430            1435                1440
Leu Ala Leu Leu Pro Pro Asn Ile Phe Tyr Gly Asp
                1445            1450
Ala Tyr Glu Glu Ser Val Phe Ala Ala Ala Val Ser
        1455            1460            1465
Gly Ala Gly Ser Cys Met Val Phe Glu Asn Asp Phe
                1470            1475
Ser Glu Phe Asp Ser Thr Gln Asn Asn Phe Ser Leu
        1480            1485
Gly Leu Glu Cys Val Val Met Glu Glu Cys Gly Met
1490            1495            1500
Pro Gln Trp Leu Ile Arg Leu Tyr His Leu Val Arg
                1505            1510
Ser Ala Trp Ile Leu Gln Ala Pro Lys Glu Ser Leu
        1515            1520            1525
Lys Gly Phe Trp Lys Lys His Ser Gly Glu Pro Gly
                1530            1535
Thr Leu Leu Trp Asn Thr Val Trp Asn Met Ala Ile
        1540            1545
Ile Ala His Cys Tyr Glu Phe Arg Asp Phe Arg Val
1550            1555            1560
Ala Ala Phe Lys Gly Asp Asp Ser Val Val Leu Cys
                1565            1570
Ser Asp Tyr Arg Gln Ser Arg Asn Ala Ala Ala Leu
        1575            1580            1585
Ile Ala Gly Cys Gly Leu Lys Leu Lys Val Asp Tyr
                1590            1595
Arg Pro Ile Gly Leu Tyr Ala Gly Val Val Val Ala
        1600            1605
Pro Gly Leu Gly Thr Leu Pro Asp Val Val Arg Phe
1610            1615            1620
Ala Gly Arg Leu Ser Glu Lys Asn Trp Gly Pro Gly
                1625            1630
Pro Glu Arg Ala Glu Gln Leu Arg Leu Ala Val Cys
        1635            1640            1645
Asp Phe Leu Arg Gly Leu Thr Asn Val Ala Gln Val
                1650            1655
Cys Val Asp Val Val Ser Arg Val Tyr Gly Val Ser
                1660            1665
Pro Gly Leu Val His Asn Leu Ile Gly Met Leu Gln
1670            1675            1680
Thr Ile Ala Asp Gly Lys Ala His Phe Thr Glu Thr
```

FIG. 6I

```
              1685                    1690
Ile Lys Pro Val Leu Asp Leu Thr Asn Ser Ile Ile
    1695                1700                 1705
Gln Arg Val Glu
            1709
```

FIG. 6J

```
TTCGATGCCA TGGAGGCCCA TCAGTTCATT AAGGCTCCTG           40
GCATTACTAC TGCCATTGAG CAGGCTGCTC TGGCTGCGGC           80
CAACTCCGCC TTGGCGAATG CTGTGGTGGT TCGGCCGTTT          120
TTATCTCGTG TACAAACTGA GATCCTTATT AATTTGATGC          160
AACCCCGGCA GTTGGTTTTC CGCCCTGAGG TACTTTGGAA          200
TCATCCTATC CAGCGGGCAA TACATAATGA ACTGGAACAG          240
TACTGCCGAG CCCGGGCTGG TTGTTGTTTG GAAGTTGGAG          280
CCCATCCGAG ATTTATTAAT GACAATCCCA ACGTCCTGCA          320
CCGGTGCTTC CTTAGACCGG TTGGCCGAGA TGTCCAGCGC          360
TGGTACTCTG CCCCCACCCG TGGCCCTGCG GCCAATTGTC          400
GCCGCTCCGC GCTGCGTGGC CTTCCCCCCG TCGACCGCAC          440
TTACTGTTTT GATGGATTCT CTCGTTGTGC TTTCGCTGCA          480
GAGACCGGTG TGGCCCTCTA CTCTTTACAT GACCTTTGGC          520
CAGCTGATGT TGCGGAGGCT ATGGCCCGCC ACGGGATGAC          560
ACGCCTATAC GCCGCACTGC ACCTTCTTCC CGAGGTGCTG          600
CTACCACCCG GCACCTACCA CACAACTTCG TACCTCCTGA          640
TTCACGACGG TGACCGCGCT GTTGTGACTT ATGAGGGCGA          680
TACTAGTGCG GGCTATAACC ATGATGTCTC CATACTCCGT          720
GCGTGGATCC GTACCACTAA AATAGTTGGT GACCACCCGT          760
TGGTTATAGA GCGTGTGCGG GCCATTGGCT GTCATTTTGT          800
GCTGCTGCTC ACCGCAGCCC CTGAACCGTC ACCTATGCCT          840
TATGTCCCCT ACCTCGTTC AACGGAGGTG TATGTTCGAT           880
CCATATTTGG CCCTGGCGGC TCCCCATCCT TGTTTCCGTC          920
AGCCTGCTCT ACTAAATCTA CATTTCATGC TGTCCCGGTT          960
CATATCTGGG ATCGGCTCAT GCTTTTTGGT GCCACCCTGG         1000
ATGACCAGGC CTTTTGTTGT TCACGGCTCA TGACCTACCT         1040
CCGTGGTATT AGCTACAAGG TCACTGTCGG TGCGCTTGTC         1080
GCTAATGAGG GGTGGAACGC CTCTGAAGAT GCTCTTACTG         1120
CAGTGATTAC TGCCGCTTAT CTGACTATTT GCCATCAGCG         1160
TTATCTTCGC ACCCAGGCGA TATCCAAGGG CATGCGCCGG         1200
CTGGAGGTTG AGCACGCCCA GAAATTTATC ACAAGACTTT         1240
ACAGTTGGCT ATTTGAGAAG TCTGGCCGTG ATTATATCCC         1280
CGGCCGTCAG CTTCAGTTCT ACGCACAGTG CCGGCGGTGG         1320
TTATCTGCAG GCTTCACCT AGACCCCAGG GTGCTTGTTT          1360
TTGATGAATC AGTGCCATGC CGCTGCAGGA CGTTTTTGAA         1400
GAAAGTCGCA GGTAAGTTCT GCTGTTTTAT GCGGTGGTTA         1440
GGGCAGGAGT GTACCTGTTT CTTGGAGCCA GCCGAAGGCT         1480
TGGTTGGCGA CTATGGCCAT GACAACGAGG CCTATGAGGG         1520
TTCTGAGGTC GACCCGGCTG AACCTGCTCA TCTTGATGTT         1560
TCTGGACCT ATGCCGTTCA CGGGCGCCAG CTTGAGGCTC          1600
TCTATAGGGC ACTTAATGTC CCACATGACA TCGCCGCTCG         1640
AGCCTCCCGC CTAACGGCTA CTGTTGAGCT CACTGCAAGC         1680
CCAGACCGTT TAGAGTGCCG CACTGTGCTT GGTAATAAGA         1720
CCTTCAGGAC GACGGTGGTT GATGGCGCCC ATCTTGAGGC         1760
GAATGGTCCT GAGCAGTATG TCCTATCATT CGACGCCTCC         1800
CGCCAGTCTA TGGGGCCGG GTCACATAGC CTCACTTATG          1840
AGCTCACCCC TGCCGGCCTG CAGGTCAGGA TTTCATCTAA         1880
```

FIG. 7A

```
TGGCCTGGAT TGCACAGCCA CATTCCCCCC CGGCGGCGCC         1920
CCTAGCGCTG CGCCGGGGGA GGTGGCGGCC TTTTGCAGTG         1960
CCCTTTATAG ATATAATAGG TTCACCCAGC GGCATTCGCT         2000
GACCGGTGGG TTATGGCTAC ACCCTGAGGG ATTGCTGGGC         2040
ATCTTCCCCC CTTTCTCCCC TGGGCACATT TGGGAGCCTG         2080
CTAACCCTTT CTGCGGGGAG GGGACTTTGT ATACCCGGAC         2120
TTGGTCAACA TCTGGCTTTT CTAGCGATTT CTCCCCCCCT         2160
GAGGCGGCCG CCCCCGTTTT GGCCGCTGCC CCGGGGCTGC         2200
CCCACCCTAC CCCACCTGTT AGTGACATTT GGGTGTTACC         2240
ACCACCTTCA AAGGAGTCTC AGGTCGATGC GGCATCTGTG         2280
CCCCCTGCTC CTGAGCCCGC TGGATTACCC AGCTCCATTG         2320
TGCTTACCCT CCCCCCCCCC CTCCCTCCTG TGCGTAAGCC         2360
ACCAACACCC CCGCCTTCCC GCACTCGTCG TCTCCTCTAC         2400
ACCTATCCCG ACGGCGCAAA GGTGTATGCG GGTCATTGT          2440
TTGAATCAGA CTGTAACTGG CTGGTTAATG CCTCAAACCC         2480
GGGCCACCGC CCTGGAGGTG GCCTCTGCCA TGCTTTTTAC         2520
CAACGTTTCC CAGAGGCGTT TTACCCGACT GAGTTCATTA         2560
TGCGTGAGGG CCTTGCAGCA TATACCCTGA CCCCGCGCCC         2600
TATCATTCAT GCAGTGGCCC CCGACTATAG GGTTGAGCAG         2640
AATCCGAAGA GGCTTGAGGC AGCGTACCGG GAGACTTGCT         2680
CCCGTCGTGG CACCGCCGCC TACCCGCTTC TAGGCTCGGG         2720
TATATACCAG GTCCCTGTCA GCCTCAGTTT TGATGCCTGG         2760
GAACGCAATC ACCGCCCCGG CGATGAGCTT TATTTGACTG         2800
AGCCCGCCGC AGCCTGGTTC GAGGCTAATA AGCCGGCGCA         2840
GCCGGCGCTT ACTATAACTG AGGACACAGC CCGTACGGCC         2880
AACCTAGCGT TAGAGATCGA TGCTGCCACA GATGTTGGCC         2920
GTGCTTGTGC CGGCTGCACT ATCAGTCCTG GGATTGTGCA         2960
CTATCAGTTC ACTGCCGGGG TCCCAGGCTC GGGCAAGTCT         3000
CGGTCCATAC AACAGGGAGA TGTCGATGTG GTGGTCGTGC         3040
CCACCCGGGA GCTCCGTAAT AGTTGGCGTC GCCGGGGTTT         3080
TGCGGCTTTC ACACCTCACA CAGCAGCCCG TGTCACTATC         3120
GGTCGCCGCG TTGTGATTGA TGAGGCTCCA TCTCTCCCTC         3160
CACACCTGTT GCTGTTACAC ATGCAGCGGG CCTCCTCGGT         3200
CCATCTCCTT GGTGACCCAA ATCAGATCCC TGCCATTGAT         3240
TTTGAACACG CCGGCCTGGT TCCCGCGATC CGCCCTGAGC         3280
TTGCTCCAAC GAGCTGGTGG CACGTTACAC ACCGTTGCCC         3320
GGCCGATGTA TGCGAGCTCA TACGCGGAGC CTACCCTAAA         3360
ATCCAGACCA CGAGCCGTGT GCTGCGGTCC CTGTTCTGGA         3400
ACGAACCTGC TATCGGCCAG AAGTTGGTCT TCACGCAGGC         3440
TGCTAAAGCT GCTAACCCTG GTGCGATTAC GGTTCATGAA         3480
GCTCAGGGTG CCACTTTTAC AGAGACCACA ATTATAGCCA         3520
CGGCCGATGC CAGGGGCCTT ATCCAGTCAT CCCGGGCTCA         3560
CGCTATAGTC GCACTCACCC GCCACACTGA GAAGTGTGTT         3600
ATTCTGGATG CTCCCGGCCT GCTGCGTGAG GTCGGCATTT         3640
CGGATGTGAT TGTCAATAAC TTTTTCCTTG CTGGCGGAGA         3680
AGTCGGCCAT CACCGCCCTT CTGTGATACC CCGCGGTAAC         3720
CCTGATCAGA ACCTCGGGAC TCTACAGGCC TTCCCGCCGT         3760
```

FIG. 7B

| | | | | |
|---|---|---|---|---|
| CCTGCCAGAT | TAGTGCTTAC | CACCAATTGG | CTGAAGAATT | 3800 |
| AGGCCACCGT | CCGGCTCCTG | TTGCCGCCGT | CTTGCCCCCT | 3840 |
| TGCCCTGAGC | TTGAGCAGGG | CCTGCTCTAT | ATGCCACAAG | 3880 |
| AGCTTACTGT | GTCTGATAGT | GTGTTGGTTT | TTGAGCTCAC | 3920 |
| GGATATAGTC | CACTGTCGCA | TGGCCGCTCC | GAGCCAGCGA | 3960 |
| AAGGCTGTTC | TCTCAACACT | TGTAGGGAGA | TACGGCCGTA | 4000 |
| GGACGAAATT | ATATGAGGCA | GCGCATTCAG | ATGTTCGTGA | 4040 |
| GTCCCTGGCC | AGGTTCATTC | CCACTATCGG | GCCTGTTCAG | 4080 |
| GCCACCACAT | GTGAGTTGTA | TGAGTTGGTT | GAGGCCATGG | 4120 |
| TGGAGAAGGG | ACAGGACGGC | TCTGCCGTCC | TAGAGCTTGA | 4160 |
| CCTTTGCAAT | CGTGACGTAT | CGCGCATCAC | ATTTTTCCAA | 4200 |
| AAGGATTGCA | ACAAGTTTAC | AACTGGTGAG | ACTATCGCCC | 4240 |
| ATGGCAAGGT | TGGTCAGGGT | ATATCGGCCT | GGAGTAAGAC | 4280 |
| CTTCTGTGCT | CTGTTTGGCC | CGTGGTTCCG | TGCCATTGAA | 4320 |
| AAAGAAATAC | TGGCCCTACT | CCCGCCTAAT | ATCTTTTATG | 4360 |
| GCGACGCCTA | TGAGGAATCA | GTGTTCGCTG | CCGCTGTGTC | 4400 |
| CGGGGCGGGG | TCGTGCATGG | TATTTGAAAA | TGACTTTTCA | 4440 |
| GAGTTTGACA | GTACCCAAAA | TAATTTCTCC | CTTGGCCTTG | 4480 |
| AGTGTGTGGT | TATGGAGGAG | TGCGGCATGC | CCCAGTGGCT | 4520 |
| AATTAGGTTG | TATCATCTGG | TTCGGTCAGC | CTGGATTTTG | 4560 |
| CAGGCGCCGA | AGGAGTCTCT | TAAGGGTTTC | TGGAAGAAGC | 4600 |
| ATTCTGGTGA | GCCTGGTACC | CTTCTCTGGA | ACACCGTCTG | 4640 |
| GAACATGGCG | ATTATAGCAC | ATTGTTATGA | GTTTCGTGAC | 4680 |
| TTTCGTGTTG | CCGCCTTCAA | GGGTGATGAT | TCAGTGGTCC | 4720 |
| TTTGTAGTGA | CTACCGACAG | AGCCGTAATG | CGGCTGCCTT | 4760 |
| AATTGCAGGC | TGTGGGCTCA | AATTGAAGGT | TGACTACCGC | 4800 |
| CCTATTGGGC | TGTATGCCGG | GGTGGTGGTG | GCCCCTGGTC | 4840 |
| TGGGGACACT | GCCTGATGTT | GTGCGTTTCG | CCGGTCGGTT | 4880 |
| GTCTGAAAAG | AATTGGGGCC | CCGGCCCAGA | GCGTGCTGAG | 4920 |
| CAGCTGCGTC | TTGCTGTTTG | TGACTTCCTT | CGAGGGTTGA | 4960 |
| CAAATGTTGC | GCAGGTTTGT | GTTGATGTTG | TGTCCCGTGT | 5000 |
| TTATGGAGTT | AGCCCCGGGC | TGGTGCATAA | CCTTATTGGC | 5040 |
| ATGCTGCAGA | CTATTGCCGA | TGGCAAGGCC | CACTTTACAG | 5080 |
| AGACTATTAA | ACCTGTGCTT | GACCTTACAA | ACTCTATCAT | 5120 |
| ACAGCGGGTG | GAATGAATAA | CATGTCTTTT | GCATCGCCCA | 5160 |
| TGGGATCACC | ATGCGCCCTA | GGGCTGTTCT | GTTGTTGCTC | 5200 |
| TTCGTGCTTC | TGCCTATGCT | GCCCGCGCCA | CCGGCCGGCC | 5240 |
| AGCCGTCTGG | CCGCCGTTGT | GGGCGGCGCA | ACGGCGGTGC | 5280 |
| CGGCGGTGG | TTCTGGGGTG | ACAGGGTTGA | TTCTCAGCCC | 5320 |
| TTCGCCCTCC | CCTATATTCA | TCCAACCAAC | CCCTTCGCTG | 5360 |
| CCGATGTCGT | TTCACAACCC | GGGGCTGGAG | TTCGCCCTCG | 5400 |
| ACAGCCGCCC | CGCCCCCTTG | GCTCCGCTTG | GCGTGACCAG | 5440 |
| TCCCAGCGCC | CCTCCACTGC | CCCCGTCGT | CGATCTGCCC | 5480 |
| CAGCTGGGGC | TGCGCCGCTG | ACTGCTGTAT | CACCGGCCCC | 5520 |
| CGACACAGCT | CCTGTACCTG | ATGTTGACTC | ACGTGGTGCT | 5560 |
| ATCCTGCGCC | GGCAGTACAA | TCTGTCTACG | TCCCCGCTCA | 5600 |
| CGTCATCTGT | CGCTGCTGGT | ACCAACCTGG | TTCTCTATGC | 5640 |

FIG. 7C

```
CGCCCCGCTG AATCCTCTCT TGCCCCTCCA GGATGGCACC         5680
AACACTCATA TTATGGCTAC TGAGGCGTCC AATTATGCTC         5720
AGTATCGGGT TGTTCGAGCT ACGATCCGTT ATCGCCCGCT         5760
GGTGCCAAAT GCTGTTGGTG GCTATGCTAT CTCTATTTCT         5800
TTCTGGCCTC AAACTACAAC CACCCCTACT TCAGTTGACA         5840
TGAACTCTAT TACCTCCACT GATGTCAGGA TTTTGGTTCA         5880
GCCCGGTATT GCCTCCGAGT TAGTCATCCC TAGTGAGCGC         5920
CTTCATTACC GCAATCAAGG CTGGCGCTCT GTAGAGACCA         5960
CGGGCGTGGC CGAGGAGGAA GCTACCTCCG GTCTGGTAAT         6000
GCTTTGCATT CACGGTTCTC CTGTTAACTC CTATACTAAC         6040
ACACCTTACA CTGGTGCATT GGGGCTCCTT GATTTGCAT         6080
TAGAGCTTGA ATTCAGAAAT TTGACACCCG GAACACTAA         6120
CACCCGTGTT TCCCGGTACA CCAGCACAGC CCGCCATCGG         6160
CTGCGCCGCG GTGCTGATGG GACCGCAGAG CTTACCACCA         6200
CAGCAGCCAC ACGTTTCATG AAGGACTTGC ATTTCACCGG         6240
CACGAACGGC GTTGGTGAGG TGGGTCGCGG TATAGCTCTA         6280
ACACTGTTTA ACCTTGCTGA TACGTTCTT GGTGGTTTAC          6320
CGACAGAATT GATTTCGTCG GCCGGGGCC AACTGTTTTA          6360
CTCCCGCCCT GTCGTCTCGG CCAATGGCGA GCCGACGGTT         6400
AAGTTATATA CATCTGTTGA GAATGCGCAG CAGGACAAGG         6440
GCATTACCAT CCCACACGAT ATAGATCTGG GTGATTCCCG         6480
TGTGGTTATT CAGGATTATG ATAACCAGCA CGAGCAAGAC         6520
CGACCTACTC CGTCACCAGC CCCCTCTCGC CCTTTCTCAG         6560
TTCTTCGCGC CAATGATGTT CTGTGGCTCT CCCTCACCGC         6600
CGCTGAGTAC GATCAGACTA CATATGGGTC GTCCACCAAC         6640
CCTATGTATG TCTCCGATAC GGTCACGCTA GTTAATGTGG         6680
CCACTGGTGC TCAGGCTGTT GCCCGCTCTC TTGATTGGTC         6720
TAAAGTCACT CTGGATGGCC GCCCCCTCAC TACCATTCAG         6760
CAGTATTCAA AGACATTCTA TGTTCTCCCG CTCCGCGGGA         6800
AGCTGTCCTT TTGGGAGGCT GGTACCACTA AGGCCGGCTA         6840
CCCGTATAAT TATAATACCA CTGCTAGTGA TCAAATTTTG         6880
ATTGAGAACG CGGCTGGCCA CCGTGTTGCT ATCTCTACCT         6920
ATACCACTAG CTTGGGTGCC GGCCCTACCT CGATTTCCGC         6960
CGTTGGTGTG CTAGCCCCAC ACTCGGCTCT CGCCGTCCTT         7000
GAGGATACTG TTGATTACCC TGCTCGTGCT CATACTTTTG         7040
ATGATTTCTG CCCGGAGTGC CGCACCCTTG GTTTGCAGGG         7080
TTGTGCATTC CAGTCTACTA TTGCTGAGCT TCAGCGTCTT         7120
AAAATGAAGG TAGGTAAAAC CCGGGAGTCT TAATTAATTC         7160
CTTTTGTGCC CCCTTCATAG CTTCCTTTGG TTTTATTTCT         7200
TATTTCT                                             7201
```

FIG. 7D

A32-33
forward, 5'-ATATGTGGTCGATGCCATGGAG-3'; reverse, 5'-CTCGGGCAGTACTGTTCCAGTTC-3'
forward, 5'-TCGATGCCATGGAGGAGGCCCATCA-3'; reverse, 5'-GTATTGCCCGCTGGATAGGATG-3'

3487-88
forward, 5'-AAGGCTCC(A)TGGCATCACTACTG-3'; reverse, 5'-CAGAGGCA(G)TTCCAGCCTTCATT-3'
forward, 5'-TGGCATCACTACTGC(T)TATTGAG-3'; reverse, 5'-GGGAGCAGCAAAAGGCT(C)TGGTC-3'

F6-F5
forward, 5'-TCTACATTTCATGCTGTCCCGGTTCATA-3'; reverse, 5'-TCCTGACCAAGCCACTTCAT-3'
forward, 5'-GATGACCAAGCCTTTGCTG-3'; reverse, 5'-TAATCACGGCCGGACTTCTC-3'

BRL3-4
forward, 5'-TGCCATCAGCGTTATCTTCGCACCCA-3'; reverse, 5'-GCACGGCCAACATCTGTGGCAGCATC-3'
forward, 5'-ACCCAGGCGATATCCAAGGGCATGCG-3'; reverse, 5'-GCATCGATCTCTAACGCTAGGTTGGC-3'

G4G8
forward, 5'-TATA(C)GG(A)TTGGAACATAACCC-3'; reverse, 5'-CGGTGTGTAACGTGCCACCA-3'
forward, 5'-TTT(C)GAC(T)GCCTGGGAGCGGAA-3'; reverse, 5'-AAATCAATGGCAGGGATCTG-3'

3506-7
forward, 5'-GGCGC(T)C(A)GGGTTGTCATTGATGA-3'; reverse, 5'-GGGAGTAGGGCCAGTATTCTT-3'
forward, 5'-TTGGC(T)GACCCGAAT(C)CAGATCCC-3'; reverse, 5'-CTTTTTCAATGGCACGGAACCA-3'

3154-77
forward, 5'-GAGGCC(G)ATGGTC(G)GAGAAGGGCCA-3'; reverse, 5'-AAGAGCAACAACAGAACAGCCC-3'
forward, 5'-ACCTTC(T)TTCCAGAAA(G)GATTGTAA-3'; reverse, 5'-CTAGGGGCGCATGGTGATCCCAT-3'

3479-77
forward, 5'-CTGGAAGAAA(G)CAC(T)TCT(C)GGTGAG-3'; reverse, 5'-AAGAGCAACAACAGAACAGCCC-3'
forward, 5'-TGGAATACT(G)GTC(G)TGGAAC(T)ATGG-3'; reverse, 5'-CTAGGGCGCATGGTGATCCCAT-3'

3301-2
forward, 5'-CTCAGTTCTTCGCGCCAATGAT-3'; reverse, 5'-TTTTTTCAGGGAGGCGCGGG(A)AC-3'

FIG. 8B

SEQUENCE LISTING

<160> NUMBER OF SEQ ID NOS: 65

<210> SEQ ID NO 1
<211> LENGTH: 5127
<212> TYPE: DNA
<213> ORGANISM: Hepatitis E virus

<400> SEQUENCE: 1

```
atggaggccc atcagttcat taaggctcct ggcattacta ctgccattga gcaggctgct     60
ctggctgcgg ccaactccgc cttggcgaat gctgtggtgg ttcggccgtt tttatctcgt    120
gtacaaactg agatccttat taatttgatg caacccggc agttggtttt ccgccctgag     180
gtactttgga atcatcctat ccagcgggca atacataatg aactggaaca gtactgccga    240
gcccgggctg gttgttgttt ggaagttgga gcccatccga gatttattaa tgacaatccc    300
aacgtcctgc accggtgctt ccttagaccg gttggccgag atgtccagcg ctggtactct    360
gcccccaccc gtggccctgc ggccaattgt cgccgctccg cgctgcgtgg ccttcccccc    420
gtcgaccgca cttactgttt tgatggattc tctcgttgtg ctttcgctgc agagaccggt    480
gtggccctct actctttaca tgacctttgg ccagctgatg ttgcggaggc tatggcccgc    540
cacgggatga cacgcctata cgccgcactg caccttcttc ccgaggtgct gctaccaccc    600
ggcacctacc acacaacttc gtacctcctg attcacgacg gtgaccgcgc tgttgtgact    660
tatgagggcg atactagtgc gggctataac catgatgtct ccatactccg tgcgtggatc    720
cgtaccacta aaatagttgg tgaccacccg ttggttatag agcgtgtgcg ggccattggc    780
tgtcattttg tgctgctgct caccgcagcc cctgaaccgt cacctatgcc ttatgtcccc    840
taccctcgtt caacggaggt gtatgttcga tccatatttg gccctggcgg ctccccatcc    900
ttgtttccgt cagcctgctc tactaaatct acatttcatg ctgtcccggt tcatatctgg    960
```

```
gatcggctca tgcttttggg tgccaccctg gatgaccagg ccttttgttg ttcacggctc   1020
atgacctacc tccgtggtat tagctacaag gtcactgtcg gtgcgcttgt cgctaatgag   1080
gggtggaacg cctctgaaga tgctcttact gcagtgatta ctgccgctta tctgactatt   1140
tgccatcagc gttatcttcg cacccaggcg atatccaagg gcatgcgccg gctggaggtt   1200
gagcacgccc agaaatttat cacaagactt tacagttggc tatttgagaa gtctggccgt   1260
gattatatcc ccggccgtca gcttcagttc tacgcacagt gccggcggtg gttatctgca   1320
ggcttccacc tagaccccag ggtgcttgtt tttgatgaat cagtgccatg ccgctgcagg   1380 acgttttga agaaagtcgc aggtaagttc tgctgttta tgcggtggtt agggcaggag    1440
tgtacctgtt tcttggagcc agccgaaggc ttggttggcg actatggcca tgacaacgag   1500
gcctatgagg gttctgaggt cgacccggct gaacctgctc atcttgatgt ttctgggacc   1560
tatgccgttc acgggcgcca gcttgaggct ctctataggg cacttaatgt cccacatgac   1620
atcgccgctc gagcctcccg cctaacggct actgttgagc tcactgcaag cccagaccgt   1680
ttagagtgcc gcactgtgct tggtaataag accttcagga cgacggtggt tgatggcgcc   1740
catcttgagg cgaatggtcc tgagcagtat gtcctatcat tcgacgcctc ccgccagtct   1800
atgggggccg ggtcacatag cctcacttat gagctcaccc ctgccggcct gcaggtcagg   1860
atttcatcta atggcctgga ttgcacagcc acattccccc ccggcggcgc ccctagcgct   1920
gcgccggggg aggtggcggc cttttgcagt gccctttata gataataag gttcacccag    1980 cggcattcgc tgaccggtgg gttatggcta cacctgagg gattgctggg catcttcccc    2040
cctttctccc ctgggcacat tgggagcct gctaacccct tctgcgggga ggggacttg     2100 tatacccgga cttggtcaac atctggcttt tctagcgatt tctccccccc tgaggcggcc   2160
gccccgtttt tggccgctgc cccggggctg cccccaccct accccacctgt tagtgacatt  2220 tgggtgttac caccaccttc aaaggagtct caggtcgatg cggcatctgt gccccctgct   2280
cctgagcccg ctggattacc cagctccatt gtgcttaccc tccccccccc cctccctcct   2340
gtgcgtaagc caccaacacc cccgccttcc cgcactcgtc gtctcctcta cacctatccc   2400
gacggcgcaa aggtgtatgc gggtcattg tttgaatcag actgtaactg ctggttaat     2460 gcctcaaacc cgggccaccg ccctggaggt ggcctctgcc atgctttta ccaacgtttc    2520 ccagaggcgt tttacccgac tgagttcatt atgcgtgagg gccttgcagc atataccctg   2580
accccgcgcc ctatcattca tgcagtggcc cccgactata gggttgagca gaatccgaag   2640
aggcttgagg cagcgtaccg ggagacttgc tcccgtcgtg gcaccgccgc ctacccgctt   2700
ctaggctcgg gtatatacca ggtccctgtc agcctcagtt ttgatgcctg ggaacgcaat   2760
caccgccccg gcgatgagct ttatttgact gagcccgccg cagcctggtt cgaggctaat   2820
aagccggcgc agccggcgct tactataact gaggacacag cccgtacggc caacctagcg   2880
ttagagatcg atgctgccac agatgttggc cgtgcttgtg ccggctgcac tatcagtcct   2940
gggattgtgc actatcagtt cactgccggg gtcccaggct cgggcaagtc tcggtccata   3000
caacagggag atgtcgatgt ggtggtcgtg cccacccggg agctccgtaa tagttggcgt   3060 cgccgggtt ttgcggcttt cacacctcac acagcagccc gtgtcactat cggtcgccgc    3120
gttgtgattg atgaggctcc atctctccct ccacacctgt tgctgttaca catgcagcgg   3180
gcctcctcgg tccatctcct tggtgaccca aatcagatcc ctgccattga ttttgaacac   3240
gccggcctgg ttcccgcgat ccgccctgag cttgctccaa cgagctggtg gcacgttaca   3300
```

-continued

```
caccgttgcc cggccgatgt atgcgagctc atacgcggag cctaccctaa atccagacc    3360
acgagccgtg tgctgcggtc cctgttctgg aacgaacctg ctatcggcca gaagttggtc    3420
ttcacgcagg ctgctaaagc tgctaaccct ggtgcgatta cggttcatga agctcagggt    3480
gccacttta cagagaccac aattatagcc acggccgatg ccaggggcct atccagtca     3540
tcccgggctc acgctatagt cgcactcacc cgccacactg agaagtgtgt tattctggat    3600
gctcccggcc tgctgcgtga ggtcggcatt tcggatgtga ttgtcaataa cttttttcctt   3660
gctggcggaa agtcggcca tcaccgcccct ctgtgatac cccgcggtaa ccctgatcag    3720
aacctcggga ctctacaggc cttcccgccg tcctgccaga ttagtgctta ccaccaattg    3780
gctgaagaat taggccaccg tccggctcct gttgccgccg tcttgccccc ttgccctgag    3840
cttgagcagg gcctgctcta tgccacaa gagcttactg tgtctgatag tgtgttggtt     3900
tttgagctca cggatatagt ccactgtcgc atggccgctc cgagccagcg aaaggctgtt    3960
ctctcaacac ttgtagggag atacggccgt aggacgaaat tatatgaggc agcgcattca    4020
gatgttcgtg agtccctggc caggttcatt cccactatcg ggcctgttca ggccaccaca    4080
tgtgagttgt atgagttggt tgaggccatg gtggagaagg acaggacgg ctctgccgtc     4140
ctagagcttg acctttgcaa tcgtgacgta tcgcgcatca catttttccca aaaggattgc    4200
aacaagttta caactggtga gactatcgcc catggcaagg ttggtcaggg tatatcggcc    4260
tggagtaaga ccttctgtgc tctgtttggc ccgtggttcc gtgccattga aaagaaata     4320
ctggccctac tccccgcctaa tatcttttat ggcgacgcct atgaggaatc agtgttcgct   4380
gccgctgtgt ccggggcggg gtcgtgcatg gtatttgaaa atgacttttc agagtttgac   4440
agtacccaaa ataatttctc ccttggcctt gagtgtgtgg ttatggagga gtgcggcatg   4500
ccccagtggc taattaggtt gtatcatctg gttcggtcag cctggattt gcaggcgccg    4560
aaggagtctc ttaagggttt ctggaagaag cattctggtg agcctggtac ccttctctgg    4620
aacaccgtct ggaacatggc gattatagca cattgttatg agttttcgtga ctttcgtgtt   4680
gccgccttca aggtgatga ttcagtggtc cttttgtagtg actaccgaca gagccgtaat    4740
gcggctgcct taattgcagg ctgtgggctc aaattgaagg ttgactaccg ccctattggg    4800
ctgtatgccg gggtggtggt ggccctggt ctggggacac tgcctgatgt tgtgcgtttc    4860
gccggtcggt tgtctgaaaa gaattgggc cccggcccag agcgtgctga gcagctgcgt    4920
cttgctgttt gtgacttcct tcgagggttg acaaatgttg cgcaggtttg tgttgatgtt   4980
gtgtcccgtg tttatggagt tagcccccggg ctggtgcata accttattgg catgctgcag   5040
actattgccg atggcaaggc ccactttaca gagactatta aacctgtgct tgaccttaca   5100
aactctatca tacagcgggt ggaatga                                         5127
```

<210> SEQ ID NO 2
<211> LENGTH: 1708
<212> TYPE: PRT
<213> ORGANISM: Hepatitis E virus

<400> SEQUENCE: 2

```
Met Glu Ala His Gln Phe Ile Lys Ala Pro Gly Ile Thr Thr Ala Ile
  1               5                  10                  15

Glu Gln Ala Ala Leu Ala Ala Ala Asn Ser Ala Leu Ala Asn Ala Val
             20                  25                  30

Val Val Arg Pro Phe Leu Ser Arg Val Gln Thr Glu Ile Leu Ile Asn
         35                  40                  45
```

-continued

```
Leu Met Gln Pro Arg Gln Leu Val Phe Arg Pro Glu Val Leu Trp Asn
     50                  55                  60
His Pro Ile Gln Arg Ala Ile His Asn Glu Leu Glu Gln Tyr Cys Arg
 65                  70                  75                  80
Ala Arg Ala Gly Cys Cys Leu Glu Val Gly Ala His Pro Arg Phe Ile
                 85                  90                  95
Asn Asp Asn Pro Asn Val Leu His Arg Cys Phe Leu Arg Pro Val Gly
             100                 105                 110
Arg Asp Val Gln Arg Trp Tyr Ser Ala Pro Thr Arg Gly Pro Ala Ala
         115                 120                 125
Asn Cys Arg Arg Ser Ala Leu Arg Gly Leu Pro Pro Val Asp Arg Thr
     130                 135                 140
Tyr Cys Phe Asp Gly Phe Ser Arg Cys Ala Phe Ala Ala Glu Thr Gly
145                 150                 155                 160
Val Ala Leu Tyr Ser Leu His Asp Leu Trp Pro Ala Asp Val Ala Glu
                 165                 170                 175
Ala Met Ala Arg His Gly Met Thr Arg Leu Tyr Ala Ala Leu His Leu
             180                 185                 190
Leu Pro Glu Val Leu Pro Pro Gly Thr Tyr His Thr Thr Ser Tyr
         195                 200                 205
Leu Leu Ile His Asp Gly Asp Arg Ala Val Val Thr Tyr Glu Gly Asp
     210                 215                 220
Thr Ser Ala Gly Tyr Asn His Asp Val Ser Ile Leu Arg Ala Trp Ile
225                 230                 235                 240
Arg Thr Thr Lys Ile Val Gly Asp His Pro Leu Val Ile Glu Arg Val
                 245                 250                 255
Arg Ala Ile Gly Cys His Phe Val Leu Leu Thr Ala Ala Pro Glu
             260                 265                 270
Pro Ser Pro Met Pro Tyr Val Pro Tyr Pro Arg Ser Thr Glu Val Tyr
         275                 280                 285
Val Arg Ser Ile Phe Gly Pro Gly Ser Pro Ser Leu Phe Pro Ser
     290                 295                 300
Ala Cys Ser Thr Lys Ser Thr Phe His Ala Val Pro Val His Ile Trp
305                 310                 315                 320
Asp Arg Leu Met Leu Phe Gly Ala Thr Leu Asp Gln Ala Phe Cys
                 325                 330                 335
Cys Ser Arg Leu Met Thr Tyr Leu Arg Gly Ile Ser Tyr Lys Val Thr
             340                 345                 350
Val Gly Ala Leu Val Ala Asn Glu Gly Trp Asn Ala Ser Glu Asp Ala
         355                 360                 365
Leu Thr Ala Val Ile Thr Ala Ala Tyr Leu Thr Ile Cys His Gln Arg
     370                 375                 380
Tyr Leu Arg Thr Gln Ala Ile Ser Lys Gly Met Arg Arg Leu Glu Val
385                 390                 395                 400
Glu His Ala Gln Lys Phe Ile Thr Arg Leu Tyr Ser Trp Leu Phe Glu
                 405                 410                 415
Lys Ser Gly Arg Asp Tyr Ile Pro Gly Arg Gln Leu Gln Phe Tyr Ala
             420                 425                 430
Gln Cys Arg Arg Trp Leu Ser Ala Gly Phe His Leu Asp Pro Arg Val
         435                 440                 445
Leu Val Phe Asp Glu Ser Val Pro Cys Arg Cys Arg Thr Phe Leu Lys
     450                 455                 460
Lys Val Ala Gly Lys Phe Cys Cys Phe Met Arg Trp Leu Gly Gln Glu
```

```
465                 470                 475                 480
Cys Thr Cys Phe Leu Glu Pro Ala Glu Gly Leu Val Gly Asp Tyr Gly
                    485                 490                 495
His Asp Asn Glu Ala Tyr Glu Gly Ser Glu Val Asp Pro Ala Glu Pro
                    500                 505                 510
Ala His Leu Asp Val Ser Gly Thr Tyr Ala Val His Gly Arg Gln Leu
                    515                 520                 525
Glu Ala Leu Tyr Arg Ala Leu Asn Val Pro His Asp Ile Ala Ala Arg
                    530                 535                 540
Ala Ser Arg Leu Thr Ala Thr Val Glu Leu Thr Ala Ser Pro Asp Arg
545                 550                 555                 560
Leu Glu Cys Arg Thr Val Leu Gly Asn Lys Thr Phe Arg Thr Thr Val
                    565                 570                 575
Val Asp Gly Ala His Leu Glu Ala Asn Gly Pro Glu Gln Tyr Val Leu
                    580                 585                 590
Ser Phe Asp Ala Ser Arg Gln Ser Met Gly Ala Gly Ser His Ser Leu
                    595                 600                 605
Thr Tyr Glu Leu Thr Pro Ala Gly Leu Gln Val Arg Ile Ser Ser Asn
                    610                 615                 620
Gly Leu Asp Cys Thr Ala Thr Phe Pro Pro Gly Gly Ala Pro Ser Ala
625                 630                 635                 640
Ala Pro Gly Glu Val Ala Ala Phe Cys Ser Ala Leu Tyr Arg Tyr Asn
                    645                 650                 655
Arg Phe Thr Gln Arg His Ser Leu Thr Gly Gly Leu Trp Leu His Pro
                    660                 665                 670
Glu Gly Leu Leu Gly Ile Phe Pro Pro Phe Ser Pro Gly His Ile Trp
                    675                 680                 685
Glu Pro Ala Asn Pro Phe Cys Gly Glu Gly Thr Leu Tyr Thr Arg Thr
                    690                 695                 700
Trp Ser Thr Ser Gly Phe Ser Ser Asp Phe Ser Pro Pro Glu Ala Ala
705                 710                 715                 720
Ala Pro Val Leu Ala Ala Pro Gly Leu Pro His Pro Thr Pro Pro
                    725                 730                 735
Val Ser Asp Ile Trp Val Leu Pro Pro Pro Ser Lys Glu Ser Gln Val
                    740                 745                 750
Asp Ala Ala Ser Val Pro Pro Ala Pro Glu Pro Ala Gly Leu Pro Ser
                    755                 760                 765
Ser Ile Val Leu Thr Leu Pro Pro Pro Leu Pro Pro Val Arg Lys Pro
770                 775                 780
Pro Thr Pro Pro Pro Ser Arg Thr Arg Arg Leu Leu Tyr Thr Tyr Pro
785                 790                 795                 800
Asp Gly Ala Lys Val Tyr Ala Gly Ser Leu Phe Glu Ser Asp Cys Asn
                    805                 810                 815
Trp Leu Val Asn Ala Ser Asn Pro Gly His Arg Pro Gly Gly Gly Leu
                    820                 825                 830
Cys His Ala Phe Tyr Gln Arg Phe Pro Glu Ala Phe Tyr Pro Thr Glu
                    835                 840                 845
Phe Ile Met Arg Glu Gly Leu Ala Ala Tyr Thr Leu Thr Pro Arg Pro
                    850                 855                 860
Ile Ile His Ala Val Ala Pro Asp Tyr Arg Val Glu Gln Asn Pro Lys
865                 870                 875                 880
Arg Leu Glu Ala Ala Tyr Arg Glu Thr Cys Ser Arg Arg Gly Thr Ala
                    885                 890                 895
```

```
Ala Tyr Pro Leu Leu Gly Ser Gly Ile Tyr Gln Val Pro Val Ser Leu
            900                 905                 910
Ser Phe Asp Ala Trp Glu Arg Asn His Arg Pro Gly Asp Glu Leu Tyr
        915                 920                 925
Leu Thr Glu Pro Ala Ala Ala Trp Phe Glu Ala Asn Lys Pro Ala Gln
    930                 935                 940
Pro Ala Leu Thr Ile Thr Glu Asp Thr Ala Arg Thr Ala Asn Leu Ala
945                 950                 955                 960
Leu Glu Ile Asp Ala Ala Thr Asp Val Gly Arg Ala Cys Ala Gly Cys
                965                 970                 975
Thr Ile Ser Pro Gly Ile Val His Tyr Gln Phe Thr Ala Gly Val Pro
            980                 985                 990
Gly Ser Gly Lys Ser Arg Ser Ile Gln Gln Gly Asp Val Asp Val Val
        995                 1000                1005
Val Val Pro Thr Arg Glu Leu Arg Asn Ser Trp Arg Arg Gly Phe
    1010                1015                1020
Ala Ala Phe Thr Pro His Thr Ala Ala Arg Val Thr Ile Gly Arg Arg
1025                1030                1035                1040
Val Val Ile Asp Glu Ala Pro Ser Leu Pro Pro His Leu Leu Leu Leu
                1045                1050                1055
His Met Gln Arg Ala Ser Ser Val His Leu Leu Gly Asp Pro Asn Gln
            1060                1065                1070
Ile Pro Ala Ile Asp Phe Glu His Ala Gly Leu Val Pro Ala Ile Arg
        1075                1080                1085
Pro Glu Leu Ala Pro Thr Ser Trp Trp His Val Thr His Arg Cys Pro
    1090                1095                1100
Ala Asp Val Cys Glu Leu Ile Arg Gly Ala Tyr Pro Lys Ile Gln Thr
1105                1110                1115                1120
Thr Ser Arg Val Leu Arg Ser Leu Phe Trp Asn Glu Pro Ala Ile Gly
                1125                1130                1135
Gln Lys Leu Val Phe Thr Gln Ala Ala Lys Ala Ala Asn Pro Gly Ala
            1140                1145                1150
Ile Thr Val His Glu Ala Gln Gly Ala Thr Phe Thr Glu Thr Thr Ile
        1155                1160                1165
Ile Ala Thr Ala Asp Ala Arg Gly Leu Ile Gln Ser Ser Arg Ala His
    1170                1175                1180
Ala Ile Val Ala Leu Thr Arg His Thr Glu Lys Cys Val Ile Leu Asp
1185                1190                1195                1200
Ala Pro Gly Leu Leu Arg Glu Val Gly Ile Ser Asp Val Ile Val Asn
                1205                1210                1215
Asn Phe Phe Leu Ala Gly Gly Glu Val Gly His His Arg Pro Ser Val
            1220                1225                1230
Ile Pro Arg Gly Asn Pro Asp Gln Asn Leu Gly Thr Leu Gln Ala Phe
        1235                1240                1245
Pro Pro Ser Cys Gln Ile Ser Ala Tyr His Gln Leu Ala Glu Glu Leu
    1250                1255                1260
Gly His Arg Pro Ala Pro Val Ala Ala Val Leu Pro Pro Cys Pro Glu
1265                1270                1275                1280
Leu Glu Gln Gly Leu Leu Tyr Met Pro Gln Glu Leu Thr Val Ser Asp
                1285                1290                1295
Ser Val Leu Val Phe Glu Leu Thr Asp Ile Val His Cys Arg Met Ala
            1300                1305                1310
```

```
Ala Pro Ser Gln Arg Lys Ala Val Leu Ser Thr Leu Val Gly Arg Tyr
    1315                1320                1325

Gly Arg Arg Thr Lys Leu Tyr Glu Ala Ala His Ser Asp Val Arg Glu
1330                1335                1340

Ser Leu Ala Arg Phe Ile Pro Thr Ile Gly Pro Val Gln Ala Thr Thr
1345                1350                1355                1360

Cys Glu Leu Tyr Glu Leu Val Glu Ala Met Val Glu Lys Gly Gln Asp
            1365                1370                1375

Gly Ser Ala Val Leu Glu Leu Asp Leu Cys Asn Arg Asp Val Ser Arg
        1380                1385                1390

Ile Thr Phe Phe Gln Lys Asp Cys Asn Lys Phe Thr Thr Gly Glu Thr
    1395                1400                1405

Ile Ala His Gly Lys Val Gly Gln Gly Ile Ser Ala Trp Ser Lys Thr
1410                1415                1420

Phe Cys Ala Leu Phe Gly Pro Trp Phe Arg Ala Ile Glu Lys Glu Ile
1425                1430                1435                1440

Leu Ala Leu Leu Pro Pro Asn Ile Phe Tyr Gly Asp Ala Tyr Glu Glu
            1445                1450                1455

Ser Val Phe Ala Ala Ala Val Ser Gly Ala Gly Ser Cys Met Val Phe
        1460                1465                1470

Glu Asn Asp Phe Ser Glu Phe Asp Ser Thr Gln Asn Asn Phe Ser Leu
    1475                1480                1485

Gly Leu Glu Cys Val Val Met Glu Glu Cys Gly Met Pro Gln Trp Leu
1490                1495                1500

Ile Arg Leu Tyr His Leu Val Arg Ser Ala Trp Ile Leu Gln Ala Pro
1505                1510                1515                1520

Lys Glu Ser Leu Lys Gly Phe Trp Lys Lys His Ser Gly Glu Pro Gly
            1525                1530                1535

Thr Leu Leu Trp Asn Thr Val Trp Asn Met Ala Ile Ile Ala His Cys
        1540                1545                1550

Tyr Glu Phe Arg Asp Phe Arg Val Ala Ala Phe Lys Gly Asp Asp Ser
    1555                1560                1565

Val Val Leu Cys Ser Asp Tyr Arg Gln Ser Arg Asn Ala Ala Ala Leu
1570                1575                1580

Ile Ala Gly Cys Gly Leu Lys Leu Lys Val Asp Tyr Arg Pro Ile Gly
1585                1590                1595                1600

Leu Tyr Ala Gly Val Val Val Ala Pro Gly Leu Gly Thr Leu Pro Asp
            1605                1610                1615

Val Val Arg Phe Ala Gly Arg Leu Ser Glu Lys Asn Trp Gly Pro Gly
        1620                1625                1630

Pro Glu Arg Ala Glu Gln Leu Arg Leu Ala Val Cys Asp Phe Leu Arg
    1635                1640                1645

Gly Leu Thr Asn Val Ala Gln Val Cys Val Asp Val Val Ser Arg Val
1650                1655                1660

Tyr Gly Val Ser Pro Gly Leu Val His Asn Leu Ile Gly Met Leu Gln
1665                1670                1675                1680

Thr Ile Ala Asp Gly Lys Ala His Phe Thr Glu Thr Ile Lys Pro Val
            1685                1690                1695

Leu Asp Leu Thr Asn Ser Ile Ile Gln Arg Val Glu
        1700                1705

<210> SEQ ID NO 3
<211> LENGTH: 7207
<212> TYPE: DNA
```

<213> ORGANISM: Hepatitis E virus

<400> SEQUENCE: 3

| | | | | | |
|---|---|---|---|---|---|
| ttcgatgcca | tggaggccca | tcagttcatt | aaggctcctg | gcattactac | tgccattgag | 60 |
| caggctgctc | tggctgcggc | caactccgcc | ttggcgaatg | ctgtggtggt | tcggccgttt | 120 |
| ttatctcgtg | tacaaactga | gatccttatt | aatttgatgc | aacccggca | gttggttttc | 180 |
| cgccctgagg | tactttggaa | tcatcctatc | cagcgggcaa | tacataatga | actggaacag | 240 |
| tactgccgag | cccgggctgg | ttgttgtttg | gaagttggag | cccatccgag | atttattaat | 300 |
| gacaatccca | acgtcctgca | ccggtgcttc | cttagaccgg | ttggccgaga | tgtccagcgc | 360 |
| tggtactctg | cccccacccg | tggccctgcg | gccaattgtc | gccgctccgc | gctgcgtggc | 420 |
| cttccccccg | tcgaccgcac | ttactgtttt | gatggattct | ctcgttgtgc | tttcgctgca | 480 |
| gagaccggtg | tggccctcta | ctctttacat | gacctttggc | cagctgatgt | tgcggaggct | 540 |
| atggcccgcc | acgggatgac | acgcctatac | gccgcactgc | accttcttcc | cgaggtgctg | 600 |
| ctaccacccg | gcacctacca | cacaacttcg | tacctcctga | ttcacgacgg | tgaccgcgct | 660 |
| gttgtgactt | atgagggcga | tactagtgcg | ggctataacc | atgatgtctc | catactccgt | 720 |
| gcgtggatcc | gtaccactaa | aatagttggt | gaccacccgt | tggttataga | gcgtgtgcgg | 780 |
| gccattggct | gtcattttgt | gctgctgctc | accgcagccc | tgaaccgtc | acctatgcct | 840 |
| tatgtcccct | accctcgttc | aacggaggtg | tatgttcgat | ccatatttgg | ccctggcggc | 900 |
| tccccatcct | tgtttccgtc | agcctgctct | actaaatcta | catttcatgc | tgtcccggtt | 960 |
| catatctggg | atcggctcat | gcttttttggt | gccaccctgg | atgaccaggc | cttttgttgt | 1020 |
| tcacggctca | tgacctacct | ccgtggtatt | agctacaagg | tcactgtcgg | tgcgcttgtc | 1080 |
| gctaatgagg | ggtggaacgc | ctctgaagat | gctcttactg | cagtgattac | tgccgcttat | 1140 |
| ctgactattt | gccatcagcg | ttatcttcgc | acccaggcga | tatccaaggg | catgcgccgg | 1200 |
| ctggaggttg | agcacgccca | gaaatttatc | acaagacttt | acagttggct | atttgagaag | 1260 |
| tctggccgta | ttatatccc | cggccgtcag | cttcagttct | acgcacagtg | ccggcggtgg | 1320 |
| ttatctgcag | gcttccacct | agaccccagg | gtgcttgttt | ttgatgaatc | agtgccatgc | 1380 |
| cgctgcagga | cgtttttgaa | gaaagtcgca | ggtaagttct | gctgttttat | gcggtggtta | 1440 |
| gggcaggagt | gtacctgttt | cttggagcca | gccgaaggct | tggttggcga | ctatggccat | 1500 |
| gacaacgagg | cctatgaggg | ttctgaggtc | gacccggctg | aacctgctca | tcttgatgtt | 1560 |
| tctgggacct | atgccgttca | cgggcgccag | cttgaggctc | tctataggc | acttaatgtc | 1620 |
| ccacatgaca | tcgccgctcg | agcctcccgc | ctaacggcta | ctgttgagct | cactgcaagc | 1680 |
| ccagaccgtt | tagagtgccg | cactgtgctt | ggtaataaga | ccttcaggac | gacggtggtt | 1740 |
| gatggcgccc | atcttgaggc | gaatggtcct | gagcagtatg | tcctatcatt | cgacgcctcc | 1800 |
| cgccagtcta | tgggggccgg | gtcacatagc | ctcacttatg | agctcacccc | tgccggcctg | 1860 |
| caggtcagga | tttcatctaa | tggcctggat | tgcacagcca | cattcccccc | cggcggcgcc | 1920 |
| cctagcgctg | cgccggggga | ggtggcggcc | ttttgcagtg | ccctttatag | atataatagg | 1980 |
| ttcacccagc | ggcattcgct | gaccggtggg | ttatggctac | accctgaggg | attgctgggc | 2040 |
| atcttccccc | ctttctcccc | tgggcacatt | tgggagcctg | ctaaccctt | ctgcggggag | 2100 |
| gggactttgt | ataccggac | ttggtcaaca | tctggctttt | ctagcgattt | ctcccccct | 2160 |
| gaggcggccg | ccccgtttt | ggccgctgcc | ccggggctgc | cccaccctac | cccacctgtt | 2220 |
| agtgacattt | gggtgttacc | accaccttca | aaggagtctc | aggtcgatgc | ggcatctgtg | 2280 |

```
ccccctgctc ctgagcccgc tggattaccc agctccattg tgcttaccct cccccccccc    2340
ctccctcctg tgcgtaagcc accaacaccc ccgccttccc gcactcgtcg tctcctctac    2400
acctatcccg acggcgcaaa ggtgtatgcg gggtcattgt ttgaatcaga ctgtaactgg    2460
ctggttaatg cctcaaaccc gggccaccgc cctggaggtg gcctctgcca tgcttttac     2520 caacgtttcc cagaggcgtt ttacccgact gagttcatta tgcgtgaggg ccttgcagca    2580
tataccctga ccccgcgccc tatcattcat gcagtggccc ccgactatag ggttgagcag    2640
aatccgaaga ggcttgaggc agcgtaccgg gagacttgct cccgtcgtgg caccgccgcc    2700
tacccgcttc taggctcggg tataccag gtccctgtca gcctcagttt tgatgcctgg      2760
gaacgcaatc accgccccgg cgatgagctt tatttgactg agcccgccgc agcctggttc    2820
gaggctaata agccggcgca gccggcgctt actataactg aggacacagc ccgtacggcc    2880
aacctagcgt tagagatcga tgctgccaca gatgttggcc gtgcttgtgc cggctgcact    2940
atcagtcctg ggattgtgca ctatcagttc actgccgggg tcccaggctc gggcaagtct    3000
cggtccatac aacagggaga tgtcgatgtg gtggtcgtgc ccacccggga gctccgtaat    3060
agttggcgtc gccggggttt tgcggctttc acacctcaca cagcagcccg tgtcactatc    3120
ggtcgccgcg ttgtgattga tgaggctcca tctctccctc cacacctgtt gctgttacac    3180
atgcagcggg cctcctcggt ccatctcctt ggtgacccaa atcagatccc tgccattgat    3240
tttgaacacg ccgcctggt tccgcgatc cgccctgagc ttgctccaac gagctggtgg      3300
cacgttacac accgttgccc ggccgatgta tgcgagctca tacgcggagc ctaccctaaa    3360
atccagacca cgagccgtgt gctgcggtcc tgttctgga acgaacctgc tatcggccag     3420
aagttggtct tcacgcaggc tgctaaagct gctaaccctg gtgcgattac ggttcatgaa    3480
gctcagggtg ccacttttac agagaccaca attatagcca cggccgatgc caggggcctt    3540
atccagtcat cccgggctca cgctatagtc gcactcaccc gccacactga aagtgtgtt    3600 attctggatg ctccccggcct gctgcgtgag gtcggcattt cggatgtgat tgtcaataac    3660 ttttccttg ctggcggaga agtcggccat caccgcccctt ctgtgatacc ccgcggtaac    3720
cctgatcaga acctcgggac tctacaggcc ttcccgccgt cctgccagat tagtgcttac    3780
caccaattgg ctgaagaatt aggccaccgt ccggctcctg ttgccgccgt cttgccccct    3840
tgccctgagc ttgagcaggg cctgctctat atgccacaag agcttactgt gtctgatagt    3900
gtgttggttt ttgagctcac ggatatagtc cactgtcgca tggccgctcc gagccagcga    3960
aaggctgttc tctcaacact tgtagggaga tacggccgta ggacgaaatt atatgaggca    4020
gcgcattcag atgttcgtga gtccctggcc aggttcattc ccactatcgg gcctgttcag    4080
gccaccacat gtgagttgta tgagttggtt gaggccatgg tggagaaggg acaggacggc    4140
tctgccgtcc tagagcttga cctttgcaat cgtgacgtat cgcgcatcac attttttccaa    4200 aaggattgca acaagtttac aactggtgag actatcgccc atggcaaggt tggtcagggt    4260
atatcggcct ggagtaagac cttctgtgct ctgtttggcc cgtggttccg tgccattgaa    4320
aaagaaatac tggccctact cccgcctaat atctttatg gcgacgccta tgaggaatca    4380
gtgttcgctg ccgctgtgtc cggggcgggg tcgtgcatgt tatttgaaaa tgactttca    4440 gagtttgaca gtacccaaaa taatttctcc cttggccttg agtgtgtggt tatggaggag    4500
tgcggcatgc cccagtggct aattaggttg tatcatctgg ttcggtcagc ctggattttg    4560
caggcgccga aggagtctct taagggttc tggaagaagc attctggtga gcctggtacc    4620
```

| | |
|---|---|
| cttctctgga acaccgtctg gaacatggcg attatagcac attgttatga gtttcgtgac | 4680 |
| tttcgtgttg ccgccttcaa gggtgatgat tcagtggtcc tttgtagtga ctaccgacag | 4740 |
| agccgtaatg cggctgcctt aattgcaggc tgtgggctca aattgaaggt tgactaccgc | 4800 |
| cctattgggc tgtatgccgg ggtggtggtg cccctggtc tggggacact gcctgatgtt | 4860 |
| gtgcgtttcg ccggtcggtt gtctgaaaag aattggggcc ccggcccaga gcgtgctgag | 4920 |
| cagctgcgtc ttgctgtttg tgacttcctt cgagggttga caaatgttgc gcaggtttgt | 4980 |
| gttgatgttg tgtcccgtgt ttatggagtt agccccgggc tggtgcataa ccttattggc | 5040 |
| atgctgcaga ctattgccga tggcaaggcc cactttacag agactattaa acctgtgctt | 5100 |
| gaccttacaa actctatcat acagcgggtg gaatgaataa catgtctttt gcatcgccca | 5160 |
| tgggatcacc atgcgcccta gggctgttct gttgttgctc ttcgtgcttc tgcctatgct | 5220 |
| gcccgcgcca ccgccggcc agccgtctgg ccgccgttgt gggcggcgca acggcggtgc | 5280 |
| cggcggtggt ttctggggtg acagggttga ttctcagccc ttcgccctcc cctatattca | 5340 |
| tccaaccaac cccttcgctg ccgatgtcgt ttcacaaccc ggggctggag ttcgccctcg | 5400 |
| acagccgccc cgcccccttg gctccgcttg gcgtgaccag tccagcgcc cctccactgc | 5460 |
| cccccgtcgt cgatctgccc cagctggggc tgcgccgctg actgctgtat caccggcccc | 5520 |
| cgacacagct cctgtacctg atgttgactc acgtggtgct atcctgcgcc ggcagtacaa | 5580 |
| tctgtctacg tccccgctca cgtcatctgt cgctgctggt accaacctgg ttctctatgc | 5640 |
| cgccccgctg aatcctctct tgcccctcca ggatggcacc aacactcata ttatggctac | 5700 |
| tgaggcgtcc aattatgctc agtatcgggt tgttcgagct acgatccgtt atcgcccgct | 5760 |
| ggtgccaaat gctgttggtg gctatgctat ctctatttct ttctggcctc aaactacaac | 5820 |
| caccccctact tcagttgaca tgaactctat tacctccact gatgtcagga ttttggttca | 5880 |
| gcccggtatt gcctccgagt tagtcatccc tagtgagcgc cttcattacc gcaatcaagg | 5940 |
| ctggcgctct gtagagacca cgggcgtggc cgaggaggaa gctacctccg gtctggtaat | 6000 |
| gctttgcatt cacggttctc ctgttaactc ctatactaac acaccttaca ctggtgcatt | 6060 |
| ggggctcctt gatttgcat tagagcttga attcagaaat ttgacacccg gaacactaa | 6120 |
| cacccgtgtt tccggtaca ccagcacagc ccgccatcgg ctgcgccgcg tgctgatgg | 6180 |
| gaccgcagag cttaccacca cagcagccac acgtttcatg aaggacttgc atttcaccgg | 6240 |
| cacgaacggc gttggtgagg tggtcgcgg tatagctcta acactgttta accttgctga | 6300 |
| tacgcttctt ggtggtttac cgacagaatt gatttcgtcg gccgggggcc aactgtttta | 6360 |
| ctcccgccct gtcgtctcgg ccaatggcga gccgacggtt aagttatata catctgttga | 6420 |
| gaatgcgcag caggacaagg gcattaccat cccacacgat atagatctgg gtgattcccg | 6480 |
| tgtggttatt caggattatg ataaccagca cgagcaagac cgacctactc cgtcaccagc | 6540 |
| cccctctcgc cctttctcag ttcttcgcgc caatgatgtt ctgtggctct ccctcaccgc | 6600 |
| cgctgagtac gatcagacta catatgggtc gtccaccaac cctatgtatg tctccgatac | 6660 |
| ggtcacgcta gttaatgtgg ccactggtgc tcaggctgtt gcccgctctc ttgattggtc | 6720 |
| taaagtcact ctgatggcc gcccctcac taccattcag cagtattcaa agacattcta | 6780 |
| tgttctcccg ctccgcggga agctgtcctt tgggaggct ggtaccacta aggccggcta | 6840 |
| cccgtataat tataatacca ctgctagtga tcaaattttg attgagaacg cggctggcca | 6900 |
| ccgtgttgct atctctacct ataccactag cttgggtgcc ggcccctacct cgatttccgc | 6960 |
| cgttggtgtg ctagccccac actcggctct cgccgtcctt gaggatactg ttgattaccc | 7020 |

```
tgctcgtgct catacttttg atgatttctg cccggagtgc cgcacccttg gtttgcaggg    7080
ttgtgcattc cagtctacta ttgctgagct tcagcgtctt aaaatgaagg taggtaaaac    7140
ccgggagtct taattaattc cttttgtgcc cccttcatag cttcctttgg ttttatttct    7200
tatttct                                                              7207
```

```
<210> SEQ ID NO 4
<211> LENGTH: 21
<212> TYPE: DNA
<213> ORGANISM: Hepatitis E virus

<400> SEQUENCE: 4
aaytatgcma gtaccgggtt g                                              21

<210> SEQ ID NO 5
<211> LENGTH: 23
<212> TYPE: DNA
<213> ORGANISM: Hepatitis E virus

<400> SEQUENCE: 5
cccttatcct gctgagcatt ctc                                            23

<210> SEQ ID NO 6
<211> LENGTH: 22
<212> TYPE: DNA
<213> ORGANISM: Hepatitis E virus

<400> SEQUENCE: 6
gtyatgytyt gcatacatgg ct                                             22

<210> SEQ ID NO 7
<211> LENGTH: 22
<212> TYPE: DNA
<213> ORGANISM: Hepatitis E virus

<400> SEQUENCE: 7
agccgacgaa atyaattctg tc                                             22

<210> SEQ ID NO 8
<211> LENGTH: 23
<212> TYPE: DNA
<213> ORGANISM: Hepatitis E virus

<400> SEQUENCE: 8
gccgagtayg accagtccac tta                                            23

<210> SEQ ID NO 9
<211> LENGTH: 23
<212> TYPE: DNA
<213> ORGANISM: Hepatitis E virus

<400> SEQUENCE: 9
ayaactcccg agttttaccc acc                                            23

<210> SEQ ID NO 10
<211> LENGTH: 23
<212> TYPE: DNA
<213> ORGANISM: Hepatitis E virus

<400> SEQUENCE: 10
tggtkaatgt wgcgacyggc gcg                                            23
```

<210> SEQ ID NO 11
<211> LENGTH: 23
<212> TYPE: DNA
<213> ORGANISM: Hepatitis E virus

<400> SEQUENCE: 11
gctcagcgac agtwgactgr aaa                                    23

<210> SEQ ID NO 12
<211> LENGTH: 660
<212> TYPE: PRT
<213> ORGANISM: Hepatitis E virus

<400> SEQUENCE: 12

```
Met Arg Pro Arg Pro Ile Leu Leu Leu Leu Met Phe Leu Pro Met
 1               5                  10                  15

Leu Pro Ala Pro Pro Gly Gln Pro Ser Gly Arg Arg Gly Arg
            20                  25                  30

Arg Ser Gly Gly Ser Gly Gly Phe Trp Gly Asp Arg Val Asp Ser
        35                  40                  45

Gln Pro Phe Ala Ile Pro Tyr Ile His Pro Thr Asn Pro Phe Ala Pro
    50                  55                  60

Asp Val Thr Ala Ala Ala Gly Ala Gly Pro Arg Val Arg Gln Pro Ala
65                  70                  75                  80

Arg Pro Leu Gly Ser Ala Trp Arg Asp Gln Ala Gln Arg Pro Ala Ala
                85                  90                  95

Ala Ser Arg Arg Arg Pro Thr Thr Ala Gly Ala Ala Pro Leu Thr Ala
            100                 105                 110

Val Ala Pro Ala His Asp Thr Pro Val Pro Asp Val Asp Ser Arg
            115                 120                 125

Gly Ala Ile Leu Arg Arg Gln Tyr Asn Leu Ser Thr Ser Pro Leu Thr
        130                 135                 140

Ser Ser Val Ala Thr Gly Thr Asn Leu Val Leu Tyr Ala Ala Pro Leu
145                 150                 155                 160

Ser Pro Leu Leu Pro Leu Gln Asp Gly Thr Asn Thr His Ile Met Ala
                165                 170                 175

Thr Glu Ala Ser Asn Tyr Ala Gln Tyr Arg Val Ala Arg Ala Thr Ile
            180                 185                 190

Arg Tyr Arg Pro Leu Val Pro Asn Ala Val Gly Gly Tyr Ala Ile Ser
        195                 200                 205

Ile Ser Phe Trp Pro Gln Thr Thr Thr Pro Thr Ser Val Asp Met
        210                 215                 220

Asn Ser Ile Thr Ser Thr Asp Val Arg Ile Leu Val Gln Pro Gly Ile
225                 230                 235                 240

Ala Ser Glu Leu Val Ile Pro Ser Glu Arg Leu His Tyr Arg Asn Gln
                245                 250                 255

Gly Trp Arg Ser Val Glu Thr Ser Gly Val Ala Glu Glu Ala Thr
            260                 265                 270

Ser Gly Leu Val Met Leu Cys Ile His Gly Ser Pro Val Asn Ser Tyr
        275                 280                 285

Thr Asn Thr Pro Tyr Thr Gly Ala Leu Gly Leu Leu Asp Phe Ala Leu
        290                 295                 300

Glu Leu Glu Phe Arg Asn Leu Thr Pro Gly Asn Thr Asn Thr Arg Val
305                 310                 315                 320

Ser Arg Tyr Ser Ser Thr Ala Arg His Arg Leu Arg Arg Gly Ala Asp
```

-continued

```
                    325                 330                 335
Gly Thr Ala Glu Leu Thr Thr Ala Ala Thr Arg Phe Met Lys Asp
                340                 345                 350
Leu Tyr Phe Thr Ser Thr Asn Gly Val Gly Glu Ile Gly Arg Gly Ile
            355                 360                 365
Ala Leu Thr Leu Phe Asn Leu Ala Asp Thr Leu Leu Gly Gly Leu Pro
        370                 375                 380
Thr Glu Leu Ile Ser Ser Ala Gly Gly Gln Leu Phe Tyr Ser Arg Pro
385                 390                 395                 400
Val Val Ser Ala Asn Gly Glu Pro Thr Val Lys Leu Tyr Thr Ser Val
                405                 410                 415
Glu Asn Ala Gln Gln Asp Lys Gly Ile Ala Ile Pro His Asp Ile Asp
            420                 425                 430
Leu Gly Glu Ser Arg Val Val Ile Gln Asp Tyr Asp Asn Gln His Glu
        435                 440                 445
Gln Asp Arg Pro Thr Pro Ser Pro Ala Pro Ser Arg Pro Phe Ser Val
450                 455                 460
Leu Arg Ala Asn Asp Val Leu Trp Leu Ser Leu Thr Ala Ala Glu Tyr
465                 470                 475                 480
Asp Gln Ser Thr Tyr Gly Ser Ser Thr Gly Pro Val Tyr Val Ser Asp
                485                 490                 495
Ser Val Thr Leu Val Asn Val Ala Thr Gly Ala Gln Ala Val Ala Arg
            500                 505                 510
Ser Leu Asp Trp Thr Lys Val Thr Leu Asp Gly Arg Pro Leu Ser Thr
        515                 520                 525
Ile Gln Gln Tyr Ser Lys Thr Phe Phe Val Leu Pro Leu Arg Gly Lys
        530                 535                 540
Leu Ser Phe Trp Glu Ala Gly Thr Thr Lys Ala Gly Tyr Pro Tyr Asn
545                 550                 555                 560
Tyr Asn Thr Thr Ala Ser Asp Gln Leu Leu Val Glu Asn Ala Ala Gly
                565                 570                 575
His Arg Val Ala Ile Ser Thr Tyr Thr Thr Ser Leu Gly Ala Gly Pro
            580                 585                 590
Val Ser Ile Ser Ala Val Ala Val Leu Ala Pro His Ser Val Leu Ala
        595                 600                 605
Leu Leu Glu Asp Thr Met Asp Tyr Pro Ala Arg Ala His Thr Phe Asp
        610                 615                 620
Asp Phe Cys Pro Glu Cys Arg Pro Leu Gly Leu Gln Gly Cys Ala Phe
625                 630                 635                 640
Gln Ser Thr Val Ala Glu Leu Gln Arg Leu Lys Met Lys Val Gly Lys
                645                 650                 655
Thr Arg Glu Leu
            660

<210> SEQ ID NO 13
<211> LENGTH: 123
<212> TYPE: PRT
<213> ORGANISM: Hepatitis E virus

<400> SEQUENCE: 13

Met Asn Asn Met Ser Phe Ala Ala Pro Met Gly Ser Arg Pro Cys Ala
1               5                   10                  15
Leu Gly Leu Phe Cys Cys Cys Ser Ser Cys Phe Cys Leu Cys Cys Pro
            20                  25                  30
```

```
Arg His Arg Pro Val Ser Arg Leu Ala Ala Val Val Gly Gly Ala Ala
         35                  40                  45

Ala Val Pro Ala Val Val Ser Gly Val Thr Gly Leu Ile Leu Ser Pro
 50                  55                  60

Ser Gln Ser Pro Ile Phe Ile Gln Pro Thr Pro Ser Pro Pro Met Ser
 65                  70                  75                  80

Pro Leu Arg Pro Gly Leu Asp Leu Val Phe Ala Asn Pro Pro Asp His
                 85                  90                  95

Ser Ala Pro Leu Gly Val Thr Arg Pro Ser Ala Pro Pro Leu Pro His
                100                 105                 110

Val Val Asp Leu Pro Gln Leu Gly Pro Arg Arg
        115                 120
```

<210> SEQ ID NO 14
<211> LENGTH: 22
<212> TYPE: DNA
<213> ORGANISM: Hepatitis E virus

<400> SEQUENCE: 14
atatgtggtc gatgccatgg ag                                            22

<210> SEQ ID NO 15
<211> LENGTH: 22
<212> TYPE: DNA
<213> ORGANISM: Hepatitis E virus

<400> SEQUENCE: 15
ctcggcagta ctgttccagt tc                                            22

<210> SEQ ID NO 16
<211> LENGTH: 22
<212> TYPE: DNA
<213> ORGANISM: Hepatitis E virus

<400> SEQUENCE: 16
tcgatgccat ggaggcccat ca                                            22

<210> SEQ ID NO 17
<211> LENGTH: 22
<212> TYPE: DNA
<213> ORGANISM: Hepatitis E virus

<400> SEQUENCE: 17
gtattgcccg ctggatagga tc                                            22

<210> SEQ ID NO 18
<211> LENGTH: 22
<212> TYPE: DNA
<213> ORGANISM: Hepatitis E virus

<400> SEQUENCE: 18
aaggctcmtg gcatcactac tg                                            22

<210> SEQ ID NO 19
<211> LENGTH: 22
<212> TYPE: DNA
<213> ORGANISM: Hepatitis E virus

<400> SEQUENCE: 19
cagaggcrtt ccagccttca tt                                            22

-continued

```
<210> SEQ ID NO 20
<211> LENGTH: 22
<212> TYPE: DNA
<213> ORGANISM: Hepatitis E virus

<400> SEQUENCE: 20
tggcatcact actgytattg ag                                              22

<210> SEQ ID NO 21
<211> LENGTH: 22
<212> TYPE: DNA
<213> ORGANISM: Hepatitis E virus

<400> SEQUENCE: 21
gggagcagca aaaggcytgg tc                                              22

<210> SEQ ID NO 22
<211> LENGTH: 28
<212> TYPE: DNA
<213> ORGANISM: Hepatitis E virus

<400> SEQUENCE: 22
tctacatttc atgctgtccc ggttcata                                        28

<210> SEQ ID NO 23
<211> LENGTH: 20
<212> TYPE: DNA
<213> ORGANISM: Hepatitis E virus

<400> SEQUENCE: 23
tcctgaccaa gccacttcat                                                 20

<210> SEQ ID NO 24
<211> LENGTH: 20
<212> TYPE: DNA
<213> ORGANISM: Hepatitis E virus

<400> SEQUENCE: 24
gatgaccaag cctttttgctg                                                20

<210> SEQ ID NO 25
<211> LENGTH: 20
<212> TYPE: DNA
<213> ORGANISM: Hepatitis E virus

<400> SEQUENCE: 25
taatcacggc cggacttctc                                                 20

<210> SEQ ID NO 26
<211> LENGTH: 26
<212> TYPE: DNA
<213> ORGANISM: Hepatitis E virus

<400> SEQUENCE: 26
tgccatcagc gttatcttcg caccca                                          26

<210> SEQ ID NO 27
<211> LENGTH: 26
<212> TYPE: DNA
<213> ORGANISM: Hepatitis E virus

<400> SEQUENCE: 27
gcacggccaa catctgtggc agcatc                                          26
```

```
<210> SEQ ID NO 28
<211> LENGTH: 26
<212> TYPE: DNA
<213> ORGANISM: Hepatitis E virus

<400> SEQUENCE: 28
acccaggcga tatccaaggg catgcg                                              26

<210> SEQ ID NO 29
<211> LENGTH: 26
<212> TYPE: DNA
<213> ORGANISM: Hepatitis E virus

<400> SEQUENCE: 29
gcatcgatct ctaacgctag gttggc                                              26

<210> SEQ ID NO 30
<211> LENGTH: 20
<212> TYPE: DNA
<213> ORGANISM: Hepatitis E virus

<400> SEQUENCE: 30
tatmgrttgg aacataaccc                                                     20

<210> SEQ ID NO 31
<211> LENGTH: 20
<212> TYPE: DNA
<213> ORGANISM: Hepatitis E virus

<400> SEQUENCE: 31
cggtgtgtaa cgtgccacca                                                     20

<210> SEQ ID NO 32
<211> LENGTH: 20
<212> TYPE: DNA
<213> ORGANISM: Hepatitis E virus

<400> SEQUENCE: 32
ttygaygcct gggagcggaa                                                     20

<210> SEQ ID NO 33
<211> LENGTH: 20
<212> TYPE: DNA
<213> ORGANISM: Hepatitis E virus

<400> SEQUENCE: 33
aaatcaatgg cagggatctg                                                     20

<210> SEQ ID NO 34
<211> LENGTH: 22
<212> TYPE: DNA
<213> ORGANISM: Hepatitis E virus

<400> SEQUENCE: 34
ggcgymgggt tgtcattgat ga                                                  22

<210> SEQ ID NO 35
<211> LENGTH: 22
<212> TYPE: DNA
<213> ORGANISM: Hepatitis E virus

<400> SEQUENCE: 35
gggagtaggg ccagtatttc tt                                                  22
```

<210> SEQ ID NO 36
<211> LENGTH: 22
<212> TYPE: DNA
<213> ORGANISM: Hepatitis E virus

<400> SEQUENCE: 36
ttggygaccc gaaycagatc cc					22

<210> SEQ ID NO 37
<211> LENGTH: 22
<212> TYPE: DNA
<213> ORGANISM: Hepatitis E virus

<400> SEQUENCE: 37 cttttcaat ggcacggaac ca					22

<210> SEQ ID NO 38
<211> LENGTH: 23
<212> TYPE: DNA
<213> ORGANISM: Hepatitis E virus

<400> SEQUENCE: 38
gaggcsatgg tsgagaaggg cca					23

<210> SEQ ID NO 39
<211> LENGTH: 22
<212> TYPE: DNA
<213> ORGANISM: Hepatitis E virus

<400> SEQUENCE: 39
aagagcaaca acagaacagc cc					22

<210> SEQ ID NO 40
<211> LENGTH: 23
<212> TYPE: DNA
<213> ORGANISM: Hepatitis E virus

<400> SEQUENCE: 40
accttyttcc agaargattg taa					23

<210> SEQ ID NO 41
<211> LENGTH: 22
<212> TYPE: DNA
<213> ORGANISM: Hepatitis E virus

<400> SEQUENCE: 41
ctagggcgca tggtgatccc at					22

<210> SEQ ID NO 42
<211> LENGTH: 22
<212> TYPE: DNA
<213> ORGANISM: Hepatitis E virus

<400> SEQUENCE: 42
ctggaagaar caytcyggtg ag					22

<210> SEQ ID NO 43
<211> LENGTH: 22
<212> TYPE: DNA
<213> ORGANISM: Hepatitis E virus

<400> SEQUENCE: 43

-continued

```
aagagcaaca acagaacagc cc                                              22

<210> SEQ ID NO 44
<211> LENGTH: 22
<212> TYPE: DNA
<213> ORGANISM: Hepatitis E virus

<400> SEQUENCE: 44
tggaatackg tstggaayat gg                                              22

<210> SEQ ID NO 45
<211> LENGTH: 22
<212> TYPE: DNA
<213> ORGANISM: Hepatitis E virus

<400> SEQUENCE: 45
ctagggcgca tggtgatccc at                                              22

<210> SEQ ID NO 46
<211> LENGTH: 22
<212> TYPE: DNA
<213> ORGANISM: Hepatitis E virus

<400> SEQUENCE: 46
ctcagttctt cgcgccaatg at                                              22

<210> SEQ ID NO 47
<211> LENGTH: 22
<212> TYPE: DNA
<213> ORGANISM: Hepatitis E virus

<400> SEQUENCE: 47 ttttttcag ggagcgcggr ac                                               22

<210> SEQ ID NO 48
<211> LENGTH: 660
<212> TYPE: PRT
<213> ORGANISM: Hepatitis E virus

<400> SEQUENCE: 48
```

Met Arg Pro Arg Pro Leu Leu Leu Phe Leu Leu Phe Leu Pro Met
 1               5                  10                  15

Leu Pro Ala Pro Pro Thr Gly Gln Pro Ser Gly Arg Arg Gly Arg
            20                  25                  30

Arg Ser Gly Gly Thr Gly Gly Gly Phe Trp Gly Asp Arg Val Asp Ser
        35                  40                  45

Gln Pro Phe Ala Ile Pro Tyr Ile His Pro Thr Asn Pro Phe Ala Pro
    50                  55                  60

Asp Val Ala Ala Ala Ser Gly Ser Gly Pro Arg Leu Arg Gln Pro Ala
65                  70                  75                  80

Arg Pro Leu Gly Ser Thr Trp Arg Asp Gln Ala Gln Arg Pro Ser Ala
                85                  90                  95

Ala Ser Arg Arg Arg Pro Thr Thr Ala Gly Ala Ala Ala Leu Thr Ala
            100                 105                 110

Val Ala Pro Ala His Asp Thr Ser Pro Val Pro Asp Val Asp Ser Arg
        115                 120                 125

Gly Ala Ile Leu Arg Arg Gln Tyr Asn Leu Ser Thr Ser Pro Leu Thr
    130                 135                 140

Ser Ser Val Ala Ser Gly Thr Asn Leu Val Leu Tyr Ala Ala Pro Leu
145                 150                 155                 160

-continued

```
Asn Pro Pro Leu Pro Leu Gln Asp Gly Thr Asn Thr His Ile Met Ala
            165                 170                 175

Thr Glu Ala Ser Asn Tyr Ala Gln Tyr Arg Val Ala Arg Ala Thr Ile
            180                 185                 190

Arg Tyr Arg Pro Leu Val Pro Asn Ala Val Gly Gly Tyr Ala Ile Ser
            195                 200                 205

Ile Ser Phe Trp Pro Gln Thr Thr Thr Pro Thr Ser Val Asp Met
            210                 215                 220

Asn Ser Ile Thr Ser Thr Asp Val Arg Ile Leu Val Gln Pro Gly Ile
225                 230                 235                 240

Ala Ser Glu Leu Val Ile Pro Ser Glu Arg Leu His Tyr Arg Asn Gln
            245                 250                 255

Gly Trp Arg Ser Val Glu Thr Ser Gly Val Ala Glu Glu Ala Thr
            260                 265                 270

Ser Gly Leu Val Met Leu Cys Ile His Gly Ser Pro Val Asn Ser Tyr
            275                 280                 285

Thr Asn Thr Pro Tyr Thr Gly Ala Leu Gly Leu Leu Asp Phe Ala Leu
            290                 295                 300

Glu Leu Glu Phe Arg Asn Leu Thr Thr Cys Asn Thr Asn Thr Arg Val
305                 310                 315                 320

Ser Arg Tyr Ser Ser Thr Ala Arg His Ser Ala Arg Arg Gly Ala Asp
            325                 330                 335

Gly Thr Ala Glu Leu Thr Thr Thr Ala Ala Thr Arg Phe Met Lys Asp
            340                 345                 350

Leu His Phe Thr Gly Leu Asn Gly Val Gly Glu Val Gly Arg Gly Ile
            355                 360                 365

Ala Leu Thr Leu Leu Asn Leu Ala Asp Thr Leu Leu Gly Gly Leu Pro
            370                 375                 380

Thr Glu Leu Ile Ser Ser Ala Gly Gly Gln Leu Phe Tyr Ser Arg Pro
385                 390                 395                 400

Val Val Ser Ala Asn Gly Glu Pro Thr Val Lys Leu Tyr Thr Ser Val
            405                 410                 415

Glu Asn Ala Gln Gln Asp Lys Gly Val Ala Ile Pro His Asp Ile Asp
            420                 425                 430

Leu Gly Asp Ser Arg Val Val Ile Gln Asp Tyr Asp Asn Gln His Glu
            435                 440                 445

Gln Asp Arg Pro Thr Pro Ser Pro Ala Pro Ser Arg Pro Phe Ser Val
            450                 455                 460

Leu Arg Ala Asn Asp Val Leu Trp Leu Ser Leu Thr Ala Ala Glu Tyr
465                 470                 475                 480

Asp Gln Ser Thr Tyr Gly Ser Ser Thr Gly Pro Val Tyr Ile Ser Asp
            485                 490                 495

Ser Val Thr Leu Val Asn Val Ala Thr Gly Ala Gln Ala Val Ala Arg
            500                 505                 510

Ser Leu Asp Trp Ser Lys Val Thr Leu Asp Gly Arg Pro Leu Pro Thr
            515                 520                 525

Val Glu Gln Tyr Ser Lys Thr Phe Phe Val Leu Pro Leu Arg Gly Lys
            530                 535                 540

Leu Ser Phe Trp Glu Ala Gly Thr Thr Lys Ala Gly Tyr Pro Tyr Asn
545                 550                 555                 560

Tyr Asn Thr Thr Ala Ser Asp Gln Ile Leu Ile Glu Asn Ala Ala Gly
            565                 570                 575
```

His Arg Val Ala Ile Ser Thr Tyr Thr Thr Arg Leu Gly Ala Gly Pro
            580                 585                 590

Val Ala Ile Ser Ala Ala Ala Val Leu Ala Pro Arg Ser Ala Leu Ala
            595                 600                 605

Leu Leu Glu Asp Thr Phe Asp Tyr Pro Gly Arg Ala His Thr Phe Asp
            610                 615                 620

Asp Phe Cys Pro Glu Cys Arg Ala Leu Gly Leu Gln Gly Cys Ala Phe
625                 630                 635                 640

Gln Ser Thr Val Ala Glu Leu Gln Arg Leu Lys Val Lys Val Gly Lys
                645                 650                 655

Thr Arg Glu Leu
            660

<210> SEQ ID NO 49
<211> LENGTH: 660
<212> TYPE: PRT
<213> ORGANISM: Hepatitis E virus

<400> SEQUENCE: 49

Met Arg Pro Arg Pro Ile Leu Leu Leu Leu Met Phe Leu Pro Met
  1               5                  10                  15

Leu Pro Ala Pro Pro Gly Gln Pro Ser Gly Arg Arg Arg Gly Arg
             20                  25                  30

Arg Ser Gly Gly Ser Gly Gly Gly Phe Trp Gly Asp Arg Val Asp Ser
             35                  40                  45

Gln Pro Phe Ala Ile Pro Tyr Ile His Pro Thr Asn Pro Phe Ala Pro
         50                  55                  60

Asp Val Thr Ala Ala Ala Gly Ala Gly Pro Arg Val Arg Gln Pro Val
 65                  70                  75                  80

Arg Pro Leu Gly Ser Ala Trp Arg Asp Gln Ala Gln Arg Pro Ala Ala
                 85                  90                  95

Ala Ser Arg Arg Arg Pro Thr Ala Ala Gly Ala Ala Pro Leu Thr Ala
             100                 105                 110

Val Ala Pro Ala His Asp Thr Pro Pro Val Pro Asp Val Asp Ser Arg
             115                 120                 125

Gly Ala Ile Leu Arg Arg Gln Tyr Asn Leu Ser Thr Ser Pro Leu Thr
         130                 135                 140

Ser Ser Val Ala Thr Gly Thr Asn Leu Val Leu Tyr Ala Ala Pro Leu
145                 150                 155                 160

Ser Pro Leu Leu Pro Leu Gln Asp Gly Thr Asn Thr His Ile Met Ala
                165                 170                 175

Thr Glu Ala Ser Asn Tyr Ala Gln Tyr Arg Val Ala Arg Ala Thr Ile
             180                 185                 190

Arg Tyr Arg Pro Leu Val Pro Asn Ala Val Gly Gly Tyr Ala Ile Ser
         195                 200                 205

Ile Ser Phe Trp Pro Gln Thr Thr Thr Thr Pro Thr Ser Val Asp Met
210                 215                 220

Asn Ser Ile Thr Ser Thr Asp Val Arg Ile Leu Val Gln Pro Gly Ile
225                 230                 235                 240

Ala Ser Glu Leu Val Ile Pro Ser Glu Arg Leu His Tyr Arg Asn Gln
                245                 250                 255

Gly Trp Arg Ser Val Glu Thr Ser Gly Val Ala Glu Glu Ala Thr
             260                 265                 270

Ser Gly Leu Val Met Leu Cys Ile His Gly Ser Pro Val Asn Ser Tyr
             275                 280                 285

-continued

```
Thr Asn Thr Pro Tyr Thr Gly Ala Leu Gly Leu Leu Asp Phe Ala Leu
    290                 295                 300

Glu Leu Glu Phe Arg Asn Leu Thr Pro Gly Asn Thr Asn Thr Arg Val
305                 310                 315                 320

Ser Arg Tyr Ser Ser Thr Ala Arg His Arg Leu Arg Arg Gly Ala Asp
                325                 330                 335

Gly Thr Ala Glu Leu Thr Thr Ala Ala Thr Arg Phe Met Lys Asp
                340                 345                 350

Leu Tyr Phe Thr Ser Thr Asn Gly Val Gly Glu Ile Gly Arg Gly Ile
                355                 360                 365

Ala Leu Thr Leu Phe Asn Leu Ala Asp Thr Leu Leu Gly Gly Leu Pro
    370                 375                 380

Thr Glu Leu Ile Ser Ser Ala Gly Gly Gln Leu Phe Tyr Ser Arg Pro
385                 390                 395                 400

Val Val Ser Ala Asn Gly Glu Pro Thr Val Lys Leu Tyr Thr Ser Val
                405                 410                 415

Glu Asn Ala Gln Gln Asp Lys Gly Ile Ala Ile Pro His Asp Ile Asp
                420                 425                 430

Leu Gly Glu Ser Arg Val Val Ile Gln Asp Tyr Asp Asn Gln His Glu
                435                 440                 445

Gln Asp Arg Pro Thr Pro Ser Pro Ala Pro Ser Arg Pro Phe Ser Val
    450                 455                 460

Leu Arg Ala Asn Asp Val Leu Trp Leu Ser Leu Thr Ala Ala Glu Tyr
465                 470                 475                 480

Asp Gln Ser Thr Tyr Gly Ser Ser Thr Gly Pro Val Tyr Val Ser Asp
                485                 490                 495

Ser Val Thr Leu Val Asn Val Ala Thr Gly Ala Gln Ala Val Ala Arg
                500                 505                 510

Ser Leu Asp Trp Thr Lys Val Thr Leu Asp Gly Arg Pro Leu Ser Thr
    515                 520                 525

Ile Gln Gln Tyr Ser Lys Thr Phe Phe Val Leu Pro Leu Arg Gly Lys
    530                 535                 540

Leu Ser Phe Trp Glu Ala Gly Thr Thr Lys Ala Gly Tyr Pro Tyr Asn
545                 550                 555                 560

Tyr Asn Thr Thr Ala Ser Asp Gln Leu Leu Val Glu Asn Ala Ala Gly
                565                 570                 575

His Arg Val Ala Ile Ser Thr Tyr Thr Thr Ser Leu Gly Ala Gly Pro
                580                 585                 590

Val Ser Ile Ser Ala Val Ala Val Leu Thr Pro His Ser Ala Leu Ala
    595                 600                 605

Leu Leu Glu Asp Thr Met Asp Tyr Pro Ala Arg Ala His Thr Phe Asp
610                 615                 620

Asp Phe Cys Pro Glu Cys Arg Pro Leu Gly Leu Gln Gly Cys Ala Phe
625                 630                 635                 640

Gln Ser Thr Val Ala Glu Leu Gln Arg Leu Lys Met Lys Val Gly Lys
                645                 650                 655

Thr Arg Glu Leu
            660

<210> SEQ ID NO 50
<211> LENGTH: 660
<212> TYPE: PRT
<213> ORGANISM: Hepatitis E virus
```

-continued

<400> SEQUENCE: 50

```
Met Arg Pro Arg Pro Ile Leu Leu Leu Leu Met Phe Leu Pro Met
  1               5                  10                  15

Leu Pro Ala Pro Pro Gly Gln Pro Ser Gly Arg Arg Gly Arg
             20                  25                  30

Arg Ser Gly Gly Ser Gly Gly Gly Phe Trp Gly Asp Arg Val Asp Ser
         35                  40                  45

Gln Pro Phe Ala Ile Pro Tyr Ile His Pro Thr Asn Pro Phe Ala Pro
 50                  55                  60

Asp Val Thr Ala Ala Ala Gly Ala Gly Pro Arg Val Arg Gln Pro Ala
 65                  70                  75                  80

Arg Pro Leu Gly Ser Ala Trp Arg Asp Gln Ala Gln Arg Pro Ala Val
             85                  90                  95

Ala Ser Arg Arg Arg Pro Thr Thr Ala Gly Ala Ala Pro Leu Thr Ala
            100                 105                 110

Val Ala Pro Ala His Asp Thr Pro Val Pro Asp Val Asp Ser Arg
            115                 120                 125

Gly Ala Ile Leu Arg Arg Gln Tyr Asn Leu Ser Thr Ser Pro Leu Thr
        130                 135                 140

Ser Ser Val Ala Thr Gly Thr Asn Leu Val Leu Tyr Ala Ala Pro Leu
145                 150                 155                 160

Ser Pro Leu Leu Pro Leu Gln Asp Gly Thr Asn Thr His Ile Met Ala
                165                 170                 175

Thr Glu Ala Ser Asn Tyr Ala Gln Tyr Arg Val Ala Arg Ala Thr Ile
                180                 185                 190

Arg Tyr Arg Pro Leu Val Pro Asn Ala Val Gly Gly Tyr Ala Ile Ser
                195                 200                 205

Ile Ser Phe Trp Pro Gln Thr Thr Thr Pro Thr Ser Val Asp Met
        210                 215                 220

Asn Ser Ile Thr Ser Thr Asp Val Arg Ile Leu Val Gln Pro Gly Ile
225                 230                 235                 240

Ala Ser Glu Leu Val Ile Pro Ser Glu Arg Leu His Tyr Arg Asn Gln
                245                 250                 255

Gly Trp Arg Ser Val Glu Thr Ser Gly Val Ala Glu Glu Ala Thr
            260                 265                 270

Ser Gly Leu Val Met Leu Cys Ile His Gly Ser Leu Val Asn Ser Tyr
        275                 280                 285

Thr Asn Thr Pro Tyr Thr Gly Ala Leu Gly Leu Leu Asp Phe Ala Leu
    290                 295                 300

Glu Leu Glu Phe Arg Asn Leu Thr Pro Gly Asn Thr Asn Thr Arg Val
305                 310                 315                 320

Ser Arg Tyr Ser Ser Thr Ala Arg His Arg Leu Arg Arg Gly Ala Asp
                325                 330                 335

Gly Thr Ala Glu Leu Thr Thr Ala Ala Thr Arg Phe Met Lys Asp
            340                 345                 350

Leu Tyr Phe Thr Ser Thr Asn Gly Val Gly Glu Ile Gly Arg Gly Ile
        355                 360                 365

Ala Leu Thr Leu Phe Asn Leu Ala Asp Thr Leu Leu Gly Gly Leu Pro
    370                 375                 380

Thr Glu Leu Ile Ser Ser Ala Gly Gly Gln Leu Phe Tyr Ser Arg Pro
385                 390                 395                 400

Val Val Ser Ala Asn Gly Glu Pro Thr Val Lys Leu Tyr Thr Ser Val
                405                 410                 415
```

```
Glu Asn Ala Gln Gln Asp Lys Gly Ile Ala Ile Pro His Asp Ile Asp
                420                 425                 430
Leu Gly Glu Ser Arg Val Val Ile Gln Asp Tyr Asp Asn Gln His Glu
            435                 440                 445
Gln Asp Arg Pro Thr Pro Ser Pro Ala Pro Ser Arg Pro Phe Ser Val
        450                 455                 460
Leu Arg Ala Asn Asp Val Leu Trp Leu Ser Leu Thr Ala Ala Glu Tyr
465                 470                 475                 480
Asp Gln Ser Thr Tyr Gly Ser Ser Thr Gly Pro Val Tyr Val Ser Asp
                485                 490                 495
Ser Val Thr Leu Val Asn Val Ala Thr Gly Ala Gln Ala Val Ala Arg
            500                 505                 510
Ser Leu Asp Trp Thr Lys Val Thr Leu Asp Gly Arg Pro Leu Ser Thr
        515                 520                 525
Ile Gln Gln Tyr Ser Lys Thr Phe Phe Val Leu Pro Leu Arg Gly Lys
530                 535                 540
Leu Ser Phe Trp Glu Ala Gly Thr Thr Lys Ala Gly Tyr Pro Tyr Asn
545                 550                 555                 560
Tyr Asn Thr Thr Ala Ser Asp Gln Leu Leu Val Glu Asn Ala Ala Gly
                565                 570                 575
His Arg Val Ala Ile Ser Thr Tyr Thr Thr Ser Leu Gly Ala Gly Pro
            580                 585                 590
Val Ser Ile Ser Ala Val Ala Val Leu Ala Pro His Ser Ala Leu Ala
        595                 600                 605
Leu Leu Glu Asp Thr Leu Asp Tyr Pro Ala Arg Ala His Thr Phe Asp
610                 615                 620
Asp Phe Cys Pro Glu Cys Arg Pro Leu Gly Leu Gln Gly Cys Ala Phe
625                 630                 635                 640
Gln Ser Thr Val Ala Glu Leu Gln Arg Leu Lys Met Lys Val Gly Lys
                645                 650                 655
Thr Arg Glu Leu
            660

<210> SEQ ID NO 51
<211> LENGTH: 660
<212> TYPE: PRT
<213> ORGANISM: Hepatitis E virus

<400> SEQUENCE: 51

Met Arg Pro Arg Pro Ile Leu Leu Leu Leu Met Phe Leu Pro Met
 1               5                  10                  15
Leu Pro Ala Pro Pro Gly Gln Pro Ser Gly Arg Arg Gly Arg
            20                  25                  30
Arg Ser Gly Gly Ser Gly Gly Gly Phe Trp Gly Asp Arg Val Asp Ser
            35                  40                  45
Gln Pro Phe Ala Ile Pro Tyr Ile His Pro Thr Asn Pro Phe Ala Pro
        50                  55                  60
Asp Val Thr Ala Ala Ala Gly Ala Gly Pro Arg Val Arg Gln Ser Ala
65                  70                  75                  80
Arg Pro Leu Gly Ser Ala Trp Arg Asp Gln Ala Gln Arg Pro Ala Ala
                85                  90                  95
Ala Pro Arg Arg Arg Pro Thr Thr Ala Gly Ala Ala Pro Leu Thr Ala
            100                 105                 110
Val Ala Pro Ala His Asp Thr Pro Pro Val Pro Asp Val Asp Ser Arg
```

-continued

```
            115                 120                 125
Gly Ala Ile Leu Arg Arg Gln Tyr Asn Leu Ser Thr Ser Pro Leu Thr
        130                 135                 140
Ser Ser Val Ala Thr Gly Thr Asn Leu Val Leu Tyr Ala Ala Pro Leu
145                 150                 155                 160
Ser Pro Leu Leu Pro Leu Gln Asp Gly Thr Asn Thr His Ile Met Ala
                165                 170                 175
Thr Glu Ala Ser Asn Tyr Ala Gln Tyr Arg Val Ala Arg Ala Thr Ile
                180                 185                 190
Arg Tyr Arg Pro Leu Val Pro Asn Ala Val Gly Tyr Ala Ile Ser
            195                 200                 205
Ile Ser Phe Trp Pro Gln Thr Thr Thr Pro Thr Ser Val Asp Met
210                 215                 220
Asn Ser Ile Thr Ser Thr Asp Val Arg Ile Leu Val Gln Pro Gly Ile
225                 230                 235                 240
Ala Ser Glu Leu Val Ile Pro Ser Glu Arg Leu His Tyr Arg Asn Gln
                245                 250                 255
Gly Trp Arg Ser Val Glu Thr Ser Gly Val Ala Glu Glu Ala Thr
            260                 265                 270
Ser Gly Leu Val Met Leu Cys Ile His Gly Ser Pro Val Asn Ser Tyr
        275                 280                 285
Thr Asn Thr Pro Tyr Thr Gly Ala Leu Gly Leu Leu Asp Phe Ala Leu
        290                 295                 300
Glu Leu Glu Phe Arg Asn Leu Thr Pro Gly Asn Thr Asn Thr Arg Val
305                 310                 315                 320
Ser Arg Tyr Ser Ser Thr Ala Arg His Arg Leu Arg Arg Gly Ala Asp
                325                 330                 335
Gly Thr Ala Glu Leu Thr Thr Thr Ala Ala Thr Arg Phe Met Lys Asp
                340                 345                 350
Leu Tyr Phe Thr Ser Thr Asn Gly Val Gly Glu Ile Gly Arg Gly Ile
            355                 360                 365
Ala Leu Thr Leu Phe Asn Leu Ala Asp Thr Leu Leu Gly Gly Leu Pro
        370                 375                 380
Thr Glu Leu Ile Ser Ser Ala Gly Gly Gln Leu Phe Tyr Ser Arg Pro
385                 390                 395                 400
Val Val Ser Ala Asn Gly Glu Pro Thr Val Lys Leu Tyr Arg Ser Val
                405                 410                 415
Glu Asn Ala Gln Gln Asp Lys Gly Ile Ala Ile Pro His Asp Ile Asp
                420                 425                 430
Leu Gly Glu Ser Arg Val Val Ile Gln Asp Tyr Asp Asn Gln His Glu
            435                 440                 445
Gln Asp Arg Pro Thr Pro Ser Pro Ala Pro Ser Arg Pro Phe Ser Val
        450                 455                 460
Leu Arg Ala Asn Asp Ala Leu Trp Leu Ser Leu Thr Ala Ala Glu Tyr
465                 470                 475                 480
Asp Gln Ser Thr Tyr Gly Ser Ser Thr Gly Pro Val Tyr Val Ser Asp
                485                 490                 495
Ser Val Thr Leu Val Asn Val Ala Thr Gly Ala Gln Ala Val Ala Arg
            500                 505                 510
Ser Leu Asp Trp Thr Lys Val Thr Leu Asp Gly Arg Pro Leu Ser Thr
        515                 520                 525
Ile Gln Gln Tyr Ser Lys Thr Phe Phe Val Leu Pro Leu Arg Gly Lys
        530                 535                 540
```

-continued

```
Leu Ser Phe Trp Glu Ala Gly Thr Thr Lys Ala Gly Tyr Pro Tyr Asn
545                 550                 555                 560

Tyr Asn Thr Thr Ala Ser Asp Gln Leu Leu Val Glu Asn Ala Ala Gly
                565                 570                 575

His Arg Val Ala Ile Ser Thr Tyr Thr Ser Leu Gly Ala Gly Pro
            580                 585                 590

Val Ser Ile Ser Ala Val Ala Val Leu Ala Pro His Ser Ala Leu Ala
595                 600                 605

Leu Leu Glu Asp Thr Leu Asp Tyr Pro Ala Arg Ala His Thr Phe Asp
        610                 615                 620

Asp Phe Cys Pro Glu Cys Arg Pro Leu Gly Leu Gln Gly Cys Ala Phe
625                 630                 635                 640

Gln Ser Thr Val Ala Glu Leu Gln Arg Leu Lys Met Lys Val Gly Lys
                645                 650                 655

Thr Arg Glu Leu
            660

<210> SEQ ID NO 52
<211> LENGTH: 660
<212> TYPE: PRT
<213> ORGANISM: Hepatitis E virus

<400> SEQUENCE: 52

Met Arg Pro Arg Pro Ile Leu Leu Leu Leu Met Phe Leu Pro Ile
1               5                   10                  15

Val Pro Ala Pro Pro Gly Gln Pro Ser Gly Arg Arg Gly Arg
                20                  25                  30

Arg Ser Gly Gly Ser Gly Gly Phe Trp Gly Asp Arg Val Asp Ser
            35                  40                  45

Gln Pro Phe Ala Ile Pro Tyr Ile His Pro Thr Asn Pro Phe Ala Pro
    50                  55                  60

Asp Val Thr Ala Ala Gly Ala Gly Pro Arg Val Arg Gln Pro Ala
65                  70                  75                  80

Arg Pro Leu Gly Ser Ala Trp Arg Asp Gln Ala Gln Arg Pro Ala Ala
                85                  90                  95

Ala Ser Arg Arg Pro Thr Thr Ala Gly Ala Ala Pro Leu Thr Ala
            100                 105                 110

Val Ala Pro Ala His Asp Thr Pro Val Pro Asp Val Asp Ser Arg
        115                 120                 125

Gly Ala Ile Leu Arg Arg Gln Tyr Asn Leu Ser Thr Ser Pro Leu Thr
130                 135                 140

Ser Ser Val Ala Thr Gly Thr Asn Leu Val Leu Tyr Ala Ala Pro Leu
145                 150                 155                 160

Ser Pro Leu Leu Pro Leu Gln Asp Gly Thr Asn Thr His Ile Met Ala
                165                 170                 175

Thr Glu Ala Ser Asn Tyr Ala Gln Tyr Arg Val Ala Arg Ala Thr Ile
            180                 185                 190

Arg Tyr Arg Pro Leu Val Pro Asn Ala Val Gly Gly Tyr Gly Ile Ser
        195                 200                 205

Ile Ser Phe Trp Pro Gln Thr Thr Thr Thr Pro Thr Ser Val Asp Met
    210                 215                 220

Asn Ser Ile Thr Ser Thr Asp Val Arg Ile Leu Val Gln Pro Gly Ile
225                 230                 235                 240

Ala Ser Glu Leu Val Ile Pro Ser Glu Arg Leu His Tyr Arg Asn Gln
```

-continued

```
                245                 250                 255
Gly Trp Arg Ser Val Glu Thr Ser Gly Val Ala Glu Glu Ala Thr
                260                 265                 270
Ser Gly Leu Val Met Leu Cys Ile His Gly Ser Pro Val Asn Ser Tyr
                275                 280                 285
Thr Asn Thr Pro Tyr Thr Gly Ala Leu Gly Val Leu Asp Phe Ala Leu
                290                 295                 300
Glu Leu Glu Phe Arg Asn Leu Thr Pro Gly Asn Thr Asn Thr Arg Val
305                 310                 315                 320
Ser Arg Tyr Ser Ser Thr Ala Arg His Arg Leu Arg Gly Thr Asp
                325                 330                 335
Gly Thr Ala Glu Leu Thr Thr Thr Ala Ala Thr Arg Phe Met Lys Asp
                340                 345                 350
Leu Tyr Phe Thr Ser Thr Asn Gly Val Gly Glu Ile Gly Arg Gly Ile
                355                 360                 365
Ala Leu Thr Leu Phe Asn Leu Ala Asp Thr Leu Leu Gly Gly Leu Pro
                370                 375                 380
Thr Glu Leu Ile Ser Ser Ala Gly Gly Gln Leu Phe Tyr Ser Arg Pro
385                 390                 395                 400
Val Val Ser Ala Asn Gly Glu Pro Thr Val Lys Leu Tyr Thr Ser Val
                405                 410                 415
Glu Asn Ala Gln Gln Asp Lys Gly Ile Ala Ile Pro His Asp Ile Asp
                420                 425                 430
Leu Gly Glu Ser Arg Val Val Ile Gln Asp Tyr Asp Asn Gln His Glu
                435                 440                 445
Gln Asp Arg Pro Thr Pro Ser Pro Ala Pro Ser Arg Pro Phe Ser Val
                450                 455                 460
Leu Arg Ala Asn Asp Val Leu Trp Leu Ser Leu Thr Ala Ala Glu Tyr
465                 470                 475                 480
Asp Gln Ser Thr Tyr Gly Ser Ser Thr Gly Pro Val Tyr Val Ser Asp
                485                 490                 495
Ser Val Thr Leu Val Asn Val Ala Thr Gly Ala Gln Ala Val Ala Arg
                500                 505                 510
Ser Leu Asp Trp Thr Lys Val Thr Leu Asp Gly Arg Pro Leu Ser Thr
                515                 520                 525
Ile Gln Gln Tyr Cys Lys Thr Phe Phe Val Leu Pro Leu Arg Gly Lys
                530                 535                 540
Leu Ser Phe Trp Glu Ala Gly Thr Thr Lys Ala Gly Tyr Pro Tyr Asn
545                 550                 555                 560
Tyr Asn Thr Thr Ala Ser Asp Gln Leu Leu Val Glu Asn Ala Ala Gly
                565                 570                 575
His Arg Val Ala Ile Ser Thr Tyr Thr Thr Ser Leu Gly Ala Gly Pro
                580                 585                 590
Val Ser Ile Ser Ala Val Ala Val Leu Ala Pro His Ser Ala Leu Ala
                595                 600                 605
Leu Leu Glu Asp Thr Met Asp Tyr Pro Ala Arg Ala His Thr Phe Asp
                610                 615                 620
Asp Phe Cys Pro Glu Cys Arg Pro Leu Gly Leu Gln Gly Cys Ala Phe
625                 630                 635                 640
Gln Ser Thr Val Ala Glu Leu Gln Arg Leu Lys Met Lys Val Gly Lys
                645                 650                 655
Thr Arg Glu Leu
                660
```

-continued

<210> SEQ ID NO 53
<211> LENGTH: 660
<212> TYPE: PRT
<213> ORGANISM: Hepatitis E virus

<400> SEQUENCE: 53

```
Met Arg Pro Arg Pro Ile Leu Leu Leu Leu Leu Met Phe Leu Pro Met
  1               5                  10                  15

Leu Pro Ala Pro Pro Pro Gly Gln Pro Ser Gly Arg Arg Arg Gly Arg
            20                  25                  30

Arg Ser Gly Gly Ser Gly Gly Gly Phe Trp Gly Asp Arg Val Asp Ser
        35                  40                  45

Gln Pro Phe Ala Ile Pro His Ile His Pro Thr Asn Pro Phe Ala Pro
    50                  55                  60

Asp Val Thr Ala Ala Ala Gly Ala Gly Pro Arg Val Arg Gln Pro Ala
 65                  70                  75                  80

Arg Pro Leu Gly Ser Ala Trp Arg Asp Gln Ala Gln Arg Pro Ala Ala
                85                  90                  95

Thr Ser Arg Arg Arg Pro Thr Thr Ala Gly Ala Ala Pro Leu Thr Ala
            100                 105                 110

Val Ala Pro Ala His Asp Thr Pro Pro Val Pro Asp Val Asp Ser Arg
        115                 120                 125

Gly Ala Ile Leu Arg Arg Gln Tyr Asn Leu Ser Thr Ser Pro Leu Thr
    130                 135                 140

Ser Pro Val Ala Thr Gly Thr Asn Leu Val Leu Tyr Ala Ala Pro Leu
145                 150                 155                 160

Ser Pro Leu Leu Pro Leu Gln Asp Gly Thr Asn Thr His Ile Met Ala
                165                 170                 175

Thr Glu Ala Ser Asn Tyr Ala Gln Tyr Arg Val Ala Arg Ala Thr Ile
            180                 185                 190

Arg Tyr Arg Pro Leu Val Pro Asn Ala Val Gly Gly Tyr Ala Ile Ser
        195                 200                 205

Ile Ser Phe Trp Pro Gln Thr Thr Thr Thr Pro Thr Ser Val Asp Met
    210                 215                 220

Asn Ser Ile Thr Ser Thr Asp Val Arg Ile Leu Val Gln Pro Gly Ile
225                 230                 235                 240

Ala Ser Glu Leu Val Ile Pro Ser Glu Arg Leu His Tyr Arg Asn Gln
                245                 250                 255

Gly Trp Arg Ser Val Glu Thr Ser Gly Val Ala Glu Glu Glu Ala Thr
            260                 265                 270

Ser Gly Leu Val Met Leu Cys Ile His Gly Leu Pro Val Asn Ser Tyr
        275                 280                 285

Thr Asn Thr Pro Tyr Thr Gly Ala Leu Gly Leu Leu Asp Phe Ala Leu
    290                 295                 300

Glu Phe Glu Phe Arg Asn Leu Thr Pro Gly Asn Thr Asn Thr Arg Val
305                 310                 315                 320

Ser Arg Tyr Ser Ser Thr Ala Arg His Arg Leu Arg Arg Gly Ala Asp
                325                 330                 335

Gly Thr Ala Glu Leu Thr Thr Thr Ala Ala Thr Arg Phe Met Lys Asp
            340                 345                 350

Leu Tyr Phe Thr Ser Thr Asn Gly Val Gly Glu Ile Gly Arg Gly Ile
        355                 360                 365

Ala Leu Thr Leu Phe Asn Leu Ala Asp Thr Leu Leu Gly Gly Leu Pro
```

-continued

```
            370                 375                 380
Thr Glu Leu Ile Ser Ser Ala Gly Gly Gln Leu Phe Tyr Ser Arg Pro
385                 390                 395                 400
Val Val Ser Ala Asn Gly Glu Pro Thr Val Lys Leu Tyr Thr Ser Val
                405                 410                 415
Glu Asn Ala Gln Gln Asp Lys Gly Ile Ala Ile Pro His Asp Ile Asp
                420                 425                 430
Leu Gly Glu Ser Arg Val Val Ile Gln Asp Tyr Asp Asn Gln His Glu
                435                 440                 445
Gln Asp Arg Pro Thr Pro Ser Pro Ala Pro Ser Arg Pro Phe Ser Val
                450                 455                 460
Leu Arg Ala Asn Asp Val Leu Trp Leu Ser Leu Thr Ala Ala Glu Tyr
465                 470                 475                 480
Asp Gln Ser Thr Tyr Gly Ser Ser Thr Gly Pro Val Tyr Val Ser Asp
                485                 490                 495
Ser Val Thr Leu Val Asn Val Ala Thr Gly Ala Gln Ala Val Ala Arg
                500                 505                 510
Ser Leu Asp Trp Thr Lys Val Thr Leu Asp Gly Arg Pro Leu Ser Thr
                515                 520                 525
Ile Gln Gln Tyr Ser Lys Thr Phe Phe Val Leu Pro Leu Arg Gly Lys
                530                 535                 540
Leu Ser Phe Trp Glu Ala Gly Thr Thr Lys Ala Gly Tyr Pro Tyr Asn
545                 550                 555                 560
Tyr Asn Thr Thr Ala Ser Asp Gln Leu Leu Ile Glu Asn Ala Ala Gly
                565                 570                 575
His Arg Val Ala Ile Ser Thr Tyr Thr Thr Ser Leu Gly Ala Gly Pro
                580                 585                 590
Val Ala Ile Ser Ala Val Ala Val Leu Ala Pro His Ser Ala Leu Ala
                595                 600                 605
Leu Leu Glu Asp Thr Met Asp Tyr Pro Ala Arg Ala His Thr Phe Asp
                610                 615                 620
Asp Phe Cys Pro Glu Cys Arg Pro Leu Gly Leu Gln Gly Cys Ala Phe
625                 630                 635                 640
Gln Ser Thr Val Ala Glu Leu Gln Arg Leu Lys Met Lys Val Gly Lys
                645                 650                 655
Thr Arg Glu Leu
                660

<210> SEQ ID NO 54
<211> LENGTH: 660
<212> TYPE: PRT
<213> ORGANISM: Hepatitis E virus

<400> SEQUENCE: 54

Met Gly Pro Arg Pro Ile Leu Leu Leu Phe Leu Met Phe Leu Pro Met
1               5                   10                  15
Leu Leu Ala Pro Pro Gly Pro Ser Gly Arg Arg Gly Arg
                20                  25                  30
Arg Ser Gly Gly Ser Gly Gly Gly Phe Trp Gly Asp Arg Val Asp Ser
                35                  40                  45
Gln Pro Phe Ala Ile Pro Tyr Ile His Pro Thr Asn Pro Phe Ala Pro
        50                  55                  60
Asn Val Thr Ala Ala Ala Gly Ala Gly Pro Arg Val Arg Gln Pro Val
65                  70                  75                  80
```

-continued

```
Arg Pro Leu Gly Ser Ala Trp Arg Asp Gln Ala Gln Arg Pro Ala Ala
                85                  90                  95

Ala Ser Arg Arg Arg Pro Thr Thr Ala Gly Ala Ala Pro Leu Thr Ala
            100                 105                 110

Val Ala Pro Ala His Asp Thr Pro Val Pro Asp Val Asp Ser Arg
        115                 120                 125

Gly Ala Ile Leu Arg Arg Gln Tyr Asn Leu Ser Thr Ser Pro Leu Thr
    130                 135                 140

Ser Ser Val Ala Thr Gly Thr Asn Leu Val Leu Tyr Ala Ala Pro Leu
145                 150                 155                 160

Ser Pro Leu Leu Pro Leu Gln Asp Gly Thr Asn Thr His Ile Met Ala
                165                 170                 175

Thr Glu Ala Ser Asn Tyr Ala Gln Tyr Arg Val Ala Arg Ala Thr Ile
            180                 185                 190

Arg Tyr Arg Pro Leu Val Pro Asn Ala Val Gly Gly Tyr Ala Ile Ser
        195                 200                 205

Ile Ser Phe Trp Pro Gln Thr Thr Pro Thr Pro Thr Ser Val Asp Met
    210                 215                 220

Asn Ser Ile Thr Ser Thr Asp Val Arg Ile Leu Val Gln Pro Gly Ile
225                 230                 235                 240

Ala Ser Glu Leu Val Ile Pro Ser Glu Arg Leu His Tyr Arg Asn Gln
                245                 250                 255

Gly Trp Arg Ser Val Glu Thr Ser Gly Val Ala Glu Glu Ala Thr
            260                 265                 270

Ser Gly Leu Val Met Leu Cys Ile His Gly Ser Pro Val Asn Ser Tyr
        275                 280                 285

Thr Asn Thr Pro Tyr Thr Gly Ala Leu Gly Leu Leu Asp Phe Ala Leu
    290                 295                 300

Glu Leu Glu Phe Arg Asn Leu Thr Pro Gly Asn Thr Asn Thr Arg Val
305                 310                 315                 320

Ser Arg Tyr Ser Ser Thr Ala Arg His Arg Leu Arg Arg Gly Ala Asp
                325                 330                 335

Gly Thr Ala Glu Leu Thr Thr Ala Ala Thr Arg Phe Met Lys Asp
            340                 345                 350

Leu Tyr Phe Thr Ser Thr Asn Gly Val Gly Glu Ile Gly Arg Gly Ile
        355                 360                 365

Ala Leu Thr Leu Phe Asn Leu Ala Asp Thr Leu Leu Gly Gly Leu Pro
    370                 375                 380

Thr Glu Leu Ile Ser Ser Ala Gly Gly Gln Leu Phe Tyr Ser Arg Pro
385                 390                 395                 400

Val Val Ser Ala Asn Gly Glu Pro Thr Val Lys Leu Tyr Thr Ser Val
                405                 410                 415

Glu Asn Ala Gln Gln Asp Lys Gly Ile Ala Ile Pro Asn Asp Ile Asp
            420                 425                 430

Leu Gly Glu Ser Arg Val Val Ile Gln Asp Tyr Asp Asn Gln His Glu
        435                 440                 445

Gln Asp Arg Pro Thr Pro Ser Pro Ala Pro Ser Arg Pro Phe Ser Val
    450                 455                 460

Leu Arg Ala Asn Asp Val Leu Trp Leu Ser Leu Thr Ala Ala Glu Tyr
465                 470                 475                 480

Asp Gln Ser Thr Tyr Gly Ser Ser Thr Gly Pro Val Tyr Val Ser Asp
                485                 490                 495

Ser Val Thr Leu Val Asn Val Ala Thr Gly Ala Gln Ala Val Ala Arg
```

-continued

```
                500                 505                 510
Ser Leu Asp Trp Thr Lys Val Thr Leu Asp Gly Arg Pro Leu Ser Thr
            515                 520                 525

Ile Gln Gln Tyr Ser Lys Ile Phe Phe Val Leu Pro Leu Arg Gly Lys
            530                 535                 540

Leu Ser Phe Trp Glu Ala Gly Thr Thr Arg Pro Gly Tyr Pro Tyr Asn
545                 550                 555                 560

Tyr Asn Thr Thr Ala Ser Asp Gln Leu Leu Val Glu Asn Ala Ala Gly
                565                 570                 575

His Arg Val Ala Ile Ser Thr Tyr Thr Thr Ser Leu Gly Ala Gly Pro
            580                 585                 590

Val Ser Ile Ser Ala Val Ala Val Leu Gly Pro His Ser Ala Leu Ala
            595                 600                 605

Leu Leu Glu Asp Thr Leu Asp Tyr Pro Ala Arg Ala His Thr Phe Asp
            610                 615                 620

Asp Phe Cys Pro Glu Cys Arg Pro Leu Gly Leu Gln Gly Cys Ala Phe
625                 630                 635                 640

Gln Ser Thr Val Ala Glu Leu Gln Arg Leu Lys Met Lys Val Gly Lys
                645                 650                 655

Thr Arg Glu Leu
            660
```

<210> SEQ ID NO 55
<211> LENGTH: 660
<212> TYPE: PRT
<213> ORGANISM: Hepatitis E virus

<400> SEQUENCE: 55

```
Met Arg Pro Arg Pro Ile Leu Leu Leu Leu Met Phe Leu Pro Met
1               5                   10                  15

Leu Pro Ala Pro Pro Gly Gln Pro Ser Gly Arg Arg Gly Arg
            20                  25                  30

Arg Ser Gly Gly Ser Gly Gly Gly Phe Trp Gly Asp Arg Val Asp Ser
            35                  40                  45

Gln Pro Phe Ala Ile Pro Tyr Ile His Pro Thr Asn Pro Phe Ala Pro
        50                  55                  60

Asp Val Thr Ala Ala Ala Gly Ala Gly Pro Arg Val Arg Gln Pro Ala
65                  70                  75                  80

Arg Pro Leu Gly Ser Ala Trp Arg Asp Gln Ala Gln Arg Pro Ala Val
                85                  90                  95

Ala Ser Arg Arg Arg Pro Thr Thr Ala Gly Ala Ala Pro Leu Thr Ala
            100                 105                 110

Val Ala Pro Ala His Asp Thr Pro Val Pro Asp Val Asp Ser Arg
            115                 120                 125

Ala Ala Ile Leu Arg Arg Gln Tyr Asn Leu Ser Thr Ser Pro Leu Thr
        130                 135                 140

Ser Ser Val Ala Thr Gly Thr Asn Leu Val Leu Tyr Ala Ala Pro Leu
145                 150                 155                 160

Ser Pro Leu Leu Pro Leu Gln Asp Gly Thr Asn Thr His Ile Met Ala
                165                 170                 175

Thr Glu Ala Ser Asn Tyr Ala Gln Tyr Arg Val Val Arg Ala Thr Ile
            180                 185                 190

Arg Tyr Arg Pro Leu Val Pro Asn Ala Val Gly Gly Tyr Ala Ile Ser
        195                 200                 205
```

-continued

```
Ile Ser Phe Trp Pro Gln Thr Thr Thr Pro Thr Ser Val Asp Met
    210                 215                 220
Asn Ser Ile Thr Ser Thr Asp Val Arg Ile Leu Val Gln Pro Gly Ile
225                 230                 235                 240
Ala Ser Glu Leu Val Ile Pro Ser Glu Arg Leu His Tyr Arg Asn Gln
                245                 250                 255
Gly Trp Arg Ser Val Glu Thr Ser Gly Val Ala Glu Glu Ala Thr
            260                 265                 270
Ser Gly Leu Val Met Leu Cys Ile His Gly Ser Pro Val Asn Ser Tyr
        275                 280                 285
Thr Asn Thr Pro Tyr Thr Gly Ala Leu Gly Leu Leu Asp Phe Ala Leu
    290                 295                 300
Glu Leu Glu Phe Arg Asn Leu Thr Pro Gly Asn Thr Asn Thr Arg Val
305                 310                 315                 320
Ser Arg Tyr Ser Ser Thr Ala Arg His Arg Leu Arg Arg Gly Ala Asp
                325                 330                 335
Gly Thr Ala Glu Leu Thr Thr Thr Ala Ala Thr Arg Phe Met Lys Asp
            340                 345                 350
Leu Tyr Phe Thr Ser Thr Asn Gly Val Gly Glu Ile Gly Arg Gly Ile
        355                 360                 365
Ala Leu Thr Leu Phe Asn Leu Ala Asp Thr Leu Leu Gly Gly Leu Pro
    370                 375                 380
Thr Glu Leu Ile Ser Ser Ala Gly Gly Gln Leu Phe Tyr Ser Arg Pro
385                 390                 395                 400
Val Val Ser Ala His Gly Glu Pro Thr Val Lys Leu Tyr Thr Ser Val
                405                 410                 415
Glu Asn Ala Gln Gln Asp Lys Gly Ile Ala Ile Pro His Asp Ile Asp
            420                 425                 430
Leu Gly Glu Ser Arg Val Val Ile Gln Asp Tyr Asp Asn Gln His Glu
        435                 440                 445
Gln Asp Arg Pro Thr Pro Ser Pro Ala Pro Ser Arg Pro Phe Ser Val
    450                 455                 460
Leu Arg Ala Asn Asp Val Leu Trp Leu Ser Leu Thr Ala Ala Glu Tyr
465                 470                 475                 480
Asp Gln Ser Thr Tyr Gly Ser Ser Thr Ala Pro Val Tyr Val Ser Asp
                485                 490                 495
Ser Val Thr Leu Val Asn Val Ala Thr Gly Ala Gln Ala Val Ala Arg
            500                 505                 510
Ser Leu Asp Trp Thr Lys Val Thr Leu Asp Gly Arg Pro Leu Ser Thr
        515                 520                 525
Ile Gln Gln Tyr Pro Lys Thr Phe Val Leu Pro Leu Arg Gly Lys
    530                 535                 540
Leu Ser Phe Trp Glu Ala Gly Thr Thr Lys Ala Gly Tyr Pro Tyr Asn
545                 550                 555                 560
Tyr Asn Thr Thr Ala Ser Asp Gln Leu Leu Val Glu Asn Ala Ala Gly
                565                 570                 575
His Arg Val Ala Ile Ser Thr Tyr Thr Thr Ser Leu Gly Ala Gly Pro
            580                 585                 590
Val Ser Ile Ser Ala Val Ala Val Leu Ala Pro His Ser Ala Leu Ala
        595                 600                 605
Leu Leu Glu Asp Thr Leu Asp Tyr Pro Ala Cys Ala His Thr Phe Asp
    610                 615                 620
Asp Phe Cys Pro Glu Cys Arg Pro Leu Gly Leu Gln Gly Cys Ala Phe
```

```
                625                 630                 635                 640
Gln Ser Thr Val Ala Glu Leu Gln Arg Leu Lys Met Lys Val Gly Lys
                        645                 650                 655

Thr Arg Glu Leu
            660

<210> SEQ ID NO 56
<211> LENGTH: 660
<212> TYPE: PRT
<213> ORGANISM: Hepatitis E virus

<400> SEQUENCE: 56

Met Arg Pro Arg Pro Ile Leu Leu Leu Leu Met Phe Leu Pro Met
  1               5                  10                  15

Leu Pro Ala Pro Pro Gly Gln Pro Ser Gly Arg Arg Gly Arg
                 20                  25                  30

Arg Ser Gly Gly Ser Gly Gly Phe Trp Gly Asp Arg Ala Asp Ser
            35                  40                  45

Gln Pro Phe Ala Ile Pro Tyr Ile His Pro Thr Asn Pro Phe Ala Pro
     50                  55                  60

Asp Val Thr Ala Ala Gly Ala Gly Pro Arg Val Arg Gln Pro Ala
 65                  70                  75                  80

Arg Pro Leu Gly Ser Ala Trp Arg Asp Gln Ala Gln Arg Pro Ala Ala
                 85                  90                  95

Ala Ser Arg Arg Pro Thr Thr Ala Gly Ala Ala Pro Leu Thr Ala
            100                 105                 110

Val Ala Pro Ala His Asp Thr Pro Val Pro Asp Val Asp Ser Arg
        115                 120                 125

Gly Ala Ile Leu Arg Arg Gln Tyr Asn Leu Ser Thr Ser Pro Leu Thr
        130                 135                 140

Ser Ser Val Ala Thr Gly Thr Asn Leu Val Leu Tyr Ala Ala Pro Leu
145                 150                 155                 160

Ser Pro Leu Leu Pro Leu Gln Asp Gly Thr Asn Thr His Ile Met Ala
                165                 170                 175

Thr Glu Ala Ser Asn Tyr Ala Gln Tyr Arg Val Val Arg Ala Thr Ile
            180                 185                 190

Arg Tyr Arg Pro Leu Val Pro Asn Ala Val Gly Gly Tyr Ala Ile Ser
        195                 200                 205

Ile Ser Phe Trp Pro Gln Thr Thr Thr Pro Thr Ser Val Asp Met
        210                 215                 220

Asn Ser Ile Thr Ser Thr Asp Val Arg Ile Leu Val Gln Pro Gly Ile
225                 230                 235                 240

Ala Ser Glu His Val Ile Pro Ser Glu Arg Leu His Tyr Arg Asn Gln
                245                 250                 255

Gly Trp Arg Ser Val Glu Thr Ser Gly Val Ala Glu Glu Ala Thr
            260                 265                 270

Ser Gly Leu Val Met Leu Cys Ile His Gly Ser Leu Val Asn Ser Tyr
        275                 280                 285

Thr Asn Thr Pro Tyr Thr Gly Ala Leu Gly Leu Leu Asp Phe Ala Leu
        290                 295                 300

Glu Leu Glu Phe Arg Asn Leu Thr Pro Gly Asn Thr Asn Thr Arg Val
305                 310                 315                 320

Ser Arg Tyr Ser Ser Thr Ala Arg His Arg Leu Arg Arg Gly Ala Asp
                325                 330                 335
```

```
Gly Thr Ala Glu Leu Thr Thr Thr Ala Ala Thr Arg Phe Met Lys Asp
            340                 345                 350

Leu Tyr Phe Thr Ser Thr Asn Gly Val Gly Glu Ile Gly Arg Gly Ile
            355                 360                 365

Ala Leu Thr Leu Phe Asn Leu Ala Asp Thr Leu Leu Gly Gly Leu Pro
            370                 375                 380

Thr Glu Leu Ile Ser Ser Ala Gly Gly Gln Leu Phe Tyr Ser Arg Pro
385                 390                 395                 400

Val Val Ser Ala Asn Gly Glu Pro Thr Val Lys Leu Tyr Thr Ser Val
                405                 410                 415

Glu Asn Ala Gln Gln Asp Lys Gly Ile Ala Ile Pro His Asp Ile Asp
            420                 425                 430

Leu Gly Glu Ser Arg Val Val Ile Gln Asp Tyr Asp Asn Gln His Glu
            435                 440                 445

Gln Asp Arg Pro Thr Pro Ser Pro Ala Pro Ser Arg Pro Phe Ser Val
            450                 455                 460

Leu Arg Ala Asn Asp Val Leu Trp Leu Ser Leu Thr Ala Ala Glu Tyr
465                 470                 475                 480

Asp Gln Ser Thr Tyr Gly Ser Ser Thr Gly Pro Val Tyr Val Ser Asp
                485                 490                 495

Ser Val Thr Leu Val Asn Val Ala Thr Gly Ala Gln Ala Val Ala Arg
            500                 505                 510

Ser Leu Asp Trp Thr Lys Val Thr Leu Asp Gly Arg Pro Leu Ser Thr
            515                 520                 525

Thr Gln Gln Tyr Ser Lys Thr Phe Phe Val Leu Pro Leu Arg Gly Lys
            530                 535                 540

Leu Ser Phe Trp Glu Ala Gly Thr Thr Lys Ala Gly Tyr Pro Tyr Asn
545                 550                 555                 560

Tyr Asn Thr Thr Ala Ser Asp Gln Leu Leu Val Glu Asn Ala Ala Gly
                565                 570                 575

His Arg Val Ala Ile Ser Thr Tyr Thr Thr Ser Leu Gly Ala Gly Pro
            580                 585                 590

Val Ser Ile Ser Ala Val Ala Val Leu Ala Pro His Ser Ala Leu Ala
            595                 600                 605

Leu Leu Glu Asp Thr Met Asp Tyr Pro Ala Arg Ala His Thr Phe Asp
            610                 615                 620

Asp Phe Cys Pro Glu Cys Arg Pro Leu Gly Leu Gln Gly Cys Ala Phe
625                 630                 635                 640

Gln Ser Thr Val Ala Glu Leu Gln Arg Leu Lys Met Lys Val Gly Lys
                645                 650                 655

Thr Arg Glu Leu
            660

<210> SEQ ID NO 57
<211> LENGTH: 660
<212> TYPE: PRT
<213> ORGANISM: Hepatitis E virus

<400> SEQUENCE: 57

Met Arg Pro Arg Ala Val Leu Leu Leu Phe Val Leu Leu Pro Met
 1               5                  10                  15

Leu Pro Ala Pro Pro Ala Gly Gln Pro Ser Gly Arg Arg Cys Gly Arg
                20                  25                  30

Arg Asn Gly Gly Ala Gly Gly Gly Phe Trp Gly Asp Arg Val Asp Ser
            35                  40                  45
```

```
Gln Pro Phe Ala Leu Pro Tyr Ile His Pro Thr Asn Pro Phe Ala Ala
     50                  55                  60

Asp Val Val Ser Gln Pro Gly Ala Gly Asp Arg Pro Arg Gln Pro Pro
 65                  70                  75                  80

Arg Pro Leu Gly Ser Ala Trp Arg Asp Gln Ser Gln Arg Pro Ser Thr
                 85                  90                  95

Ala Pro Arg Arg Arg Ser Ala Pro Ala Gly Ala Ala Pro Leu Thr Ala
                100                 105                 110

Val Ser Pro Ala Pro Asp Thr Ala Pro Val Pro Asp Val Asp Ser Arg
            115                 120                 125

Gly Ala Ile Leu Arg Arg Gln Tyr Asn Leu Ser Thr Ser Pro Leu Thr
        130                 135                 140

Ser Ser Val Ala Ala Gly Thr Asn Leu Val Leu Tyr Ala Ala Pro Leu
145                 150                 155                 160

Asn Pro Leu Leu Pro Leu Gln Asp Gly Thr Asn Thr His Ile Met Ala
                165                 170                 175

Thr Glu Ala Ser Asn Tyr Ala Gln Tyr Arg Val Val Arg Ala Thr Ile
                180                 185                 190

Arg Tyr Arg Pro Leu Val Pro Asn Ala Val Gly Gly Tyr Ala Ile Ser
        195                 200                 205

Ile Ser Phe Trp Pro Gln Thr Thr Thr Pro Thr Ser Val Asp Met
210                 215                 220

Asn Ser Ile Thr Ser Thr Asp Val Arg Ile Leu Val Gln Pro Gly Ile
225                 230                 235                 240

Ala Ser Glu Leu Val Ile Pro Ser Glu Arg Leu His Tyr Arg Asn Gln
                245                 250                 255

Gly Trp Arg Ser Val Glu Thr Thr Gly Val Ala Glu Glu Ala Thr
                260                 265                 270

Ser Gly Leu Val Met Leu Cys Ile His Gly Ser Pro Val Asn Ser Tyr
        275                 280                 285

Thr Asn Thr Pro Tyr Thr Gly Ala Leu Gly Leu Leu Asp Phe Ala Leu
    290                 295                 300

Glu Leu Glu Phe Arg Asn Leu Thr Pro Gly Asn Thr Asn Thr Arg Val
305                 310                 315                 320

Ser Arg Tyr Thr Ser Thr Ala Arg His Arg Leu Arg Arg Gly Ala Asp
                325                 330                 335

Gly Thr Ala Glu Leu Thr Thr Thr Ala Ala Thr Arg Phe Met Lys Asp
            340                 345                 350

Leu His Phe Thr Gly Thr Asn Gly Val Gly Glu Val Gly Arg Gly Ile
        355                 360                 365

Ala Leu Thr Leu Phe Asn Leu Ala Asp Thr Leu Leu Gly Gly Leu Pro
    370                 375                 380

Thr Glu Leu Ile Ser Ser Ala Gly Gly Gln Leu Phe Tyr Ser Arg Pro
385                 390                 395                 400

Val Val Ser Ala Asn Gly Glu Pro Thr Val Lys Leu Tyr Thr Ser Val
                405                 410                 415

Glu Asn Ala Gln Gln Asp Lys Gly Ile Thr Ile Pro His Asp Ile Asp
                420                 425                 430

Leu Gly Asp Ser Arg Val Val Ile Gln Asp Tyr Asp Asn Gln His Glu
            435                 440                 445

Gln Asp Arg Pro Thr Pro Ser Pro Ala Pro Ser Arg Pro Phe Ser Val
        450                 455                 460
```

```
Leu Arg Ala Asn Asp Val Leu Trp Leu Ser Leu Thr Ala Ala Glu Tyr
465                 470                 475                 480

Asp Gln Thr Thr Tyr Gly Ser Ser Thr Asn Pro Met Tyr Val Ser Asp
            485                 490                 495

Thr Val Thr Leu Val Asn Val Ala Thr Gly Ala Gln Ala Val Ala Arg
            500                 505                 510

Ser Leu Asp Trp Ser Lys Val Thr Leu Asp Gly Arg Pro Leu Thr Thr
            515                 520                 525

Ile Gln Gln Tyr Ser Lys Thr Tyr Phe Val Leu Pro Leu Arg Gly Lys
            530                 535                 540

Leu Ser Phe Trp Glu Ala Gly Thr Thr Lys Ala Gly Tyr Pro Tyr Asn
545                 550                 555                 560

Tyr Asn Thr Thr Ala Ser Asp Gln Ile Leu Ile Glu Asn Ala Ala Gly
            565                 570                 575

His Arg Val Ala Ile Ser Thr Tyr Thr Thr Ser Leu Gly Ala Gly Pro
            580                 585                 590

Thr Ser Ile Ser Ala Val Gly Val Leu Ala Pro His Ser Ala Leu Ala
            595                 600                 605

Val Leu Glu Asp Thr Val Asp Tyr Pro Ala Arg Ala His Thr Phe Asp
            610                 615                 620

Asp Phe Cys Pro Glu Cys Arg Thr Leu Gly Leu Gln Gly Cys Ala Phe
625                 630                 635                 640

Gln Ser Thr Ile Ala Glu Leu Gln Arg Leu Lys Met Lys Val Gly Lys
            645                 650                 655

Thr Arg Glu Ser
            660

<210> SEQ ID NO 58
<211> LENGTH: 123
<212> TYPE: PRT
<213> ORGANISM: Hepatitis E virus

<400> SEQUENCE: 58

Met Asn Asn Met Trp Phe Ala Ala Pro Met Gly Ser Pro Pro Cys Ala
 1               5                  10                  15

Leu Gly Leu Phe Cys Cys Cys Ser Ser Cys Phe Cys Leu Cys Cys Pro
            20                  25                  30

Arg His Arg Pro Val Ser Arg Leu Ala Ala Val Val Gly Gly Ala Ala
            35                  40                  45

Ala Val Pro Ala Val Val Ser Gly Val Thr Gly Leu Ile Leu Ser Pro
     50                  55                  60

Ser Gln Ser Pro Ile Phe Ile Gln Pro Thr Pro Leu Pro Gln Thr Leu
65                  70                  75                  80

Pro Leu Arg Pro Gly Leu Asp Leu Ala Phe Ala Asn Gln Pro Gly His
            85                  90                  95

Leu Ala Pro Leu Gly Glu Ile Arg Pro Ser Ala Pro Leu Pro Pro
            100                 105                 110

Val Ala Asp Leu Pro Gln Pro Gly Leu Arg Arg
            115                 120

<210> SEQ ID NO 59
<211> LENGTH: 123
<212> TYPE: PRT
<213> ORGANISM: Hepatitis E virus

<400> SEQUENCE: 59
```

-continued

```
Met Asn Asn Met Ser Phe Ala Ala Pro Met Gly Pro Arg Pro Cys Ala
 1               5                  10                  15

Leu Gly Leu Phe Cys Cys Cys Ser Ser Cys Phe Cys Leu Cys Cys Pro
            20                  25                  30

Arg His Arg Pro Val Ser Arg Leu Ala Ala Val Val Gly Gly Ala Ala
            35                  40                  45

Ala Val Pro Ala Val Val Ser Gly Val Thr Gly Leu Ile Leu Ser Pro
     50                  55                  60

Ser Gln Ser Pro Ile Phe Ile Gln Pro Thr Pro Ser Pro Pro Met Ser
 65                  70                  75                  80

Pro Leu Arg Pro Gly Leu Asp Leu Val Phe Ala Asn Pro Ser Asp His
                85                  90                  95

Ser Ala Pro Leu Gly Val Thr Arg Pro Ser Ala Pro Pro Leu Pro His
            100                 105                 110

Val Val Asp Leu Pro Gln Leu Gly Pro Arg Arg
            115                 120
```

<210> SEQ ID NO 60
<211> LENGTH: 123
<212> TYPE: PRT
<213> ORGANISM: Hepatitis E virus

<400> SEQUENCE: 60

```
Met Asn Asn Met Ser Phe Ala Ala Pro Met Gly Ser Arg Pro Cys Asp
 1               5                  10                  15

Leu Gly Leu Phe Cys Cys Cys Ser Ser Cys Phe Cys Leu Cys Cys Pro
            20                  25                  30

Arg His Arg Pro Val Ser Arg Leu Ala Ala Val Val Gly Gly Ala Ala
            35                  40                  45

Ala Val Pro Ala Val Val Ser Gly Val Thr Gly Leu Ile Leu Ser Pro
     50                  55                  60

Ser Gln Ser Pro Ile Phe Ile Gln Pro Thr Pro Ser Pro Pro Met Ser
 65                  70                  75                  80

Pro Leu Arg Pro Gly Leu Asp Leu Val Phe Ala Asn Gln Pro Asp His
                85                  90                  95

Ser Ala Pro Leu Gly Val Thr Arg Pro Ser Ala Pro Pro Leu Pro His
            100                 105                 110

Val Val Asp Leu Pro Gln Leu Gly Pro Arg Arg
            115                 120
```

<210> SEQ ID NO 61
<211> LENGTH: 123
<212> TYPE: PRT
<213> ORGANISM: Hepatitis E virus

<400> SEQUENCE: 61

```
Met Asn Asn Met Ser Phe Ala Ala Pro Met Gly Ser Arg Pro Cys Ala
 1               5                  10                  15

Leu Gly Leu Phe Cys Cys Cys Ser Ser Cys Phe Cys Leu Cys Cys Pro
            20                  25                  30

Arg His Arg Pro Val Ser Arg Leu Ala Ala Val Val Gly Gly Ala Ala
            35                  40                  45

Ala Val Pro Ala Val Val Ser Gly Val Thr Gly Leu Ile Leu Ser Pro
     50                  55                  60

Ser Gln Ser Pro Ile Phe Ile Gln Pro Thr Pro Leu Pro Pro Met Ser
 65                  70                  75                  80
```

```
Pro Leu Arg Pro Gly Leu Asp Leu Ala Phe Ala Asn Pro Pro Asp His
                85                  90                  95

Ser Ala Pro Leu Gly Val Thr Arg Pro Ser Ala Pro Pro Leu Pro His
            100                 105                 110

Val Val Asp Leu Pro Gln Leu Gly Pro Arg Arg
        115                 120
```

<210> SEQ ID NO 62
<211> LENGTH: 123
<212> TYPE: PRT
<213> ORGANISM: Hepatitis E virus

<400> SEQUENCE: 62

```
Met Asn Asn Met Ser Phe Ala Ala Pro Met Gly Trp Arg Pro Cys Ala
 1               5                  10                  15

Leu Gly Leu Phe Cys Cys Cys Ser Ser Cys Phe Cys Leu Ser Cys Pro
                20                  25                  30

Arg His Arg Pro Val Ser Arg Leu Ala Ala Val Val Gly Gly Ala Ala
                35                  40                  45

Ala Val Pro Ala Val Val Ser Gly Val Thr Gly Leu Ile Leu Ser Pro
        50                  55                  60

Ser Gln Ser Pro Ile Phe Ile Gln Pro Thr Pro Ser Pro Pro Met Ser
65                  70                  75                  80

Pro Leu Arg Pro Gly Leu Asp Leu Val Phe Ala Asn Pro Pro Asp His
                85                  90                  95

Ser Ala Pro Leu Gly Val Thr Arg Pro Ser Ala Pro Pro Leu Pro His
            100                 105                 110

Val Val Asp Leu Pro Gln Leu Gly Pro Arg Arg
        115                 120
```

<210> SEQ ID NO 63
<211> LENGTH: 123
<212> TYPE: PRT
<213> ORGANISM: Hepatitis E virus

<400> SEQUENCE: 63

```
Met Asn Asn Met Ser Ser Ala Ala Pro Met Gly Ser Arg Pro Cys Ala
 1               5                  10                  15

Leu Gly Leu Phe Cys Cys Cys Ser Ser Cys Phe Cys Leu Cys Cys Pro
                20                  25                  30

Arg His Arg Pro Val Ser Arg Leu Ala Ala Val Gly Gly Ala Ala
                35                  40                  45

Ala Val Pro Ala Val Val Ser Gly Val Thr Gly Leu Ile Leu Ser Pro
        50                  55                  60

Ser Gln Ser Pro Ile Phe Ile Gln Pro Thr Pro Ser Pro Pro Met Ser
65                  70                  75                  80

Pro Leu Arg Pro Gly Leu Asp Leu Val Phe Ala Asn Pro Pro Asp His
                85                  90                  95

Ser Ala Pro Leu Gly Val Thr Arg Pro Ser Ala Pro Pro Leu Pro His
            100                 105                 110

Val Val Asp Leu Pro Gln Leu Gly Pro Arg Arg
        115                 120
```

<210> SEQ ID NO 64
<211> LENGTH: 123
<212> TYPE: PRT
<213> ORGANISM: Hepatitis E virus

```
<400> SEQUENCE: 64

Met Asp Asn Met Ser Phe Ala Ala Pro Met Gly Ser Arg Pro Trp Ala
 1               5                  10                  15

Leu Gly Leu Phe Cys Cys Cys Ser Ser Cys Phe Cys Leu Cys Cys Ser
             20                  25                  30

Arg His Arg Pro Val Ser Arg Leu Ala Ala Val Val Gly Gly Ala Ala
             35                  40                  45

Ala Val Pro Ala Val Val Ser Gly Val Thr Gly Leu Ile Leu Ser Pro
         50                  55                  60

Ser Gln Ser Pro Ile Phe Ile Gln Pro Thr Pro Ser Pro Arg Met Ser
 65                  70                  75                  80

Pro Leu Arg Pro Gly Leu Asp Leu Val Phe Ala Asn Pro Ser Asp His
             85                  90                  95

Ser Ala Pro Leu Gly Ala Thr Arg Pro Ser Ala Pro Pro Leu Pro His
            100                 105                 110

Val Val Asp Leu Pro Gln Leu Gly Pro Arg Arg
            115                 120

<210> SEQ ID NO 65
<211> LENGTH: 122
<212> TYPE: PRT
<213> ORGANISM: Hepatitis E virus

<400> SEQUENCE: 65

Met Asn Asn Met Ser Phe Ala Ser Pro Met Gly Ser Pro Cys Ala Leu
 1               5                  10                  15

Gly Leu Phe Cys Cys Cys Ser Ser Cys Phe Cys Leu Cys Cys Pro Arg
             20                  25                  30

His Arg Pro Ala Ser Arg Leu Ala Ala Val Val Gly Gly Ala Thr Ala
             35                  40                  45

Val Pro Ala Val Val Ser Gly Val Thr Gly Leu Ile Leu Ser Pro Ser
         50                  55                  60

Pro Ser Pro Ile Phe Ile Gln Pro Thr Pro Ser Leu Pro Met Ser Phe
 65                  70                  75                  80

His Asn Pro Gly Leu Glu Phe Ala Leu Asp Ser Arg Pro Ala Pro Leu
             85                  90                  95

Ala Pro Leu Gly Val Thr Ser Pro Ser Ala Pro Pro Leu Pro Pro Val
            100                 105                 110

Val Asp Leu Pro Gln Leu Gly Leu Arg Arg
            115                 120
```

SWINE HEPATITIS E VIRUS AND USES THEREOF

This application is a national stage of PCT/US98/14665 filed Jul. 17, 1998 which claims benefit of provisional appliction 60/053,069 filed Jul. 18, 1997.

FIELD OF THE INVENTION

Hepatitis E occurs predominantly in developing countries of Asia and Africa but has also been the cause of epidemics in Mexico (1). The disease generally affects young adults and has a very high mortality rate, up to 20%, in pregnant women (1–4). Hepatitis E has rarely been reported in developed countries, and most of those cases have been imported (1, 4–6). The causative agent, hepatitis E virus (HEV), is transmitted primarily by the fecal-oral route, often through contaminated water (1, 4). The availability of sensitive serological tests for HEV has permitted detailed assessment of the prevalence of HEV infection (7–8). In regions where HEV is endemic, anti-HEV antibodies have been detected in sera from convalescent individuals as well as from the general population (1, 3). Although hepatitis E is not endemic in the United States and other developed countries, anti-HEV was found in a significant proportion, up to 28% in some areas, of healthy individuals in these countries (7, 9). It is unclear if the anti-HEV detected in developed countries demonstrates infection with a non-pathogenic HEV strain or cross-reactivity with a related agent.

It has been reported that anti-HEV is acquired naturally in primates and swine (1, 10), suggesting that these species have been exposed to HEV or a related agent, and that hepatitis E may be a zoonotic disease. The role of swine in HEV transmission is not clear although domestic swine have been reported to be susceptible to infection with a human HEV strain (11). It would be advantageous to have an animal strain of HEV that could be studied in animals but would sufficiently resemble the human virus as to make the results of studies with the animal virus applicable to the human disease. It would be particularly advantageous to have an animal virus that could be useful in preparing vaccines and other medicaments for treatment of animals, especially humans.

BACKGROUND OF THE INVENTION

It has been reported that domestic swine can be experimentally infected with HEV (11), although this infection appears more severe in swine than in non-human primates. In our own examination, swine inoculated with human HEV remained clinically normal and we detected no antibody response to HEV. While it has been suggested that human feces from infected individuals are the primary source of infection for hepatitis E in humans, swine have been suggested as a possible animal reservoir and natural host for the virus. For example, in some geographical areas the prevalence of anti-HEV in swine is even higher than that found in humans and swine have been suggested as a possible year round reservoir for HEV (10). However, the occurrence of IgG anti-HEV in swine does not necessarily mean that HEV infection has occurred. Hepatitis E is not endemic in the United States and yet our own studies have indicated that the majority of swine 2 to 3 months of age in the midwestern United States have IgG anti-HEV. In addition, IgG anti-HEV is also found in a significant proportion of healthy humans in countries, including the United States, where hepatitis E is not endemic (7). Such data indicated to us that an agent or agents other than human HEV, but antigenically closely related to human HEV, exists within the swine population. The antibody induced by this putative agent has been shown to cross-react with a human HEV antigen used in serological testing. Such findings mean that caution must be used in interpreting serological data, especially from non-endemic regions. Identification of such a putative agent would, of course, be highly advantageous in order to develop more specific serological tests for HEV infection. The detection and isolation of such a virus from swine would also be desirable in determining the possible existence of an animal reservoir for HEV. In addition, such a virus, if capable of infecting swine but not causing illness, might be well suited for use as a vaccine or therapeutic agent for use in vaccinating and treating mammals, especially humans. Thus, such a virus could well serve as an attenuated live virus vaccine strain.

BRIEF SUMMARY OF THE INVENTION

The present invention is directed to a novel swine hepatitis E virus (swine HEV) strain in isolated form and with sufficient nucleotide sequence homology in its genome, and sufficient amino acid sequence homology in its capsid protein, both relative to human HEV, as to be highly useful in the evaluation of potential human infection by endogenous swine sources, including potential infection resulting from xenotransplantation, especially transplanting of swine organs and tissues into humans.

The swine hepatitis E virus of the present invention is also useful as a vaccine for vaccination of animals, preferably mammals, and most preferably humans, against infection by other strains of hepatitis E virus. The swine HEV of the present invention would, for example, be especially useful as a vaccine for use in humans to prevent possible infection by human hepatitis E virus (or HEV). The swine HEV of the present invention accomplishes this by providing only a subclinical infection on its own and thereby immunizing the subject animal, for example, a human, in, for example, a manner similar to that accomplished by cowpox virus in immunizing against smallpox.

The present invention also relates to use of a novel swine HEV as a therapeutic treatment for infection by other strains of HEV by injection of the virus of the invention to bolster the immune response of an infected animal while providing only a subclinical infection on its own.

The swine HEV of the present invention is also highly useful in the generation of bosh polyclonal and monoclonal antibodies which themselves find use as therapeutic agents for treatment of animals, especially mammals, and most especially humans, in need thereof.

The antibodies produced in response to the swine HEV of the present invention also find use in the development of in vitro diagnostic protocols for early detection of HEV infection in animals, especially mammals, and most especially humans.

The swine HEV of the present invention is particularly advantageous for use in the development of prophylactic, therapeutic and diagnostic agents for the prevention, treatment and detection of human HEV because it is not a human virus and thus can be handled both experimentally and clinically without fear of severe infection and/or contamination.

SPF swine were experimentally infected with the swine HEV of the present invention. Therefore, infection of swine with the swine HEV can provide an appropriate animal model for human HEV experiments.

BRIEF DESCRIPTION OF THE DRAWINGS

(FIG. 1A) a piglet born to a seropositive sow with a high titer of IgG anti-HEV; (FIG. 1B) a piglet born to a seropositive sow with a lower titer of IgG anti-HEV; (FIG. 1C) a piglet born to a seronegative sow. The ELISA absorbance value of IgG anti-HEV in breeder sows is shown at (S).

FIGS. 3A–3B. Alignment of amino acid sequences of Open Reading Frames 2 (orf 2) (at FIG. 3A) and orf 3 (at FIG. 3B) of swine HEV with human strains of HEV. The sequence of the Sar55 strain is shown at the top, and only differences between them are indicated. Deletions are indicated by (−). The putative hypervariable region (HVR) in the ORF3 is indicated by asterisks (*). The sequences used in this alignment were Burma: FIG. 3A—SEQ ID NO: 50; FIG. 3B—SEQ ID NO: 13 (14), Mexico: FIG. 3A—SEQ ID NO: 48; FIG. 3B—SEQ ID NO: 58 (15) NE8L: FIG. 3A—SEQ ID NO: 55; FIG. 3B—SEQ ID NO: 60 (Myanmar, 16), Hyderabad: FIG. 3A—SEQ ID NO: 54; FIG. 3B—SEQ ID NO: 64 (India, 17), Madras: FIG. 3A—SEQ ID NO: 51; FIG. 3B—SEQ ID NO: 13 (India, GenBank Accession No. 99441), HEV037: FIG. 3A—SEQ ID NO: 53; FIG. 3B—SEQ ID NO: 61 (isolate from a case of fulminant hepatitis, GenBank Accession No. X98292), Sar55: FIG. 3A—SEQ ID NO: 12; FIG. 3B—SEQ ID NO: 13 (Pakistan, 18), KS2-87: FIG. 3A—SEQ ID NO: 49; FIG. 3B—SEQ ID NO: 59 (China, 19), Hetian: FIG. 3A—SEQ ID NO: 56; FIG. 3B—SEQ ID NO: 63 (China, GenBank Accession No. L08816), Uigh179: FIG. 3A—SEQ ID NO: 52; FIG. 3B—SEQ ID NO: 62 (China, 20).

FIGS. 6A–6J show the nucleotide (FIGS. 6A–6C) and deduced amino acid sequences (FIGS. 6D–6J) of the ORF1 of the swine HEV.

FIGS. 7A–7D show the complete genomic sequence of the swine HEV.

FIGS. 8A–8B. Amplification of the complete genome of swine HEV. (FIG. 8A) The genomic organization of HEV and its putative functional domains are shown beneath the nucleotide scale bar (in Kb). The relative positions of the PCR fragments are indicated by bars. (FIG. 8B) Oligonucleotide primers used to amplify each fragment are indicated. Both the first round PCR primers and the second round nested PCR primers (italics) are shown (SEQ ID NOS: 14–47 respectively). Degenerate bases are shown in parentheses. Mt, methyltransferase; Y, Y domain; P, cysteine-like protease; Pro, proline-rich "hinge" region; X, X domain; Hel, helicase; RDRP, RNA-directed RNA polymerase.

DETAILED DESCRIPTION OF THE INVENTION

Figure 1A:
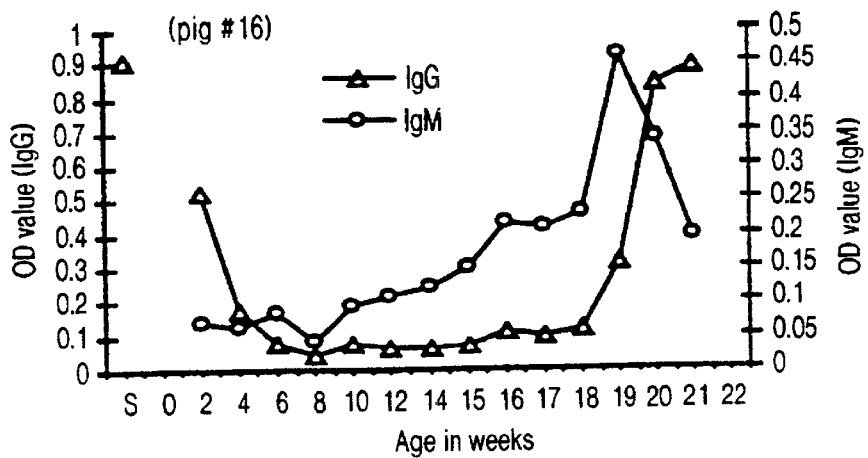
FIGS. 1A–1C. This figure shows seroconversion of 3 representative piglets to anti-HEV by plotting age (abscissa) in weeks versus the absorbance (or OD) of serum for IgG (left ordinate) and IgM (right ordinate)

The present invention relates to novel and useful hepatitis E virus strains from swine and naturally occurring mutants thereof.

As shown a long time ago with smallpox virus, it is highly advantageous to have available an attenuated virus, such as cowpox, to use for vaccination purposes. Such relatively innocuous virus particles, which can cross-react with antibodies against the more deadly organisms, can often be used to produce a highly effective vaccine to immunize at-risk animals, especially humans, against infection with otherwise extremely virulent microbes. In the same way, it would behighly advantageous to have a similar attenuated type of vaccine to use in immunization programs against hepatitis E virus. It is an object of this invention to provide such a vaccine.

In accordance with the present invention, a swine hepatitis E virus has been identified and shown to be similar in its characteristic properties to human hepatitis E virus. The virus of the present invention has been shown to be similar to the human virus by demonstrating seroconversion of pigs to anti-HEV, sequence similarity between the virus of the invention and human strains of HEV, viremia just prior to seroconversion, and histologic evidence of hepatitis infection in naturally-infected pigs. The swine-HEV cross-reacted with human HEV capsid antigen, and the infected piglets showed microscopic evidence of hepatitis during the acute stage of the infection.

The high prevalence of anti-HEV in commercial swine herds suggest that swine HEV is widespread in the general swine population. However, our results showed that naturally infected young pigs did not display clinical symptoms despite microscopic evidence of hepatitis. This suggests that swine HEV causes only subclinical infection in young pigs, a situation reminiscent of hepatitis A virus (HAV) in humans (21). Children infected with HAV are often asymptomatic, but most adults infected show typical clinical symptoms (21). It is difficult to evaluate the outcome of natural swine HEV infection in adult pigs since virtually all swine at least 3 months of age had IgG anti-HEV. Experimental infection of adult SPF swine with swine HEV will likely be necessary to answer this question.

The amino acid differences between swine and human HEV in the putative capsid gene are less than 10%. However, the high degree of amino acid sequence conservation in the capsid gene among human strains of HEV could indicate a functional significance for the differences between swine and human HEV. For example, in some cases only a few changes, or even a single change, in amino acid units of a structural protein have dramatically altered viral tropism and pathogenicity (22, 23). Of course, it is not clear whether swine HEV evolved into human HEV, or vice versa, or whether they diverged from a common ancestor. Regardless of lineage, the possibility that swine HEV could infect humans raises a potential public health concern for zoonosis or xenozoonosis, especially since xenotransplantation of pig organs has been suggested as a solution to the solid organ donor shortage for transplantations. Thus, xenozoonoses, the inadvertent transmission of pathogens from animal organs to human recipients, is of major concern (24). Viruses pathogenic for pigs might pose a risk to humans. However, nonpathogenic pig viruses may also become pathogenic for humans after xenotransplantation, as a result of species-jumping, recombination or adaptation in immunocompromised xenotransplantation recipients (24). Furthermore, pigs recovered from swine HEV infection might have a damaged liver (or other organ) which would limit usefulness for xenotransplantation.

Because of these and other potential public health concerns, it would be highly advantageous to have a swine HEV that is sufficiently closely related to human HEV as to allow evaluation as a potential source of infection in humans. In accordance with the present invention, such a swine HEV has been isolated and shown to have substantial nucleotide sequence homology with the human hepatitis E virus. Also in accordance with the present invention, the entire open reading frames (ORF) 2 and 3 were amplified by RT-PCR from sera of naturally-infected pigs. The putative capsid gene (ORF2) of swine HEV shares about 79% to about 80% sequence identity at the nucleotide level and about 90% to about 92% identity at the amino acid level related to human HEV strains. The small ORF3 of swine HEV had about 83% to about 85% nucleotide sequence identity and about 77% to about 82% amino acid identity with human HEV strains. The putative nonstructural proteins of ORF1 of swine HEV share about 98% amino acid identity with the U.S. human isolates of HEV but only about 80–81% identity with HEV strains from Asia and Mexico. Phylogenetic analyses showed that swine HEV is closely related to, but distinct from, human HEV strains.

The availability of an HEV capable of infecting both humans and animals with a subclinical hepatitis infection would be highly advantageous if used prophylactically, in the form of a vaccine, or therapeutically, as an inoculum to treat early-stage infections. When the present invention is used prophylactically, the agents are provided in advance of any symptom. This prophylactic use of the swine HEV serves to prevent or ameliorate any subsequent infection. When used therapeutically, the swine HEV of the present invention is provided at (or shortly after) the onset of any symptoms of infection. The swine HEV of the present invention can therefore be provided either before any anticipated exposure to hepatitis E virus (either swine or human), so as to ameliorate the anticipated severity, duration or extent of any subsequent infection or disease conditions, or after the onset of infection and disease.

When the swine HEV of the present invention is used as a vaccine, said vaccine comprises a pharmaceutical composition containing a sufficient number of viral particles, or recombinant proteins, to elicit a prophylactically effective immune response in the organism to be vaccinated, said amount also depending on the route of administration. The vaccine according to the present invention can thus be administered by oral, subcutaneous, intravenous, intramuscular or intraperitoneal routes. One skilled in the art will certainly appreciate that the amounts to be administered for any particular treatment protocol can be readily determined without undue experimentation. Suitable amounts might be expected to fall within the range of about 2 $\mu$g of viral protein per kg of body weight to about 100 $\mu$g viral protein per kg of body weight. Of course, the actual amounts will vary depending on the route of administration as well as the sex, age, and clinical status of the subject which, in the case of human patients, is to be determined within the sound judgment of the clinician.

The vaccine of the present invention may be employed in such forms as capsules, liquid solutions, suspensions or elixirs for oral administration, or sterile liquid forms such as solutions or suspensions. Any inert carrier is preferably used, such as saline, phosphate-buffered saline, or any such carrier in which the swine HEV of the present invention can be suitably suspended. The vaccines may be in the form of single dose preparations or in multi-dose flasks which can be utilized for mass-vaccination programs of both animals and humans. For purposes of using the swine HEV of the present invention as a vaccine, reference is made to Remington's *Pharmaceutical Sciences*, Mack Publishing Co., Easton, Pa., Osol (Ed.) (1980); and *New Trends and Developments in Vaccines*, Voller et al (Eds.), University Park Press, Baltimore, Md. (1978), both of which provide much useful information for preparing and using vaccines. Of course, the swine HEV, when used as a vaccine, can include, as part of the composition or emulsion, a suitable adjuvant, such as alum (or aluminum hydroxide) when humans are to be vaccinated, to further stimulate production of antibodies by immune cells.

When the swine HEV of the present invention is used as a vaccine, the virus itself may be live, killed, or live but attenuated. However, with a swine HEV producing only subclinical symptoms in swine and in other animals, especially humans, further attenuation may not be necessary.

When the swine HEV of the present invention is used as a vaccine or inoculum, it will normally exist as a physically discrete unit suitable as a unitary dosage for animals, especially mammals, and most especially humans, wherein each unit will contain a predetermined quantity of active viral material calculated to produce the desired immunogenic effect in association with the required diluent. The dose of said vaccine or inoculum according to the present invention is administered at least once. In order to increase the antibody level, a second or booster dose may be administered at some time after the initial dose. The need for, and timing of, such booster dose will, of course, be determined within the sound judgment of the administrator of such vaccine or inoculum and according to sound principles well known in the art. For example, such booster dose could reasonably be expected to be advantageous at some time between about 2 weeks to about 6 weeks following the initial vaccination. Subsequent doses may be administered as indicated.

The swine HEV of the present invention can also be administered for purposes of therapy, where an animal, especially a mammal, and most especially a human, is already infected, as shown by well known diagnostic measures. When the swine HEV of the present invention is used for such therapeutic purposes, much of the same criteria will apply as when it is used as a vaccine, except that inoculation will occur post-infection. Thus, when the swine HEV of the present invention is used as a therapeutic agent in the treatment of infection said therapeutic agent comprises a pharmaceutical composition containing a sufficient number of viral particles to elicit a therapeutically effective response in the organism to be treated, said amount also depending on the route of administration. The therapeutic agent according to the present invention can thus be administered by oral, subcutaneous, intravenous, intramuscular or intraperitoneal routes, with oral or intravenous routes being preferred. One skilled in the art will certainly appreciate that the amounts to be administered for any particular treatment protocol can be readily determined without undue experimentation. Suitable amounts might be expected to fall within the range of about 2 $\mu$g of viral protein per kg of body weight to about 100 $\mu$g viral protein per kg of body weight. Of course, the actual amounts will vary depending on the route of administration as well as the sex, age, and clinical status of the subject which, in the case of human patients, is to be determined within the sound judgment of the clinician.

The therapeutic agent of the present invention can be employed in such forms as capsules, liquid solutions, suspensions or elixirs for oral administration, or sterile liquid forms such as solutions or suspensions. Any inert carrier is preferably used, such as saline, phosphate-buffered saline, or any such carrier in which the swine HEV of the present invention can be suitably suspended. The therapeutic agents may be in the form of single dose preparations or in the multi-dose flasks which can be utilized for mass-treatment programs of both animals and humans. Of course, when the swine HEV of the present invention is used as a therapeutic agent it may be administered as a single dose or as a series of doses, depending on the situation as determined by the person conducting the treatment.

The swine HEV of the present invention can also be utilized in the production of antibodies against HEV. The term "antibody" is herein used to refer to immunoglobulin molecules and immunologically active portions of immunoglobulin molecules. Examples of antibody molecules are intact immunoglobulin molecules, substantially intact immunoglobulin molecules and portions of an immunoglobulin molecule, including those portions known in the art as Fab, F(ab')$_2$ and F(v) as well as chimeric antibody molecules.

The swine HEV of the present invention can be used in the generation of antibodies that immunoreact (i.e., specific binding between an antigenic determinant-containing molecule and a molecule containing an antibody combining site such as a whole antibody molecule or an active portion thereof) with antigenic determinants on the surface of hepatitis E virus particles that commonly infect non-swine species, especially humans. Thus, the observed cross-reaction between the swine HEV of the present invention and antibodies against human HEV make the swine HEV useful in generation of antibodies against human HEV, thus facilitating the use of the swine HEV as a vaccine for humans.

The present invention also relates to antibodies produced following immunization with the swine HEV according to the present invention. These antibodies are typically produced by immunizing a mammal with an immunogen or vaccine comprising the swine HEV of the present invention to induce, in said mammal, antibody molecules having immunospecificity for the swine HEV. When used in generating such antibodies, the swine HEV of the present invention may be linked to some type of carrier molecule. The resulting antibody molecules are then collected from said mammal.

The antibody molecules of the present invention may be polyclonal or monoclonal. Monoclonal antibodies are readily produced by methods well known in the art. Portions of immunoglobulin molecules, such as Fabs, as well as chimeric antibodies may also be produced by methods well known to those of ordinary skill in the art of generating such antibodies and requires no specific elucidation herein.

The antibody according to the present invention may be contained in blood plasma, serum, hybridoma supernatants, and the like. Alternatively, the antibody of the present invention is isolated to the extent desired by well known techniques such as, for example, using DEAE Sephadex. The antibodies produced according to the present invention may be further purified so as to obtain specific classes or subclasses of antibody such as IgM, IgG, IgA, and the like.

Antibodies of the IgG class are preferred for purposes of passive protection.

The antibodies of the present invention are useful in the prevention and treatment of diseases caused by hepatitis E virus in animals, especially mammals, and most especially humans.

In providing the antibodies of the present invention to a recipient mammal, preferably a human, the dosage of administered antibodies will vary depending on such factors as the mammal's age, weight, height, sex, general medical condition, previous medical history, and the like.

In general, it will be advantageous to provide the recipient mammal with a dosage of antibodies in the range of from about 1 mg/kg body weight to about 10 mg/kg body weight of the mammal, although a lower or higher dose may be administered if found desirable. Such antibodies will normally be administered by intravenous route as an inoculum. The antibodies of the present invention are intended to be provided to the recipient subject in an amount sufficient to prevent, lessen or attenuate the severity, extent or duration or any existing infection.

The antibodies prepared by use of the swine HEV of the present invention are also highly useful for diagnostic purposes. The antibodies can be used as in vitro diagnostic agents to test for the presence of virus in biological samples taken from animals, especially swine and humans. Such assays include, but are not limited to, radioimmunoassays, EIA, fluorescence, Western blot analysis and the like. In one such embodiment, the biological sample is contacted with antibodies of the present invention and a labeled second antibody is used to detect the presence of HEV to which the antibodies are bound.

Such assays may be, for example, of direct protocol (where the labeled first antibody is immunoreactive with the antigen, such as, for example, a protein on the surface of the virus), an indirect protocol (where a labeled second antibody is reactive with the first antibody), a competitive protocol (such as would involve the addition of a labeled antigen), or a sandwich protocol (where both labeled and unlabeled antibody are used), as well as other protocols well known and described in the art.

In one embodiment, an immunoassay method would utilize an antibody specific for a substance comprising HEV surface antigen (HCSA) determinants and would further comprise the steps of contacting a test sample containing said test substance containing the HESA determinants with the HEV-specific antibody and then detecting the presence of HEV material in the test substance using one of the types of assay protocols as described above.

Recombinant proteins arid antibodies produced according to the present invention may also be supplied in the form of a kit, either present in vials as purified material, or present in compositions and suspended in suitable diluents as previously described. In a preferred embodiment, such a diagnostic test kit for detection of HEV antigens in a test sample comprises in combination a series of containers, each container a reagent needed for such assay. Thus, one such container would contain a specific amount of HEV-specific antibody as already described, a second container would contain a diluent for suspension of the sample to be tested, a third container would contain a positive control and an additional container would contain a negative control. An additional container could contain a blank.

Because the Open Reading Frame (ORF2) that codes for a putative capsid protein has been cloned in vitro it can be used to prepare recombinant proteins that themselves are available for use as vaccines and therapeutic agents. In accordance with the present invention, said capsid protein antigen has been prepared. A similar approach is advantageous with respect to ORFs 1 and 3 and their protein products. Since such recombinant proteins also represent antigenic determinants on the virus, and presumably are responsible for the immunogenicity of the particles of the swine hepatitis E virus of the present invention, such recombinant proteins can also be used to generate antibodies useful as therapeutic agents in the treatment of hepatitis E in animals, especially humans. Such antibodies can also be used in protocols for in vitro assays for detection of hepatitis E virus in an animal, especially a human, suspected of being infected therewith.

Because the swine HEV can be used to infect cells in culture, the present invention also relates to a method for determining the susceptibility of cells in vitro to support HEV infection. This would permit determination of the susceptibility of cells from various organs, for example, of the pig, to determine their potential use for possible transplantation into other animals, especially humans. Cells from organs susceptible to such infection might be questionable candidates for eventual transplantation. In one such embodiment, the method would comprise the growing of animal cells, especially swine cells, in vitro and exposing said cells to the swine HEV of the present invention, then determining if the cells show indicia of HEV replication. Such indicia would include the detection of viral antigens in the cell, for example, by immunofluorescent procedures well known in the art. Such viral proteins would also be detected by Western blotting using antibodies specific therefor. Such indicia would also include the successful extraction of newly transcribed viral DNA within the cells. The presence of live, infectious virus particles following such test could also be shown by injection of cell culture medium into healthy animals, with subsequent exhibition of the symptoms of HCV infection. Such testing could also be carried out with cells from tissues of other species to determine their susceptibility to infection by the swine HEV of the present invention, relying on the same criteria to show viral replication.

It is known that swine show antibodies to HEV and have been suggested as a possible animal reservoir for this virus. In addition, IgG anti-HEV is also found in a significant proportion of otherwise healthy humans from different areas. Since the causative agent is still unclear, it would be highly advantageous to determine if the antibodies found in an animal, especially a human, are the result of human HEV or perhaps a swine HEV or other animal. It is thus an object of the present invention to provide a method for differential diagnosis of HEV antibodies in animals, especially in humans, to determine the likely causative agent thereof and thus the presence of possible subclinical infections that can serve as a source of the disease. Armed with the virus of the present invention many protocols for such diagnoses will no doubt suggest themselves to those of skill in the art.

In one embodiment of the present invention a tissue sample from an animal, perhaps one suspected of harboring an infection of HEV, will be obtained and then treated with antibodies specific for either human HEV antigenic determinants or the swine HEV antigenic determinants, such as an antibody of the present invention. The formation and detection of a complex between the substance in the sample that possesses such determinants and the antibodies specific for the virus will indicate the presence of viral determinants. By titering the different antibodies to determine their relative occurrence, it is then possible to determine if the source of the antigen is of human or swine, or other animal, origin. Such differential diagnosis can be carried out on any animal, especially primates and other mammals, and most especially humans. The sample to be tested can, of course, be any tissue excised from said animal, especially blood and other fluids.

Today there is a great thrust toward the use of animal organs for transplantation into other animals, especially into humans, with pigs as a suggested arid useful donor organism. Before such programs can continue, or even begin, it would be highly advantageous to determine if any infectious agents exist in the donor animal and, if so, whether such organisms can infect the donee, especially humans. Because IgG anti-HEV is found in swine and the swine HEV of the present invention has been recovered from pigs and has great similarity to the human HEV, it is a potentially infectious agent in humans. It is thus an object of the present invention to utilize the swine HEV as a test organism for the assessment of risk factors in such xenotransplantation between the pig, as donor, and other animals, especially humans.

Various protocols to test transplantable organs and tissues for such potentially infectious agents will, of course, suggest themselves to those of skill in the art. In one such embodiment of the present invention, a biological sample of a tissue, for example, from a pig to be used as a donor organism, will be obtained prior to any transplantation and such sample is then tested for the presence of swine HEV. Such tissues for transplantation may include liver, heart and kidneys, but are by no means limited to these. The testing of such tissue for the presence of swine HEV can be accomplished by a number of procedures already disclosed herein and using methods well known in the art. For example, a candidate tissue can be examined using antibodies tagged with a label, such as an immunofluorescent label, to determine the presence or absence of swine HEV antigenic determinants therein, with complex formation (a positive reaction) indicating the presence of viral contamination. In addition, DNA extracted from cells of the candidate tissue can be amplified by RT-PCR (reverse transcriptase-polymerase chain reaction) and tested for hybridization therewith using nucleic acid probes, especially chemically or radioactively labeled probes, to determine the presence or absence of sequences unique to the swine HEV genome where hybridization indicates the presence of viral contamination.

For all prophylactic, therapeutic and diagnostic uses, the swine HEV of the present invention, alone or linked to some carrier, as well as antibodies and other reagents, plus appropriate devices and accessories, may be provided in the form of a kit so as to facilitate ready availability and ease of use.

MATERIALS AND METHODS

Serum samples. Serum samples were obtained from swine of various ages in 15 commercial herds and one specific-pathogen-free (SPF) herd in the midwestern United

TABLE 1

IgG anti-HEV prevalence in swine from commercial herds in the United States.

| Herd | Age | No. of swine tested | No. of swine with anti-HEV (%) |
|---|---|---|---|
| A | 6 wk | 8 | 0(0) |
|  | 12 wk | 8 | 0(0) |
|  | 20 wk | 8 | 8(100) |

TABLE 1-continued

IgG anti-HEV prevalence in swine from commercial herds in the United States.

| Herd | Age | No. of swine tested | No. of swine with anti-HEV (%) |
|---|---|---|---|
|   | 26 wk | 8 | 5(63) |
|   | Adult | 25 | 14(56) |
| B | 3–4 wk | 8 | 0(0) |
|   | 5–6 wk | 8 | 0(0) |
|   | 7–8 wk | 8 | 0(0) |
|   | 13 wk | 12 | 10(83) |
|   | 6 mo | 8 | 8(100) |
|   | Adult | 17 | 16(94) |
| C | 2 mo | 8 | 1(13) |
|   | 3 mo | 8 | 8(100) |
|   | 4 mo | 8 | 4(50) |
|   | 5 mo | 8 | 8(100) |
|   | Adult | 8 | 8(100) |
| D | 2 mo | 10 | 2(20) |
| E | 6 mo | 10 | 10(100) |
| F | 6 mo | 10 | 10(100) |
| G | 6 mo | 10 | 10(100) |
| H | 8 mo | 10 | 10(100) |
| I | >1 yr | 10 | 10(100) |
| J | 1–2 yr | 10 | 10(100) |
| K | 1–3 yr | 10 | 10(100) |
| L | 2 yr | 10 | 10(100) |
| M | 2–3 yr | 10 | 10(100) |
| N | Adult | 19 | 15(79) |
| O | Adult | 6 | 5(83) |
| P* | Adult | 10 | 0(0) |

*Specific-pathogen-free (SPF) swine herd.

Preparation of HEV putative capsid antigen. Insect cells were infected with recombinant baculovirus containing the putative capsid gene (ORF2) sequence of a Pakistani strain of HEV, SAR55 (8). A 55 kD recombinant protein expressed from a recombinant baculovirus containing ORF2 was purified from insect cells (8) and used for the standard ELISA. The ORF2 recombinant protein was further purified by high pressure liquid chromatography (HPLC).

Generation of hyperimmune swine antibody to HEV. Two SPF swine, 3 weeks old, were immunized intramuscularly with 50 µg of HPLC-purified ORF2 recombinant protein mixed with Freund's incomplete adjuvant. Booster immunizations were given at 2 and 4 weeks after the first immunization. Sera obtained before immunization and weekly for 9 weeks after immunization were used to develop an ELISA (see below).

ELISA for anti-HEV in swine. The standard ELISA for anti-HEV in swine was performed essentially as described for anti-HEV in chimpanzees (8, 12), except that the secondary antibody was replaced with peroxidase-labeled goat anti-swine IgG (KPL, Gaithersburg, Md.). All of the swine serum samples were tested in duplicate. Preimmune and hyperimmune anti-HEV positive swine sera were included as negative and positive controls, respectively.

Blocking ELISA was used to confirm the results of the standard ELISA on selected anti-HEV positive and negative serum samples. The blocking ELISA for anti-HEV in swine was performed essentially as described (13) except that the competing sera were from swine. The ORF2 protein of strain SAR55 was used for affinity purification of anti-HEV from convalescent serum of a chimpanzee exposed twice to HEV (8). The affinity-purified chimpanzee anti-HEV was conjugated with horseradish peroxidase by a custom service (ViroStat, Portland, Me.), and used for the blocking ELISA (13). A serum sample was considered positive in the blocking ELISA if the OD value was reduced by ≧50% compared to the unblocked sample.

Prospective study. Twenty-one sows from a commercial herd were tested for IgG anti-HEV. Subsequently, twenty piglets (10 male and 10 female) were chosen from those born to seronegative sows (6 piglets) and to seropositive sows with a lower titer (6 piglets) or higher titer (8 piglets) of IgG anti-HEV. These 20 study piglets were tagged and mixed with other piglets from approximately 50 sows in the herd, and were commingled in two rooms in a nursery building. Piglets within a room were separated into pens by fences which allowed for nose-to-nose contacts. By the age of about 10 weeks, all piglets in the nursery building were moved to a finishing building that had been previously emptied and disinfected.

Blood samples and nasal and rectal swabs from the 20 study piglets were collected in alternate weeks from 2 weeks onward, and weekly after 14 weeks of age. The serum samples were tested for anti-HEV, and four piglets with an increasing ELISA OD value were sacrificed. Samples of 19 different tissues and organs were collected during necropsy, fixed in 10% neutral buffered formalin and processed for routine histologic examination.

Degenerate primers for reverse transcription-polymerase chain reaction (RT-PCR). The sequences of ten human HEV strains were aligned with a GeneWorks program (IntelliGenetics, Inc., Mountain View, Calif.). Based on this alignment, two sets of degenerate primers were designed and synthesized to amplify two different regions of the capsid gene. The primer positions indicated below are relative to the published sequence of a Burmese HEV strain (14). Set one primers: external 3156 (forward, position 5687–5708, 5'-AAT(C)TATGCC(A)AGTACCGGGTTG-3' (SEQ ID NO: 4)) and 3157 (reverse, position 6395–6417, 5'-CCCTTATCCTGCTGAGCATTCTC3' (SEQ ID NO: 5)), and ternal 3158 (forward, position 5972–5993, 5'-GTT(C)ATGC(T)TT(C)TGCATACATGGCT-3' (SEQ ID NO: 6)) and 3159 (reverse, position 6297–6319, 5'-AGCCGACGAAATC(T)AATTCTGTC-3' (SEQ ID NO: 7)). Set two primers: external 3160 (forward, position 6578–6600, 5'-GCCGAGTAT(C)GACCAGTCCACTTA-3' (SEQ ID NO: 8)) and 3161 (reverse, position 7105–7127, 5'-AT(C)AACTCCCGAGTTTTACCCACC-3' (SEQ ID NO: 9)), and internal 3162 (forward, position 6645–6667, 5'-TGGTT(G)AATGTT(A)GCGACC(T)GGCGCG-3' (SEQ ID NO: 10)) and 3163 (reverse, position 7063–7085, 5'-GCTCAGCGACAGTA(T)GACTGG(A)AAA-3') (SEQ ID NO: 10)).

RNA extraction and RT-PCR. Total RNA was extracted by TriZol reagent (GIBCO-BRL, Gaithersburg, Md.) from 100 µl of serum obtained 1 or 2 weeks before seroconversion from piglets in the Prospective study. Total RNA was then reverse transcribed with one of the two degenerate primers by using SuperScript II reverse transcriptase (GIBCO-BRL, Gaithersburg, Md.) at 42° C. for 1 hr, and the resulting cDNA was amplified by PCR using ampliTaq Gold polymerase (Perkin Elmer, Norwalk, Conn.). The PCR reaction was carried out for 39 cycles of denaturation at 94° C. for 1 min, annealing at 42° C. for 1 min, and extension at 72° C. for 2 min, followed by a nested PCR using 10 µl of the first round PCR product with a nested set of degenerate primers.

Amplification of the entire ORFs 2 and 3 of swine HEV. After the first PCR fragment was amplified and sequenced, we designed two sets of primers, with a swine HEV-specific primer at one end and a degenerate primer at the other end (primer sequences not shown). RT-PCR with these primers was performed essentially the same as described above. The entire ORFs 2 and 3 of swine HEV were amplified in this way by walking along the genome in both directions.

Sequence analysis. The PCR fragments were cut from 1% agarose gels and purified with a Geneclean Kit (Bio101, La Jolla, Calif.). Both strands were sequenced with an automated DNA Sequencer. The sequences were analyzed by the GeneWorks program. Phylogenetic analyses were conducted with the aid of the PAUP software package version 3.1.1 (David L. Swofford, Illinois Natural History Survey, Champaign, Ill.).

EXAMPLES

Standardization of an ELISA for swine anti-HEV. To establish a reliable serological test for anti-HEV in swine, we first generated hyperimmune antisera by immunizing two SPF pigs with recombinant HEV ORF2 antigen. IgG anti-HEV was first detected at 2 and 3 weeks postimmunization, and reached peak ELISA titers of $10^{-4}$ at weeks 3 and 4 postimmunization, respectively. The anti-HEV titer remained at $10^{-4}$ until the end of the 9 week experiment. An ELISA for swine anti-HEV was subsequently standardized by using the preimmune and hyperimmune swine sera along with 34 normal sera from swine raised in laboratory environments and from swine in an SPF herd. The ELISA cutoff value was set at 99% confidence bounds, based on the frequency distribution of the absorbance values of normal sera. The cutoff value was approximately 2.5 standard deviations above the mean absorbance value of the normal sera.

Serologic evidence in swine for infection with an agent related to HEV. The prevalence of anti-HEV in commercial swine herds in the midwestern United States was assessed by the standardized ELISA. Surprisingly, IgG anti-HEV was found in a majority of swine ≧3 months of age in herds in the midwestern United States where human hepatitis E is not endemic; however, most swine ≦2 months of age were seronegative (Table 1). None of the 10 adult swine from an SPF herd was seropositive (Table 1). To further validate the serology results, we performed a blocking ELISA on selected anti-HEV positive and negative swine sera. Similar results were obtained in the blocking ELISA and the standard ELISA. The HEV antigen used in ELISA was expressed in insect cells; therefore we also included insect cells infected with baculovirus lacking the HEV sequence as a negative antigen control and HPLC-purified HEV recombinant antigen as a positive antigen control. There was little or no reaction between the swine serum samples and the insect cells infected with the baculovirus lacking the HEV sequence. Thus, the swine anti-HEV reacted specifically with the human HEV capsid antigen in the standard ELISA and completed with anti-HEV in convalescent chimpanzee serum in the blocking ELISA. These data strongly suggested that a ubiquitous swine agent, antigenically related to human HEV, was circulating in the general swine population.

Natural infection of swine in a commercial herd. In an attempt to identify this putative HEV-related agent in pigs, a prospective study was conducted in a commercial swine herd in the Midwestern United States. Consistent with our seroepidemiological results, 18 of 21 pregnant sows tested from this herd were positive for anti-HEV. Piglets born to seronegative sows were seronegative at 2 weeks of age, and piglets born to seropositive sows with a lower titer of IgG anti-HEV also scored as seronegative but had a comparatively high ELISA OD value for IgG anti-HEV as shown in Table 2.

TABLE 2

Seroconversion of piglets to anti-HEV in a commercial herd: a prospective study

| Piglet No. | Breeder sow ELISA OD* | Piglet ELISA OD* | | Age seroconverted (wks) |
|---|---|---|---|---|
| | | 2 wks | 8 or 9 wks | |
| 15 | 0.908 | 0.550 | 0.036 | Nt |
| 16 | 0.908 | 0.522 | 0.039 | 19 |
| 17 | 0.908 | 0.501 | 0.066 | Neg‡ |
| 18 | 1.011 | 0.822 | 0.103 | N† |
| 19 | 1.011 | 1.264 | 0.148 | 15 |
| 20 | 1.011 | 0.979 | 0.146 | Death§ |
| 1 | 0.692 | 0.128 | 0.024 | 18 |
| 7 | 0.692 | 0.211 | 0.071 | 21 |
| 3 | 0.692 | 0.157 | 0.052 | 20 |
| 4 | 0.692 | 0.114 | 0.026 | 18 |
| 5 | 0.431 | 0.107 | 0.065 | 18 |
| 6 | 0.431 | 0.216 | 0.059 | 21 |
| 7 | 0.424 | 0.113 | 0.073 | 16N† |
| 8 | 0.424 | 0.195 | 0.093 | 15 |
| 9 | 0.209 | 0.047 | 0.050 | 18 |
| 10 | 0.209 | 0.079 | 0.090 | 19 |
| 11 | 0.209 | 0.047 | 0.039 | 19 |
| 12 | 0.245 | 0.057 | 0.061 | 14 |
| 13 | 0.245 | 0.056 | 0.038 | 16 |
| 14 | 0.245 | 0.057 | 0.012 | 20N† |

Figure 1B:
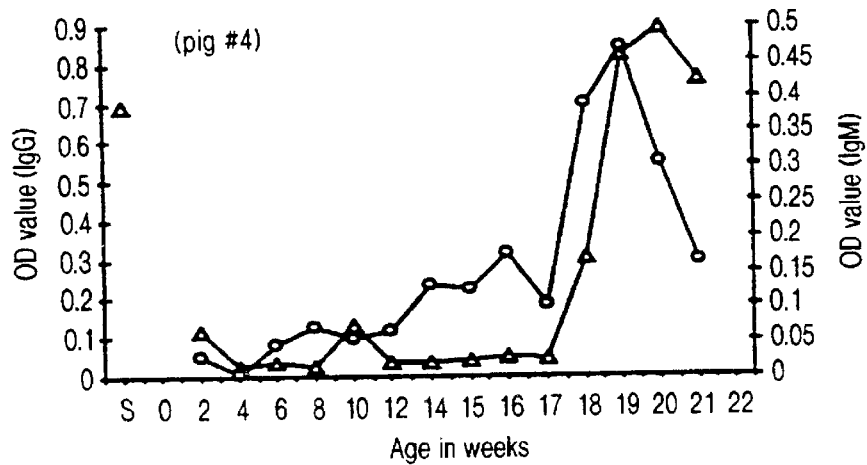
Figure 1C:
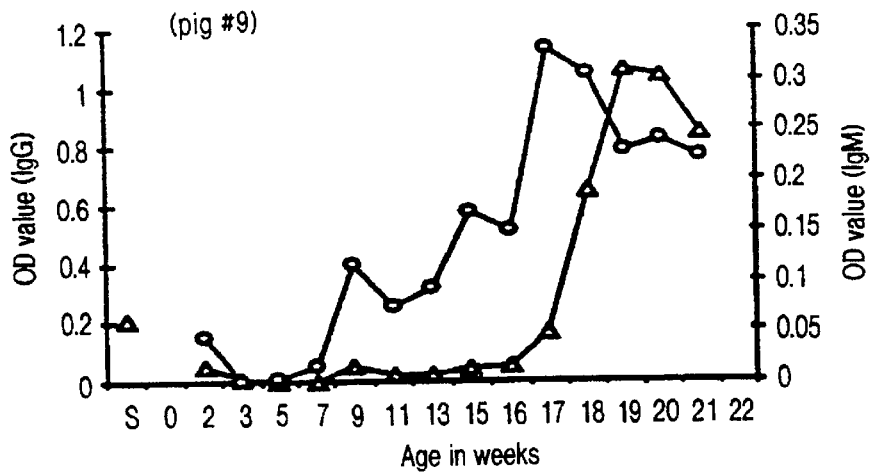

*Elisa cut-off value: 0.3;
N†: necropsied
‡Neg: remains seronegative at 21 weeks of age
§Death due to unknown cause In contrast, piglets born to seropositive sows with a higher titer of IgG anti-HEV were positive at 2 weeks of age for IgG anti-HEV (Table 2), but not for IgM anti-HEV. The level of IgG anti-HEV in seropositive piglets decreased dramatically within a few weeks after birth and had disappeared by the age of 8 or 9 weeks (Table 2, FIG. 1). Clearly, the anti-HEV detected in these newborns represented maternal antibody as evidenced by the correlation between the levels of anti-HEV in 2 weeks old piglets and in their dams (Table 2), and from the fact that the anti-HEV belonged to the IgG class. However, after the maternal antibody had waned, most of the piglets had developed their own antibodies to HEV. One piglet seroconverted to anti-HEV at the age of 14 weeks, followed within a few weeks by seroconversion of piglets in other pens housed in the same finishing building. The pattern of anti-HEV appearance, starting with piglets grouped near the first seropositive piglet, then followed by more distal ones, was consistent with seroconversion induced by an infectious agent (data not shown). By 21 weeks of age, 17 of the 20 piglets had seroconverted. Two other piglets were necropsied prior to seroconversion and one piglet died of an unknown cause. The only remaining seronegative piglet had a rising ELISA OD value but it was still below the cut-off value at the end of the 21 week study. The level of IgG anti-HEV increased steadily for several weeks after seroconversion (FIG. 1). IgM anti-HEV, indicating a newly contracted infection with this putative HEV-related agent, was also detected in all piglets which seroconverted to IgG anti-HEV. The level of IgM anti-HEV peaked about one week earlier than that of IgG anti-HEV and decreased rapidly over about 1 to 2 weeks (FIG. 1).

Clinical illness was not observed in the piglets. Four piglets believed to be at an early stage of infection were necropsied during the study. Except for a gross lung lesion consistent with a bacterial pneumonia in one piglet, other gross lesions were not apparent in 19 different tissues and organs examined during necropsy. Microscopically, all 4 piglets necropsied had evidence of hepatitis characterized by mild to moderate multifocal and periportal lymphoplasmacytic hepatitis with mild focal hepatocellular necrosis. In addition, all piglets had lymphoplasmacytic enteritis, and three piglets also had mild multifocal lymphoplasmacytic interstitial nephritis. Syncytial cells were also noticed in the tonsils and Peyer's patches of one piglet (data not shown).

Figure 2:
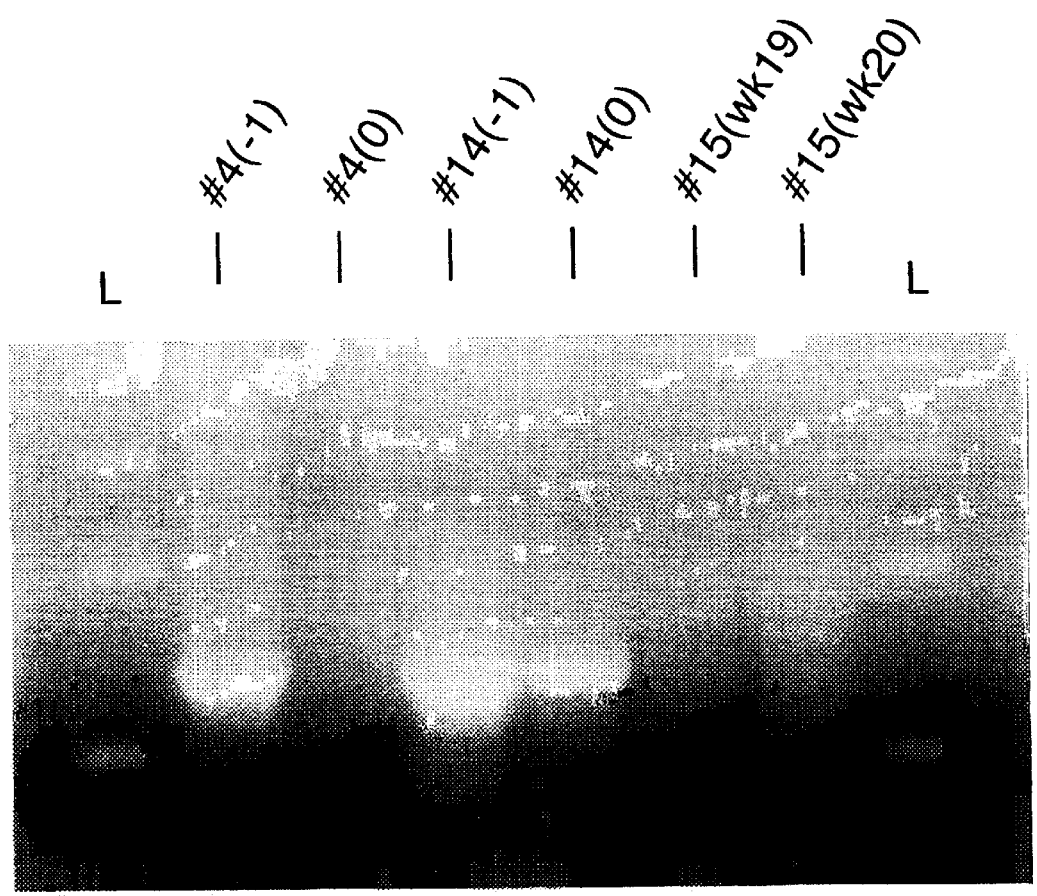
FIG. 2. Amplification of swine HEV-specific fragment by RT-PCR. Serum samples from 2 piglets (#4 and #14) obtained 1 week before (−1) and the week of (0) seroconversion were used for RT-PCR of a 344 bp fragment. Serum samples obtained at the same time (weeks 19 and 20) after birth from a seronegative piglet (#15) were also included. "L" represents the molecular weight markers.

Genetic characterization of the swine HEV. Since the swine anti-HEV reacted so strongly with the capsid protein of human HEV, it was probable that swine HEV shared nucleotide sequence similarity with human HEV. Therefore, two sets of degenerate primers derived from the HEV putative capsid gene were used to attempt the amplification of the swine HEV genome by RT-PCR of serum samples obtained 1 and 2 weeks before seroconversion. A fragment representing part of the swine HEV genome (FIG. 2) was first amplified by a nested-PCR with primer set 3158 and 3159. Sequence information confirmed that this initial PCR fragment was specific for swine HEV and represented part of the ORF2.

Sequence analyses of swine HEV ORFs 2 and 3. Analyses of the complete ORF 2 and 3 sequences revealed that swine HEV is closely related to, although distinct from, human HEV strains. In the putative capsid gene (ORF2), swine HEV shares with human HEV strains about 79 to 80% sequence identify at the nucleotide level, and about 90 to 92% identity at the amino acid level (Table 3, FIG. 3).

nucleotide level (Table 3). Most of the amino acid variations in ORF3 were clustered in a hypervariable region consisting of 17 amino acid residues near the carboxyl terminus (FIG. 3). In addition, the ORF3 of swine HEV had a single amino acid deletion near the amino terminus (FIG. 3).

Figure 4:
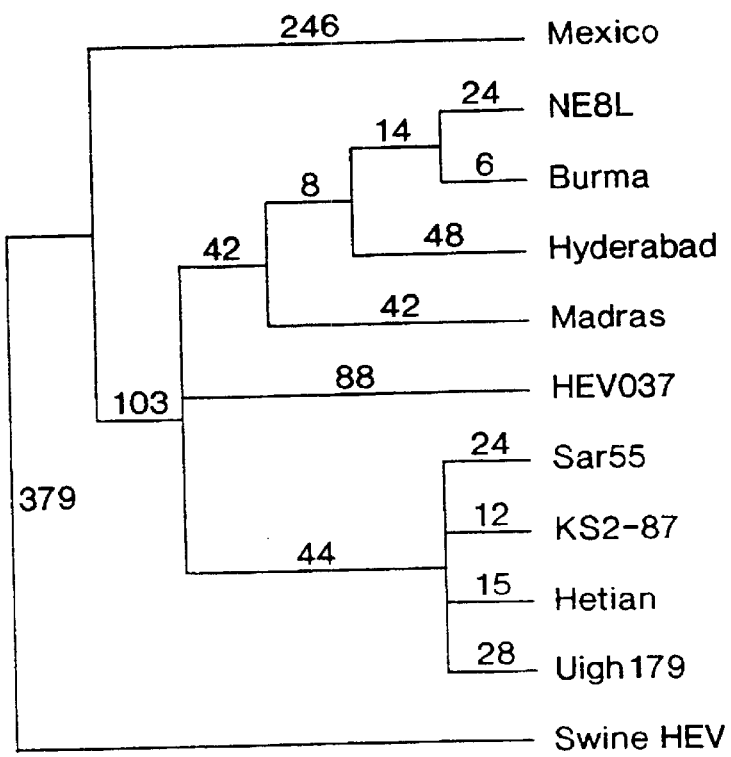
FIG. 4. Phylogenetic tree based on the complete nucleotide sequences of ORFs2 and 3. The tree was constructed by maximum parsimony methods with the aid of PAUP software package version 3.1.1. The tree with the shortest length (most parsimonious) was found by implementing the bootstrap (1000 replicas) using the branch-and-bound search option. The branch lengths (number given above each branch) are indicated.

The evolutionary relationships between swine and human HEV were determined on the basis of the complete nucleotide sequences of ORF2 and ORF3. The resulting phylogenetic tree revealed that human HEV strains were represented by at least two genotypes. The first genotype was represented by the Mexican strain, and the second genotype by the other human HEV strains (FIG. 4). Phylogenetically, swine HEV was unique, the most divergent of the HEV strains compared and the first member of a third genotype (FIG. 4).

Figure 5:
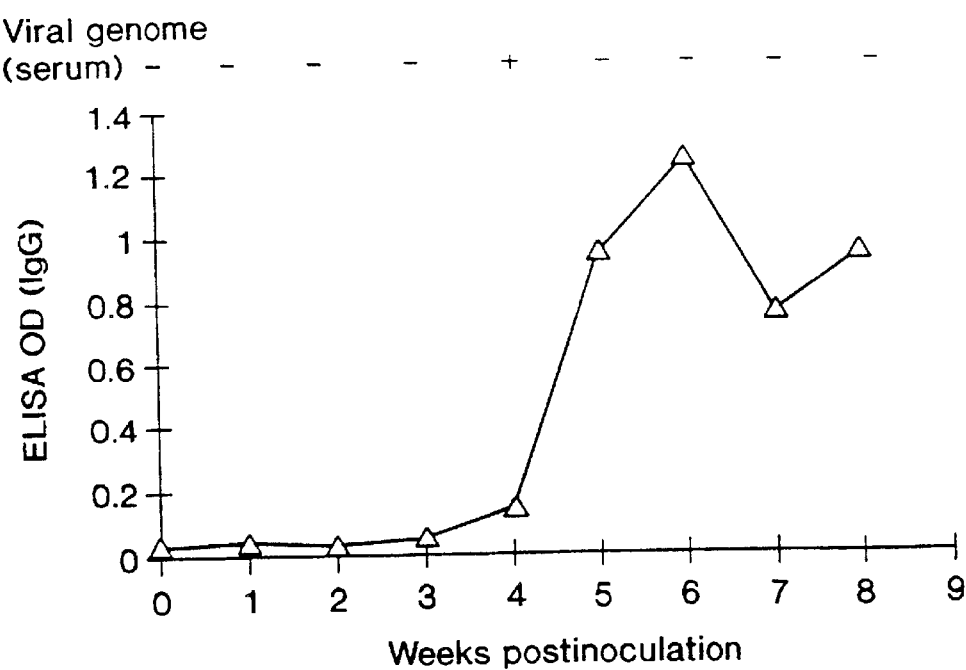
FIG. 5. Experimental infection of specific-pathogen-free swine with the swine HEV. The IgG anti-HEV response is plotted. Viremia was measured by RT-PCR as indicated along the top.

Experimental infection of SPF swine with swine HEV. SPF swine were inoculated intravenously with acute phase serum samples from the prospective study already described. The inoculated swine were monitored for anti-HEV response, viremia, and liver enzymes. The inoculated swine seroconverted to anti-HEV at 5 weeks post-inoculation, and viremia appeared one week before the seroconversion (FIG. 5). The incubation period for swine HEV is about 4 to 5 weeks since the control (uninoculated) pig housed in the same room seroconverted 8 weeks post-inoculation. A pig infected apparently by contact also developed viremia as measured by RT-PCR with swine HEV-specific primers. Viremia occurred 2 weeks before seroconversion (i.e., 6 weeks post-inoculation) and lasted for 3 weeks.

TABLE 3

Pairwise comparison of the nucleotide and deduced amino acid sequences of the open reading frames (ORFs) 2 and 3 of the swine hepatitis E virus (SHEV) with human HEV strains

| Strains | SHEV | Mexico | HEV-037 | Uigh-179 | Hetian | KS2-87 | Sar55 | Madras | Hyderabad | Burma | NE8L |
|---|---|---|---|---|---|---|---|---|---|---|---|
| ORF2 | | | | | | | | | | | |
| SHEV |  | 79(90) | 80(91) | 80(91) | 80(91) | 80(92) | 80(92) | 79(92) | 79(90) | 79(92) | 79(91) |
| Mexico | 83(79)* |  | 81(93) | 81(92) | 81(93) | 81(93) | 81(93) | 81(93) | 81(92) | 81(93) | 81(92) |
| HEV-037 | 84(82) | 90(89) |  | 94(98) | 94(98) | 94(98) | 94(99) | 94(98) | 92(97) | 94(98) | 94(98) |
| Uigh-179 | 84(80) | 90(85) | 97(97) |  | 98(98) | 98(99) | 97(99) | 93(98) | 93(97) | 94(99) | 93(98) |
| Hetian | 84(80) | 90(85) | 97(97) | 98(97) |  | 99(99) | 98(99) | 93(98) | 93(97) | 94(99) | 93(98) |
| KS2-87 | 84(80) | 90(85) | 97(97) | 98(98) | 98(97) |  | 98(99) | 93(99) | 93(98) | 94(99) | 94(98) |
| Sar55 | 85(82) | 91(87) | 98(98) | 99(98) | 99(98) | 99(98) |  | 93(99) | 93(98) | 94(99) | 93(99) |
| Madras | 85(82) | 90(87) | 98(98) | 98(98) | 98(98) | 98(98) | 99(100) |  | 96(98) | 97(99) | 96(98) |
| Hyderabad | 83(77) | 89(84) | 95(93) | 96(93) | 96(93) | 97(95) | 97(95) | 97(95) |  | 97(98) | 96(97) |
| Burma | 84(82) | 90(87) | 98(98) | 98(98) | 98(98) | 98(98) | 99(100) | 99(100) | 97(95) |  | 98(99) |
| NE8L | 84(81) | 90(87) | 98(97) | 98(97) | 97(97) | 97(97) | 98(98) | 98(98) | 95(93) | 99(98) |  |
| ORF3 | | | | | | | | | | | |

*The values in the table represent the percentage of nucleotide or amino acid (in bracket) sequences However, the relatively high amino acid identity between swine and human HEV is significantly lower than the amino acid identity (97 to 99%) among human HEV strains with the exception of the Mexican strain. The Mexican strain of HEV also displayed greater sequence divergence of about 92 to 93% amino acid identity with other human HEV strains (Table 3). However, the genetic distances between swine HEV and the Mexican strain of HEV are comparable to those between swine HEV and other human HEV strains, indicating that swine HEV is also distinct from the Mexican HEV (Table 3, FIG. 3). These data suggested that we had identified a previously unrecognized swine virus belonging to the same family as human HEV.

Figure 8A:
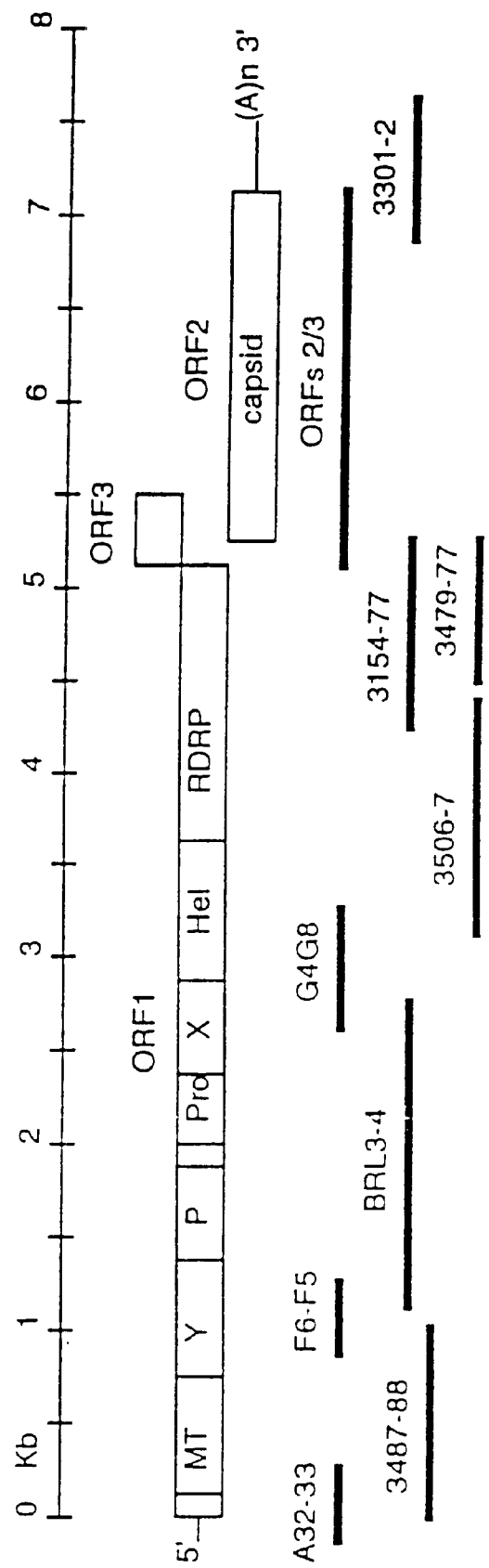

The small ORF3 of swine HEV had about 83 to 85% sequence identity at the nucleotide level with human HEV strains, but only 77 to 82% identity at the amino acid level (Table 3). The human HEV strains also displayed a lower percentage of identities at the amino acid level than at the Amplification of the complete genome of swine HEV. In order to extend the sequence of ORFs 2 and 3 of swine HEV to ORF1, a genome-walking strategy was utilized (FIG. 8). The complete genome of swine HEV was amplified by RT-PCR by using one swine HEV-specific primer and one HEV degenerate or consensus primer (FIG. 8). The PCR reaction conditions used to amplify different regions of the genome varied.

Sequence analysis of ORF1 and terminal NC regions of swine HEV. The nucleotide and deduced amino acid sequences of ORF1 are shown in FIGS. 6A–6J and the complete genomic sequence is shown in FIGS. 7A–7D.

The putative functional domains and the hypervariable region (HVR) in the ORF1 were compared with the corresponding regions of other HEV strains. The ORF1 of swine HEV and of the US-2 strain contain 5127 nucleotides (nts), which is 3 nts less than in the US-1 strain, but 45 and 51 nts more than in the Asian strains and the Mexico strain, respectively (data not shown). Swine HEV varied extensively, both at the nucleotide and amino acid levels, from non-U.S. strains of HEV although it was very similar to the two U.S. strains. The sequence identity in the putative methyltransferase and RDRP regions between swine HEV and non-U.S. HEV strains varied from 74 to 76% at the nucleotide level, and 84 to 89% at the amino acid level. The GDD tripeptide motif found in all viral RDRP is conserved among different strains (data not shown). In the putative helicase region, a slightly higher sequence identity between swine HEV and non-U.S. HEV strains was observed, 74 to 77% at the nucleotide level and 91 to 92% at the amino acid level. Asian strains of HEV, Burma (14), Myanmar (16), Pakistan (18), China (19) and Madras (India, Genbank accession no. X99441) are closely related to each other. The ORF1 of the Mexican strain of HEV (15), like ORFs 2 and 3, also showed much greater sequence divergence from other HEV strains, ranging from 73 to 80% sequence identity at the nucleotide level and 85 to 94% at the amino acid level. However, the sequence identity between swine HEV and the Mexican strain was as divergent as those between swine HEV or the Mexican strain and non-U.S. strains of HEV.

The 3' NCR of swine HEV was also amplified and sequenced. The primer sequence in the extreme 3'-end was excluded, and the 3' NCR region containing the remaining 54 bp of swine HEV was compared with the corresponding regions of other HEV strains. The 3' NCR of swine HEV appeared to be very divergent: it shared about 87% sequence identity with that of the US-1 strain, but only about 58 to 70% sequence identity with the corresponding regions of the Asian strains. The 3' NCR of the Mexican strain is the longest, and varied extensively from all other HEV strains, including US-1 and swine HEV. In contrast, the 3' NCRs among the Asian strains were very conserved, ranging from 96 to 98% nucleotide sequence identity. The 5' NCR of swine HEV was also amplified. However, only 9 nucleotides were left in the 5' NCR of swine HEV after excluding the primer sequence used for the amplification. Therefore, further analysis of this region was not performed.

Experimental inoculation of non-human primates with swine HEV.

Two rhesus monkeys, RH-H397 (female) and RH-H398 (male) and one female chimpanzee (CH-5835) were each inoculated (Week 0) intravenously with 0.5 ml (rhesus) or 1.0 ml (chimpanzee) of a 10% fecal suspension (equivalent to approximately $10^3$ rhesus infectious doses) of swine HEV. Weekly serum samples were tested for anti-HEV by ELISA and for ALT levels by standard methods. The results are shown in Table 4.

TABLE 4

| Week Post-inoculation | ALT (U/L) | | | Anti-HEV IgG | | |
|---|---|---|---|---|---|---|
| | RH-H397 | RH-H398 | CH-5835 | RH-H397 | RH-H398 | CH-5835 |
| 0 | 42 | 35 | 29 | <1:100[1] | <1:100 | <1:100 |
| 1 | 43 | 30 | 26 | <1:100 | <1:100 | <1:100 |
| 2 | 43 | 33 | 27 | <1:100 | <1:100 | <1:100 |
| 3 | 97 | 38 | 31 | <1:100 | <1:100 | <1:100 |
| 4 | 81 | 39 | 30 | 1:100 | 1:100 | <1:100 |
| 5 | 96 | 37 | 26 | 1:100 | 1:1000 | <1:100 |
| 6 | 67 | 32 | 35 | 1:100 | 1:100 | 1:100 |
| 7 | 54 | 47 | 28 | 1:10,000 | 1:10,000 | 1:100 |
| 8 | 44 | 35 | 25 | 1:10,000 | 1:10,000 | 1:1,000 |
| 9 | 50 | 37 | 30 | 1:10,000 | 1:1,000 | 1:100 |
| 10 | 44 | 55 | 23 | 1:1,000 | 1:1,000 | 1:100 |
| 11 | 49 | 37 | 33 | 1:1,000 | 1:100 | 1:100 |
| 12 | 59 | 41 | 25 | 1:1,000 | 1:1,000 | 1:100 |
| 13 | 40 | 30 | 34 | 1:1,000 | 1:100 | 1:100 |
| 14 | 52 | 34 | [2]ND | 1:1,000 | 1:1,000 | ND |

[1]The dilution presented is the dilution of sera which gave a positive response for anti-HEV IgG in ELISA. A positive response with a dilution of 1:100 or greater is considered evidence of serconversion.
[2]ND = not determined.

Animals RH-H398 and CH-5835 showed no elevation in ALT levels following inoculation with the swine HEV while RH-H397 showed a slight increase in ALT levels at weeks 3, 4 and 5 post-inoculation.

In addition, both rhesus monkeys seroconverted at week 4 postinoculation while the chimpanzee seroconverted at week 6 postinoculation. Thus, the data presented in Table 4 demonstrates that in surrogates of man, the swine HEV of the present invention is completely or almost completely attenuated and elicits a strong antibody response.

Cross Challenge of Rhesus Monkeys Previously Infected With Swine HEV

Rhesus monkey RH-H397 is to be challenged intravenously with 0.5 ml (a $10^{-2}$ dilution of the SAR55 stool pool diluted an additional 1:3 with PBS before inoculation) of $10^4$ monkey infectious doses ($MID_{50}$) of the SAR55 Pakistani strain of HEV (18) and Rhesus monkey RH-H398 is to be challenged intravenously with 0.5 ml ( a $10^{-2}$ dilution of the MEX14 stool pool) of $10^4$ $MID_{50}$ of the MEX-14 Mexican strain of HEV (15) respectively.

Post-challenge, weekly serum samples are obtained and tested for viral RNA, anti-HEV and ALT levels by standard methods.

REFERENCES

1. Purcell, R. H. (1996) in *Fields Virology*, eds. Fields, B. N., Knipe, D. M., Howley, P. M. et al. (Lippincott-Raven Publishers, Philadelphia), 3rd ed. Vol. 2, pp. 2831–2843.
2. Wong, D. C., Purcell, R. H., Sreenivasan, M. A., Prasad, S. R. & Pavri, K. M. (1980) *Lancet*2, 876–878.
3. Arankalle, V. A., Tsarev, S. A., Chadha, M. S., Alling, D. W., Emerson, S. U., Banerjee, K. & Purcell, R. H. (1995) *J. Infect Dis* 171 447–450.

4. Bradley, D. W. (1992) *Rev Med Virol* 2, 19–28.
5. Skidmore, S. J., Yarbough, P. O., Gabor, K. A., Tarn, A. W. & Reyes, G. R. (1991) *Lancet* 337, 1541.
6. Dawson, G. J., Mushahwar, I. K., Chau, K. H. & Gitnick, G. L. (1992) *Lancet* 340, 426–427.
7. Dawson, G. J., Chau, K. H., Cabal, C. M., Yarbough, P. O., Reyes, G. R. & Mushahwar, I. K. (1992) *J Virol Methods* 38, 175–186
8. Tsarev, S. A., Tsareva, T. S., Emerson, S. U., Kapikian, A. Z., Ticehurst, J., London, W. & Purcell, R. H. (1993) *J. Infect. Dis.* 168, 369–378.
9. Thomas, D. L., Yarbough, P. O., Vlahov, D., Tsarev, S. A., Nelson, K. E., Saah, A. J. & Purcell, r. H. (1997) *J. Clin. Microbiol.* 35, 1244–1247.
10. Clayson, E. T., Innis, B. L., Myint, K. S. A., Narupiti, S., Vaughn, D. W., Giri, S., Ranabhat, P. & Shrestha, M. P. (1995) *Am J Trop Med Hyd* 53, 228–232.
11. Balayan, M. S., Usmanov, R. K., Zamyatina, D. I. & Karas, F. R. (1990) *J Med Virol* 32, 58–59.
12. Tsarev, S. A., Emerson, S. U., Tsareva, T. S., Yarbough, P. O., Lewis, M., Govindarajan, S., Reyes, G. R., Shapiro, M. & Purcell, R. H. (1993) *J. Infect. Dis.* 167, 1302–1306.
13. Tsarev, S. A., Tsareva, T. S., Emerson, S. U., Rippy, M. K., Zack, P., Shapiro, M. & Purcell, R. H. (1995) *J. Infect. Dis.* 172, 31–37.
14. Tam, A. W., Smith, M. M., Guerra, M. E., Huang, C.-C., Bradley, D. W., Fry, K. E. & Reyes, G. R. (1991) *Virology* 185, 120–131.
15. Huang, C. C., Nguyen, D., Fernandez, J., Yun, K. Y., Fry, K. E., Bradley, D. W., Tam, A. W. & Reyes, G. R. (1992) *Virology* 191, 550–558.
16. Aye, T. T. Uchida, T., Ma, X.-Z., Iida, F. Shikata, T., Ichikawa, M., Rikihisa, T. & Win, K. M (1993) *Virus Genes* 7, 95–110.
17. Panda, S. K., Nanda, S. K., Zafrullah, M., Ansari, I. H., Ozdener, M. H. & Jameel, S. (1995) *J. Clin. Microbiol.* 33, 2653–2659.
18. Tsarev, S. A., Emerson, S. U., Reyes, G. R., Tsareva, T. S., Legters, L. J., Malik, I. A., Iqbal, M. & Purcell, R. H. (1992) *Proc. Natl. Acad. Sci. USA* 89, 559–563.
19. Yin, S., Purcell, H. H. & Emerson, S. U. (1994) *Virus Genes* 9, 23–32.
20. Aye, T. T., Uchida, T., Ma, X.-Z., Iida, F., Shikata, T., Zhuang, H. & Win, K. M. (1992) *Nucleic Acids Res.* 20, 3512.
21. Hollinger, F. B. & Ticehurst, J. (1990) in *Fields Virology* eds. Fields, B. N., Knipe, d. M. Et al. (Raven Press, Ltd., New York), 2nd ed. Vol. 1, pp. 631–667.
22. Grieder, F. B., Davis, N. L., Aronson, J. F., Charles, P. C., Sellon, D. C., Suzuki, K. & Johnston, R. E. (1995) *Virology* 206, 994–1006.
23. Park, B. H., Matuschke, B., Lavi, E. & Gaulton, G. N. (1994) *J. Virol.* 68, 7516–7524.
24. Murphy, F. A. (1996) *Science* 273, 746–747.

What is claimed is:

1. A recombinant protein encoded by a nucleic acid sequence according to SEQ ID NO: 3.

2. The protein of claim 1, wherein said protein is purified.

3. The protein of claim 1, wherein said protein is the capsid protein of HEV encoded by ORF2 of said nucleic acid sequence and comprises the sequence of SEQ ID NO. 57.

4. The protein of claim 1, wherein said protein is the protein encoded by ORF3 of said nucleic acid sequence and comprises the sequence of SEQ ID NO. 65.

5. The protein of claim 1, wherein said protein is the protein encoded by ORF1 of said nucleic acid sequence and comprises the sequence of SEQ ID NO. 2.

* * * * *

UNITED STATES PATENT AND TRADEMARK OFFICE
CERTIFICATE OF CORRECTION

PATENT NO. : 6,432,408 B1
DATED : August 13, 2002
INVENTOR(S) : Xiang-Jin Meng et al.

It is certified that error appears in the above-identified patent and that said Letters Patent is hereby corrected as shown below:

Title page,
Item [54], at the beginning of the title insert, -- A --.
Item [73], Assignee after "The" insert -- Government of the --, after "United States of America" insert -- , --, after "as represented by the" insert -- Secretary, --.
Item [57], ABSTRACT,
Line 1, replace the word "chaterization" with -- characterization --.

Signed and Sealed this

Seventh Day of January, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,432,408 B1
DATED : August 13, 2002
INVENTOR(S) : Xiang-Jin Meng, Suzanne U. Emerson and Robert H. Purcell It is certified that error appears in the above-identified patent and that said Letters Patent is hereby corrected as shown below:

Column 93,
Lines 57-58, after "nucleic acid sequence" delete "and comprises" and insert -- which consists of --.

Column 94,
Line 53, after "nucleic acid sequence" delete "and comprises" and insert -- which consists of --.
Lines 56-57, after "nucleic acid sequence" delete "and comprises" and insert -- which consists of --.

Signed and Sealed this

Twenty-eighth Day of December, 2004

JON W. DUDAS
*Director of the United States Patent and Trademark Office*